United States Patent
Akritopoulou-Zanze et al.

(10) Patent No.: US 7,348,346 B2
(45) Date of Patent: Mar. 25, 2008

(54) PHARMACEUTICAL COMPOSITIONS AS INHIBITORS OF DIPEPTIDYL PEPTIDASE-IV (DPP-IV)

(75) Inventors: Irini Akritopoulou-Zanze, Lake Bluff, IL (US); Daria Darczak, Chicago, IL (US); Jürgen Dinges, Grayslake, IL (US); Stevan W. Djuric, Libertyville, IL (US); Ethan D. Hoff, Racine, WI (US); Hana A. Kopecka, Vernon Hills, IL (US); Jyoti R. Patel, Libertyville, IL (US); Zhonghua Pei, Libertyville, IL (US); Qi Shuai, Gurnee, IL (US); Kathy Sarris, Buffalo Grove, IL (US); Hing L. Sham, Vernon Hills, IL (US); Paul E. Wiedeman, Deerfield, IL (US)

(73) Assignee: Abbott Laboratories, Abbott Park, IL (US)

( * ) Notice: Subject to any disclaimer, the term of this patent is extended or adjusted under 35 U.S.C. 154(b) by 451 days.

(21) Appl. No.: 11/075,319

(22) Filed: Mar. 8, 2005

(65) Prior Publication Data

US 2005/0209249 A1  Sep. 22, 2005

Related U.S. Application Data

(60) Provisional application No. 60/551,079, filed on Mar. 8, 2004.

(51) Int. Cl.
*A61K 31/426* (2006.01)
*A61K 31/4025* (2006.01)
*C07D 277/04* (2006.01)

(52) U.S. Cl. .................. 514/365; 548/146; 548/200; 548/517; 548/518; 514/408; 514/422; 514/423

(58) Field of Classification Search ........... 548/146, 548/200, 517, 518; 514/365, 408, 422, 423
See application file for complete search history.

(56) References Cited

U.S. PATENT DOCUMENTS 7,205,409 B2 *  4/2007  Pei et al. ............... 546/153
7,238,724 B2 *  7/2007  Madar et al. ........... 514/422
7,262,207 B2 *  8/2007  Madar et al. ........... 514/326

FOREIGN PATENT DOCUMENTS

| WO | 9515309 | 6/1995 |
|----|---------|--------|
| WO | 0214271 | 2/2002 |
| WO | 0230890 | 4/2002 |
| WO | 03024942 | 3/2003 |
| WO | 0384940 | 10/2003 |
| WO | 2004016587 | 2/2004 |
| WO | 2005073186 | 8/2005 |
| WO | 2006073167 | 7/2006 |

OTHER PUBLICATIONS

Sakashaita, H., et al. *1-((S)-c-Substituted prolyl)-(S)-2-cyanopyrrolidine as a novel series of highly potent DPP-IV inhibitors* Bioorg. Med. Chem. Lett. 15: 2441-2445 (2005).

Sakashaita, H., et al. *[(S)-c-(Arylamino)prolyl]thiazolidine compounds as a novel series of potent and stable DPP-IV inhibitors* Bioorg. Med. Chem. Lett. 14: 3662-3671 (2006).

Tsai, et al. *Substituted pyrrolidine-2,4-icarboxylic acid amides as potent dipeptidyl peptidase IV inhibitors* Bioorg. Med. Chem. Lett. 16: 3268-3272 (2006).

Guohua, et al., *Diprolyl nitriles as potent dipeptidyl peptidase IV inhibitors* Bioorg. Med. Chem. Lett. 15: 3992-3995 (2005).

* cited by examiner

*Primary Examiner*—Golam M. M. Shameem
(74) *Attorney, Agent, or Firm*—Andrew M. Parial; Johanna M. Corbin

(57) ABSTRACT

The present invention relates to compounds of formula (I),

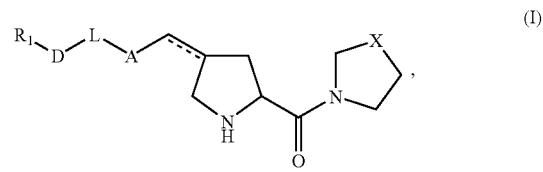

which inhibit dipeptidyl peptidase IV (DPP-IV) and are useful for the prevention or treatment of diabetes, especially type II diabetes, as well as hyperglycemia, syndrome X, hyperinsulinemia, obesity, atherosclerosis, and various immunomodulatory diseases.

2 Claims, No Drawings

PHARMACEUTICAL COMPOSITIONS AS INHIBITORS OF DIPEPTIDYL PEPTIDASE-IV (DPP-IV)

This application claims priority from U.S. Provisional Patent Application Ser. No. 60/551,079, filed Mar. 8, 2004.

FIELD OF THE INVENTION

The present invention relates to compounds that inhibit dipeptidyl peptidase IV (DPP-IV) and are useful for the prevention or treatment of diabetes, especially type II diabetes, as well as hyperglycemia, syndrome X, hyperinsulinemia, obesity, atherosclerosis, and various immunomodulatory diseases.

BACKGROUND OF THE INVENTION

Dipeptidyl peptidase IV (DPP-IV, CD26, EC 3.4.14.5) is a serine protease with specificity for cleaving Xaa-Pro and, to a lesser extent, Xaa-Ala dipeptides from the N-termini of polypeptides and proteins. DPP-IV is a non-classical serine protease in that the catalytic triad of Ser-Asp-His, found in the C-terminal region of the enzyme, is in reverse order to that found in classical serine proteases. DPP-IV is widely expressed in mammalian tissue as a type II integral membrane protein. DPP-IV is expressed on the surface of differentiated epithelial cells of the intestine, liver, kidney proximal tubules, prostate, corpus luteum, and on leukocyte subsets such as lymphocytes and macrophages. A soluble form of the enzyme is found in serum that has structure and function identical to the membrane-bound form of the enzyme but lacks the hydrophobic transmembrane domain.

DPP-IV has many physiologically relevant substrates such as chemokines, RANTES (regulated on activation normal T cell expressed and secreted), eotaxin, and macrophage-derived chemokine, neuropeptides such as NPY (neuropeptide Y) and substance P, vasoactive peptides, and incretins such as GLP-1 (glucagon-like peptide-1) and GIP (gastric inhibitory peptide/glucose-dependent insulinotropic polypeptide). GLP-1 is a 30 amino acid peptide hormone produced in the L cells of the distal small intestine in response to ingested nutrients. GLP-1 binding to its receptor on various tissues stimulates insulin gene expression, biosynthesis and glucose-dependent insulin secretion, inhibits glucagon secretion, promotes satiety, slows gastric emptying and promotes growth of pancreatic beta cells. Based on this profile, GLP-1-based therapies are expected to be beneficial in the treatment of type II diabetes and obesity. Studies in which type II diabetic patients have been infused with GLP-1 have demonstrated efficacy in normalizing both fasted and prandial glycemia. However, active GLP-1 (7-36) amide is rapidly converted by DPP-IV to GLP-1 (9-36), which is inactive or is a receptor antagonist. The short half-life of GLP-1 in the circulation (1-1.5 minutes) is a major obstacle to its use as a therapeutic agent. To circumvent the drawback of the short half-life of GLP-1, inhibitors of DPP-IV, the primary degradative enzyme of GLP-1, increase the level of active circulating GLP-1 (7-36) amide. DPP-IV inhibitors have been demonstrated to improve glucose tolerance in type II diabetes.

Although DPP-IV inhibitors have demonstrated improved glucose tolerance in type II diabetes, many suffer from having short half-life and toxicity. Therefore, there is a need for DPP-IV inhibitors having an improved pharmacological profile as an alternative for the treatment of type II diabetes.

Therefore, the inhibition of DPP-IV offers an attractive therapeutic treatment for type II diabetes and obesity.

SUMMARY OF THE INVENTION

The present invention is directed to compounds of formula (I),

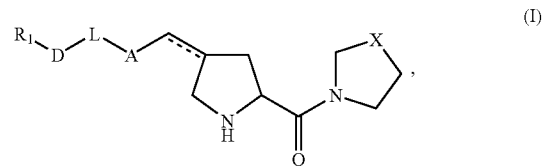

or therapeutically suitable salt, ester or prodrug, thereof, wherein

is a member selected from the group consisting of a single and double bond;

A is a member selected from the group consisting of —C(O)—, —N($R_a$)—C(O)—, —C(O)—N($R_a$)—, —N($R_a$)—, —N($R_a$)—S(O)$_2$—, and —S(O)$_2$—N($R_a$)—;

D is a member selected from the group consisting of a bond, —C(O)—, —C(O)—N($R_b$)—, —N($R_b$)—, —N($R_b$)—C(O)—, —N($R_b$)—S(O)$_2$—, —O—, and —S(O)$_2$—N($R_b$)—;

L is a member selected from the group consisting of a bond, —(CH$_2$)$_m$—CR$_d$R$_e$—(CH$_2$)$_n$—, aryl, cycloalkyl, and heterocycle;

m and n are each independently 0, 1, 2, 3 or 4;

$R_1$ is a member selected from the group consisting of aryl, alkyl, arylalkyl, cycloalkyl and heterocycle;

$R_a$ and $R_b$ are each independently members selected from the group consisting of hydrogen, alkyl, arylalkyl and heterocyclealkyl and hydroxyalkyl;

$R_d$ and $R_e$ are each independently members selected from the group consisting of hydrogen, alkyl, alkoxy, alkoxyalkyl, aryl, arylalkyl, halo, haloalkyl, heterocycle, heterocyclealkyl, hydroxy and hydroxyalkyl, and $R_d$ and $R_e$ taken together with the atom to which they are attached form cycloalkyl; and X is a member selected from the group consisting of —CH$_2$—, —CHF—, —CF$_2$—, —O—, —S— and —CH$_2$O—.

According to one embodiment of the present invention, there is provided a method to improve glucose tolerance in type II diabetes comprising administering a therapeutically effective amount of a compound of formula (I). According to another embodiment of the present invention, there is provided a method for treating type 2 diabetes, insulin resistance, hyperinsulinemia, impaired glucose tolerance, obesity, hypercholesterolemia, and hypertriglyceridemia comprising administering a therapeutically effective amount of a compound of formula (I).

According to still another embodiment, the present invention is directed to a pharmaceutical composition comprising a therapeutically effective amount of a compound of formula (I) in combination with a pharmaceutically suitably carrier.

DETAILED DESCRIPTION OF THE INVENTION

The present invention is also directed to a method of treating disorders mediated by DPP-IV through inhibition of enzymatic activity. Disorders known to be regulated through enzymatic activity are diabetes, especially type II diabetes, as well as hyperglycemia, Syndrome X, hyperinsulinemia, obesity, atherosclerosis, and various immunomodulatory diseases. Therefore, according to an embodiment of the present invention there are provided compounds of formula (I), which are useful for the treatment of diabetes, especially type II diabetes, as well as hyperglycemia, Syndrome X, hyperinsulinemia, obesity, atherosclerosis, and various immunomodulatory diseases.

According to another embodiment of the present invention there is provided a compound of formula (II),

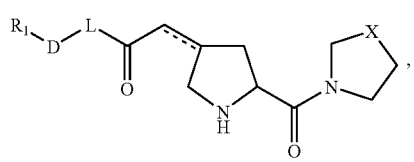

(II)

or therapeutically suitable salt, ester or prodrug, thereof, wherein is a member selected from the group consisting of a single and double bond; D is a bond or is a member selected from the group consisting of —C(O)—, —C(O)—N($R_b$)—, —N($R_b$)—, —N($R_b$)—C(O)—, —N($R_b$)—S(O)$_2$—, —O—, and —S(O)$_2$—N($R_b$)—; L is a member selected from the group consisting of a bond, —(CH$_2$)$_m$—CR$_d$R$_e$—(CH$_2$)$_n$—, aryl, cycloalkyl, and heterocycle; m and n are each independently 0, 1, 2, 3 or 4; $R_1$ is a member selected from the group consisting of aryl, alkyl, arylalkyl, cycloalkyl and heterocycle; $R_b$ is a member selected from the group consisting of hydrogen, alkyl, arylalkyl and heterocyclealkyl and hydroxyalkyl; $R_d$ and $R_e$ are each independently members selected from the group consisting of hydrogen, alkyl, alkoxy, alkoxyalkyl, aryl, arylalkyl, halo, haloalkyl, heterocycle, heterocyclealkyl, hydroxy and hydroxyalkyl, and $R_d$ and $R_e$ taken together with the atom to which they are attached form cycloalkyl; and X is a member selected from the group consisting of —CH$_2$—, —CHF—, —CF$_2$—, —O—, —S— and —CH$_2$O—.

According to another embodiment of the present invention there is provided a compound of formula (IIa),

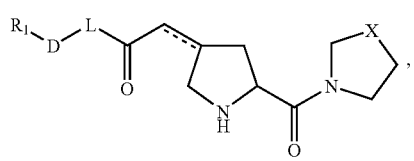

(IIa)

or therapeutically suitable salt, ester or prodrug, thereof, wherein is a member selected from the group consisting of a single and double bond; D is a bond or is a member selected from the group consisting of —C(O)—, —C(O)—N($R_b$)—, —N($R_b$)—, —N($R_b$)—C(O)—, —N($R_b$)—S(O)$_2$—, —O—, and —S(O)$_2$—N($R_b$)—; L is a member selected from the group consisting of a bond, —(CH$_2$)$_m$—CR$_d$R$_e$—(CH$_2$)$_n$—, aryl, cycloalkyl, and heterocycle; m and n are each independently 0, 1, 2, 3 or 4; $R_1$ is a member selected from the group consisting of aryl, alkyl, arylalkyl, cycloalkyl and heterocycle; $R_b$ is a member selected from the group consisting of hydrogen, alkyl, arylalkyl and heterocyclealkyl and hydroxyalkyl; $R_d$ and $R_e$ are each independently members selected from the group consisting of hydrogen, alkyl, alkoxy, alkoxyalkyl, aryl, arylalkyl, halo, haloalkyl, heterocycle, heterocyclealkyl, hydroxy and hydroxyalkyl, and $R_d$ and $R_e$ taken together with the atom to which they are attached form cycloalkyl; and X is a member selected from the group consisting of —CH$_2$—, —CHF—, —CF$_2$—, —O—, and —S—.

According to another embodiment of the present invention there is provided a compound of formula (IIa),

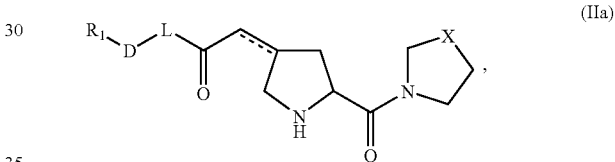

(IIa)

or therapeutically suitable salt, ester or prodrug, thereof, wherein is a member selected from the group consisting of a single and double bond; D is a bond or is a member selected from the group consisting of —C(O)—, —C(O)—N($R_b$)—, —N($R_b$)—, —N($R_b$)—C(O)—, —N($R_b$)—S(O)$_2$—, —O—, and —S(O)$_2$—N($R_b$)—; L is a member selected from the group consisting of a bond, —(CH$_2$)$_m$—CR$_d$R$_e$—(CH$_2$)$_n$—, aryl, cycloalkyl, and heterocycle; m and n are each independently 0, 1, 2, 3 or 4; $R_1$ is a member selected from the group consisting of aryl, and heterocycle, wherein said aryl group and said heterocycle is further substituted with an aryl or a heterocyclic ring as defined herein; $R_b$ is a member selected from the group consisting of hydrogen, alkyl, arylalkyl and heterocyclealkyl and hydroxyalkyl; $R_d$ and $R_e$ are each independently members selected from the group consisting of hydrogen, alkyl, alkoxy, alkoxyalkyl, aryl, arylalkyl, halo, haloalkyl, heterocycle, heterocyclealkyl, hydroxy and hydroxyalkyl, and $R_d$ and $R_e$ taken together with the atom to which they are attached form cycloalkyl; and X is a member selected from the group consisting of —CH$_2$—, —CHF—, —CF$_2$—, —O—, and —S—.

According to another embodiment of the present invention there is provided a compound of formula (IIb),

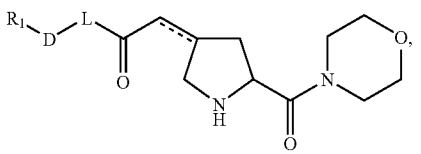

or therapeutically suitable salt, ester or prodrug, thereof, wherein

is a member selected from the group consisting of a single and double bond; D is a bond or is a member selected from the group consisting of —C(O)—, —C(O)—N($R_b$)—, —N($R_b$)—, —N($R_b$)—C(O)—, —N($R_b$)—S(O)$_2$—, —O—, and —S(O)$_2$—N($R_b$)—; L is a member selected from the group consisting of a bond, —(CH$_2$)$_m$—CR$_d$R$_e$—(CH$_2$)$_n$—, aryl, cycloalkyl, and heterocycle; m and n are each independently 0, 1, 2, 3 or 4; R$_1$ is a member selected from the group consisting of aryl, alkyl, arylalkyl, cycloalkyl and heterocycle; R$_b$ is a member selected from the group consisting of hydrogen, alkyl, arylalkyl and heterocyclealkyl and hydroxyalkyl; and R$_d$ and R$_e$ are each independently members selected from the group consisting of hydrogen, alkyl, alkoxy, alkoxyalkyl, aryl, arylalkyl, halo, haloalkyl, heterocycle, heterocyclealkyl, hydroxy and hydroxyalkyl, and R$_d$ and R$_e$ taken together with the atom to which they are attached form cycloalkyl.

According to another embodiment of the present invention there is provided a compound of formula (III),

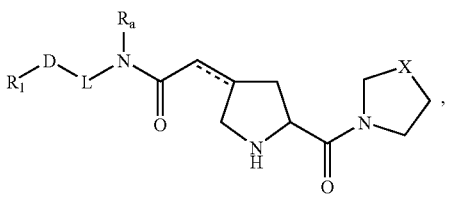

or therapeutically suitable salt, ester or prodrug, thereof, wherein

is a member selected from the group consisting of a single and double bond; D is a bond or is a member selected from the group consisting of —C(O)—, —C(O)—N($R_b$)—, —N($R_b$)—, —N($R_b$)—C(O)—, —N($R_b$)—S(O)$_2$—, —O—, and —S(O)$_2$—N($R_b$)—; L is a member selected from the group consisting of a bond, —(CH$_2$)$_m$—CR$_d$R$_e$—(CH$_2$)$_n$—, aryl, cycloalkyl, and heterocycle; m and n are each independently 0, 1, 2, 3 or 4; R$_1$ is a member selected from the group consisting of aryl, alkyl, arylalkyl, cycloalkyl and heterocycle; R$_a$ and R$_b$ are each independently members selected from the group consisting of hydrogen, alkyl, arylalkyl and heterocyclealkyl and hydroxyalkyl; R$_d$ and R$_e$ are each independently members selected from the group consisting of hydrogen, alkyl, alkoxy, alkoxyalkyl, aryl, arylalkyl, halo, haloalkyl, heterocycle, heterocyclealkyl, hydroxy and hydroxyalkyl, and R$_d$ and R$_e$ taken together with the atom to which they are attached form cycloalkyl; and X is a member selected from the group consisting of —CH$_2$—, —CHF—, —CF$_2$—, —O—, —S— and —CH$_2$O—.

According to another embodiment of the present invention there is provided a compound of formula (IIIa),

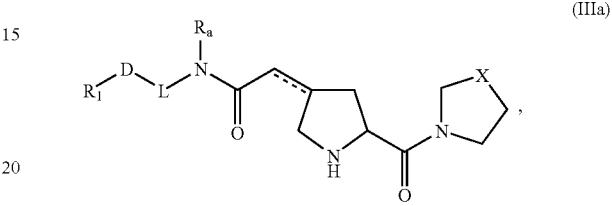

or therapeutically suitable salt, ester or prodrug, thereof, wherein

is a member selected from the group consisting of a single and double bond; D is a bond or is a member selected from the group consisting of —C(O)—, —C(O)—N($R_b$)—, —N($R_b$)—, —N($R_b$)—C(O)—, —N($R_b$)—S(O)$_2$—, —O—, and —S(O)$_2$—N($R_b$)—; L is a member selected from the group consisting of a bond, —(CH$_2$)$_m$—CR$_d$R$_e$—(CH$_2$)$_n$—, aryl, cycloalkyl, and heterocycle; m and n are each independently 0, 1, 2, 3 or 4; R$_1$ is a member selected from the group consisting of aryl, alkyl, arylalkyl, cycloalkyl and heterocycle; R$_a$ and R$_b$ are each independently members selected from the group consisting of hydrogen, alkyl, arylalkyl and heterocyclealkyl and hydroxyalkyl; R$_d$ and R$_e$ are each independently members selected from the group consisting of hydrogen, alkyl, alkoxy, alkoxyalkyl, aryl, arylalkyl, halo, haloalkyl, heterocycle, heterocyclealkyl, hydroxy and hydroxyalkyl, and R$_d$ and R$_e$ taken together with the atom to which they are attached form cycloalkyl; and X is a member selected from the group consisting of —CH$_2$—, —CHF—, —CF$_2$—, —O—, and —S—.

According to another embodiment of the present invention there is provided a compound of formula (IIIa),

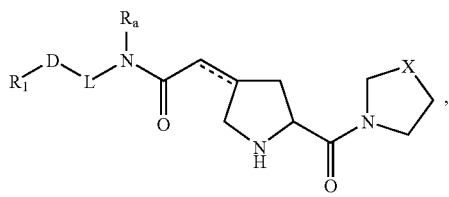

or therapeutically suitable salt, ester or prodrug, thereof, wherein

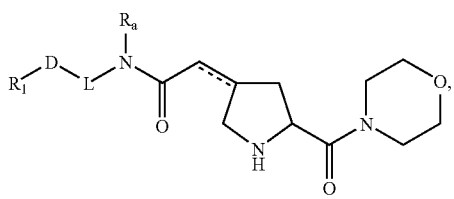

is a member selected from the group consisting of a single and double bond; D is a bond or is a member selected from the group consisting of —C(O)—, —C(O)—N(R$_b$)—, —N(R$_b$)—, —N(R$_b$)—C(O)—, —N(R$_b$)—S(O)$_2$—, —O—, and —S(O)$_2$—N(R$_b$)—; L is a member selected from the group consisting of a bond, —(CH$_2$)$_m$—CR$_d$R$_e$—(CH$_2$)$_n$—, aryl, cycloalkyl, and heterocycle; m and n are each independently 0, 1, 2, 3 or 4; R$_1$ is a member selected from the group consisting of aryl, and heterocycle, wherein said aryl group and said heterocycle is further substituted with an aryl or a heterocyclic ring as defined herein; R$_a$ and R$_b$ are each independently members selected from the group consisting of hydrogen, alkyl, arylalkyl and heterocyclealkyl and hydroxyalkyl; R$_d$ and R$_e$ are each independently members selected from the group consisting of hydrogen, alkyl, alkoxy, alkoxyalkyl, aryl, arylalkyl, halo, haloalkyl, heterocycle, heterocyclealkyl, hydroxy and hydroxyalkyl, and R$_d$ and R$_e$ taken together with the atom to which they are attached form cycloalkyl; and X is a member selected from the group consisting of —CH$_2$—, —CHF—, —CF$_2$—, —O—, and —S—.

According to another embodiment of the present invention there is provided a compound of formula (IIIb), (IIIb)

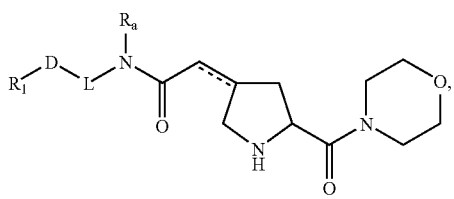

or therapeutically suitable salt, ester or prodrug, thereof, wherein is a member selected from the group consisting of a single and double bond; D is a bond or is a member selected from the group consisting of —C(O)—, —C(O)—N(R$_b$)—, —N(R$_b$)—, —N(R$_b$)—C(O)—, —N(R$_b$)—S(O)$_2$—, —O—, and —S(O)$_2$—N(R$_b$)—; L is a member selected from the group consisting of a bond, —(CH$_2$)$_m$—CR$_d$R$_e$—(CH$_2$)$_n$—, aryl, cycloalkyl, and heterocycle; m and n are each independently 0, 1, 2, 3 or 4; R$_1$ is a member selected from the group consisting of aryl, alkyl, arylalkyl, cycloalkyl and heterocycle; R$_a$ and R$_b$ are each independently members selected from the group consisting of hydrogen, alkyl, arylalkyl and heterocyclealkyl and hydroxyalkyl; and R$_d$ and R$_e$ are each independently members selected from the group consisting of hydrogen, alkyl, alkoxy, alkoxyalkyl, aryl, arylalkyl, halo, haloalkyl, heterocycle, heterocyclealkyl, hydroxy and hydroxyalkyl, and R$_d$ and R$_e$ taken together with the atom to which they are attached form cycloalkyl.

According to another embodiment of the present invention there is provided a compound of formula (IV), (IV)

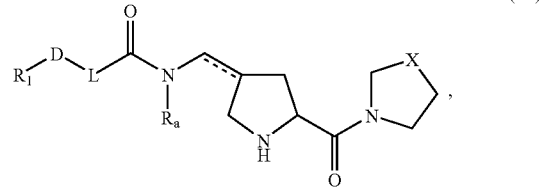

or therapeutically suitable salt, ester or prodrug, thereof, wherein is a member selected from the group consisting of a single and double bond; D is a bond or is a member selected from the group consisting of —C(O)—, —C(O)—N(R$_b$)—, —N(R$_b$)—, —N(R$_b$)—C(O)—, —N(R$_b$)—S(O)$_2$—, —O—, and —S(O)$_2$—N(R$_b$)—; L is a member selected from the group consisting of a bond, —(CH$_2$)$_m$—CR$_d$R$_e$—(CH$_2$)$_n$—, aryl, cycloalkyl, and heterocycle; m and n are each independently 0, 1, 2, 3 or 4; R$_1$ is a member selected from the group consisting of aryl, alkyl, arylalkyl, cycloalkyl and heterocycle; R$_a$ and R$_b$ are each independently members selected from the group consisting of hydrogen, alkyl, arylalkyl and heterocyclealkyl and hydroxyalkyl; R$_d$ and R$_e$ are each independently members selected from the group consisting of hydrogen, alkyl, alkoxy, alkoxyalkyl, aryl, arylalkyl, halo, haloalkyl, heterocycle, heterocyclealkyl, hydroxy and hydroxyalkyl, and R$_d$ and R$_e$ taken together with the atom to which they are attached form cycloalkyl; and X is a member selected from the group consisting of —CH$_2$—, —CHF—, —CF$_2$—, —O—, —S— and —CH$_2$O—.

According to another embodiment of the present invention there is provided a compound of formula (IVa), (IVa)

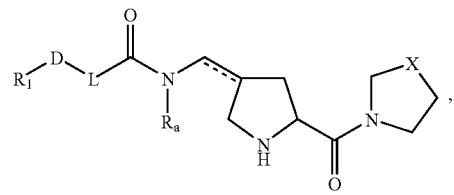

or therapeutically suitable salt, ester or prodrug, thereof, wherein is a member selected from the group consisting of a single and double bond; D is a bond or is a member selected from the group consisting of —C(O)—, —C(O)—N(R$_b$)—, —N(R$_b$)—, —N(R$_b$)—C(O)—, —N(R$_b$)—S(O)$_2$—, —O—, and —S(O)₂—N(R_b)—; L is a member selected from the group consisting of a bond, —(CH₂)_m—CR_dR_e—(CH₂)_n—, aryl, cycloalkyl, and heterocycle; m and n are each independently 0, 1, 2, 3 or 4; R₁ is a member selected from the group consisting of aryl, alkyl, arylalkyl, cycloalkyl and heterocycle; R_a and R_b are each independently members selected from the group consisting of hydrogen, alkyl, arylalkyl and heterocyclealkyl and hydroxyalkyl; R_d and R_e are each independently members selected from the group consisting of hydrogen, alkyl, alkoxy, alkoxyalkyl, aryl, arylalkyl, halo, haloalkyl, heterocycle, heterocyclealkyl, hydroxy and hydroxyalkyl, and R_d and R_e taken together with the atom to which they are attached form cycloalkyl; and X is a member selected from the group consisting of —CH₂—, —CHF—, —CF₂—, —O—, and —S—.

According to another embodiment of the present invention there is provided a compound of formula (IVa),

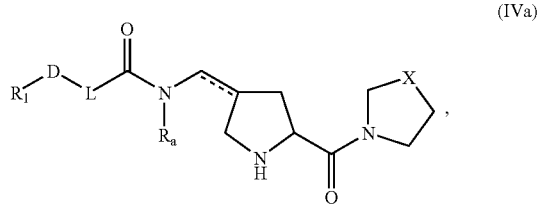

(IVa)

or therapeutically suitable salt, ester or prodrug, thereof, wherein

≈ is a member selected from the group consisting of a single and double bond; D is a bond or is a member selected from the group consisting of —C(O)—, —C(O)—N(R_b)—, —N(R_b)—, —N(R_b)—C(O)—, —N(R_b)—S(O)₂—, —O—, and —S(O)₂—N(R_b)—; L is a member selected from the group consisting of a bond, —(CH₂)_m—CR_dR_e—(CH₂)_n—, aryl, cycloalkyl, and heterocycle; m and n are each independently 0, 1, 2, 3 or 4; R₁ is a member selected from the group consisting of aryl, and heterocycle, wherein said aryl group and said heterocycle is further substituted with an aryl or a heterocyclic ring as defined herein; R_a and R_b are each independently members selected from the group consisting of hydrogen, alkyl, arylalkyl and heterocyclealkyl and hydroxyalkyl; R_d and R_e are each independently members selected from the group consisting of hydrogen, alkyl, alkoxy, alkoxyalkyl, aryl, arylalkyl, halo, haloalkyl, heterocycle, heterocyclealkyl, hydroxy and hydroxyalkyl, and R_d and R_e taken together with the atom to which they are attached form cycloalkyl; and X is a member selected from the group consisting of —CH₂—, —CHF—, —CF₂—, —O—, and —S—.

According to another embodiment of the present invention there is provided a compound of formula (IVb),

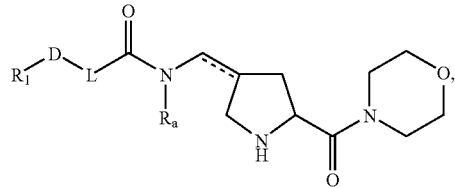

(IVb)

or therapeutically suitable salt, ester or prodrug, thereof, wherein

≈ is a member selected from the group consisting of a single and double bond; D is a bond or is a member selected from the group consisting of —C(O)—, —C(O)—N(R_b)—, —N(R_b)—, —N(R_b)—C(O)—, —N(R_b)—S(O)₂—, —O—, and —S(O)₂—N(R_b)—; L is a member selected from the group consisting of a bond, —(CH₂)_m—CR_dR_e—(CH₂)_n—, aryl, cycloalkyl, and heterocycle; m and n are each independently 0, 1, 2, 3 or 4; R₁ is a member selected from the group consisting of aryl, alkyl, arylalkyl, cycloalkyl and heterocycle; R_a and R_b are each independently members selected from the group consisting of hydrogen, alkyl, arylalkyl and heterocyclealkyl and hydroxyalkyl; and R_d and R_e are each independently members selected from the group consisting of hydrogen, alkyl, alkoxy, alkoxyalkyl, aryl, arylalkyl, halo, haloalkyl, heterocycle, heterocyclealkyl, hydroxy and hydroxyalkyl, and R_d and R_e taken together with the atom to which they are attached form cycloalkyl.

According to another embodiment of the present invention there is provided a compound of formula (V),

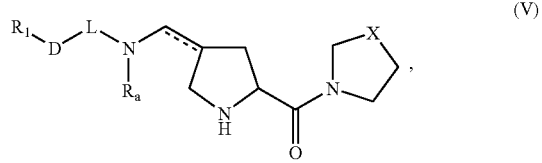

(V)

or therapeutically suitable salt, ester or prodrug, thereof, wherein

≈ is a member selected from the group consisting of a single and double bond; D is a bond or is a member selected from the group consisting of —C(O)—, —C(O)—N(R_b)—, —N(R_b)—, —N(R_b)—C(O)—, —N(R_b)—S(O)₂—, —O—, and —S(O)₂—N(R_b)—; L is a member selected from the group consisting of a bond, —(CH₂)_m—CR_dR_e—(CH₂)_n—, aryl, cycloalkyl, and heterocycle; m and n are each independently 0, 1, 2, 3 or 4; R₁ is a member selected from the group consisting of aryl, alkyl, arylalkyl, cycloalkyl and heterocycle; $R_a$ and $R_b$ are each independently members selected from the group consisting of hydrogen, alkyl, arylalkyl and heterocyclealkyl and hydroxyalkyl; $R_d$ and $R_e$ are each independently members selected from the group consisting of hydrogen, alkyl, alkoxy, alkoxyalkyl, aryl, arylalkyl, halo, haloalkyl, heterocycle, heterocyclealkyl, hydroxy and hydroxyalkyl, and $R_d$ and $R_e$ taken together with the atom to which they are attached form cycloalkyl; and X is a member selected from the group consisting of —CH$_2$—, —CHF—, —CF$_2$—, —O—, —S— and —CH$_2$O—.

According to another embodiment of the present invention there is provided a compound of formula (Va),

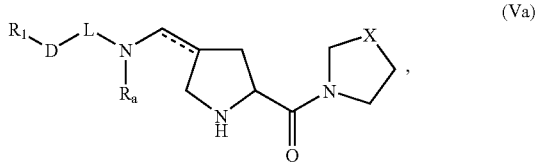

(Va)

or therapeutically suitable salt, ester or prodrug, thereof, wherein is a member selected from the group consisting of a single and double bond; D is a bond or is a member selected from the group consisting of —C(O)—, —C(O)—N(R$_b$)—, —N(R$_b$)—, —N(R$_b$)—C(O)—, —N(R$_b$)—S(O)$_2$—, —O—, and —S(O)$_2$—N(R$_b$)—; L is a member selected from the group consisting of a bond, —(CH$_2$)$_m$—CR$_d$R$_e$—(CH$_2$)$_n$—, aryl, cycloalkyl, and heterocycle; m and n are each independently 0, 1, 2, 3 or 4; $R_1$ is a member selected from the group consisting of aryl, alkyl, arylalkyl, cycloalkyl and heterocycle; $R_a$ and $R_b$ are each independently members selected from the group consisting of hydrogen, alkyl, arylalkyl and heterocyclealkyl and hydroxyalkyl; $R_d$ and $R_e$ are each independently members selected from the group consisting of hydrogen, alkyl, alkoxy, alkoxyalkyl, aryl, arylalkyl, halo, haloalkyl, heterocycle, heterocyclealkyl, hydroxy and hydroxyalkyl, and $R_d$ and $R_e$ taken together with the atom to which they are attached form cycloalkyl; and X is a member selected from the group consisting of —CH$_2$—, —CHF—, —CF$_2$—, —O—, and —S—.

According to another embodiment of the present invention there is provided a compound of formula (Va),

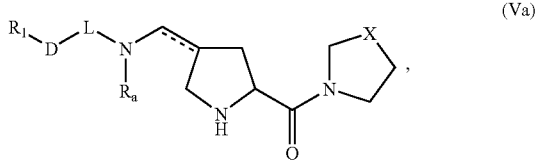

(Va)

or therapeutically suitable salt, ester or prodrug, thereof, wherein is a member selected from the group consisting of a single and double bond; D is a bond or is a member selected from the group consisting of —C(O)—, —C(O)—N(R$_b$)—, —N(R$_b$)—, —N(R$_b$)—C(O)—, —N(R$_b$)—S(O)$_2$—, —O—, and —S(O)$_2$—N(R$_b$)—; L is a member selected from the group consisting of a bond, —(CH$_2$)$_m$—CR$_d$R$_e$—(CH$_2$)$_n$—, aryl, cycloalkyl, and heterocycle; m and n are each independently 0, 1, 2, 3 or 4; $R_1$ is a member selected from the group consisting of aryl, and heterocycle, wherein said aryl group and said heterocycle is further substituted with an aryl or a heterocyclic ring as defined herein; $R_a$ and $R_b$ are each independently members selected from the group consisting of hydrogen, alkyl, arylalkyl and heterocyclealkyl and hydroxyalkyl; $R_d$ and $R_e$ are each independently members selected from the group consisting of hydrogen, alkyl, alkoxy, alkoxyalkyl, aryl, arylalkyl, halo, haloalkyl, heterocycle, heterocyclealkyl, hydroxy and hydroxyalkyl, and $R_d$ and $R_e$ taken together with the atom to which they are attached form cycloalkyl; and X is a member selected from the group consisting of —CH$_2$—, —CHF—, —CF$_2$—, —O—, and —S—.

According to another embodiment of the present invention there is provided a compound of formula (Vb),

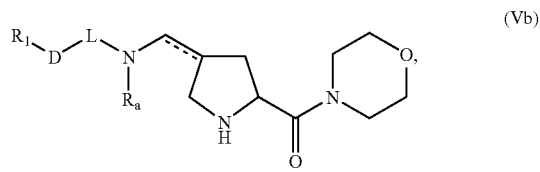

(Vb)

or therapeutically suitable salt, ester or prodrug, thereof, wherein is a member selected from the group consisting of a single and double bond; D is a bond or is a member selected from the group consisting of —C(O)—, —C(O)—N(R$_b$)—, —N(R$_b$)—, —N(R$_b$)—C(O)—, —N(R$_b$)—S(O)$_2$—, —O—, and —S(O)$_2$—N(R$_b$)—; L is a member selected from the group consisting of a bond, —(CH$_2$)$_m$—CR$_d$R$_e$—(CH$_2$)$_n$—, aryl, cycloalkyl, and heterocycle; m and n are each independently 0, 1, 2, 3 or 4; $R_1$ is a member selected from the group consisting of aryl, alkyl, arylalkyl, cycloalkyl and heterocycle; $R_a$ and $R_b$ are each independently members selected from the group consisting of hydrogen, alkyl, arylalkyl and heterocyclealkyl and hydroxyalkyl; and $R_d$ and $R_e$ are each independently members selected from the group consisting of hydrogen, alkyl, alkoxy, alkoxyalkyl, aryl, arylalkyl, halo, haloalkyl, heterocycle, heterocyclealkyl, hydroxy and hydroxyalkyl, and $R_d$ and $R_e$ taken together with the atom to which they are attached form cycloalkyl.

According to another embodiment of the present invention there is provided a compound of formula (VI),

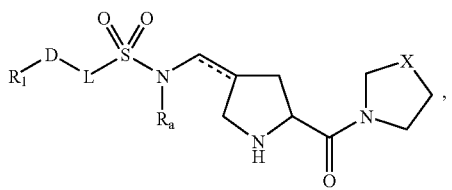
(VI)

or therapeutically suitable salt, ester or prodrug, thereof, wherein

is a member selected from the group consisting of a single and double bond; D is a bond or is a member selected from the group consisting of —C(O)—, —C(O)—N($R_b$)—, —N($R_b$)—, —N($R_b$)—C(O)—, —N($R_b$)—S(O)$_2$—, —O—, and —S(O)$_2$—N($R_b$)—; L is a member selected from the group consisting of a bond, —(CH$_2$)$_m$—CR$_d$R$_e$—(CH$_2$)$_n$—, aryl, cycloalkyl, and heterocycle; m and n are each independently 0, 1, 2, 3 or 4; $R_1$ is a member selected from the group consisting of aryl, alkyl, arylalkyl, cycloalkyl and heterocycle; $R_a$ and $R_b$ are each independently members selected from the group consisting of hydrogen, alkyl, arylalkyl and heterocyclealkyl and hydroxyalkyl; $R_d$ and $R_e$ are each independently members selected from the group consisting of hydrogen, alkyl, alkoxy, alkoxyalkyl, aryl, arylalkyl, halo, haloalkyl, heterocycle, heterocyclealkyl, hydroxy and hydroxyalkyl, and $R_d$ and $R_e$ taken together with the atom to which they are attached form cycloalkyl; and X is a member selected from the group consisting of —CH$_2$—, —CHF—, —CF$_2$—, —O—, —S— and —CH$_2$O—.

According to another embodiment of the present invention there is provided a compound of formula (VIa),

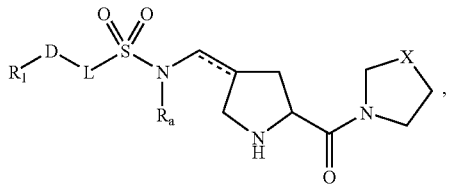
(VIa)

or therapeutically suitable salt, ester or prodrug, thereof, wherein

is a member selected from the group consisting of a single and double bond; D is a bond or is a member selected from the group consisting of —C(O)—, —C(O)—N($R_b$)—, —N($R_b$)—, —N($R_b$)—C(O)—, —N($R_b$)—S(O)$_2$—, —O—, and —S(O)$_2$—N($R_b$)—; L is a member selected from the group consisting of a bond, —(CH$_2$)$_m$—CR$_d$R$_e$—(CH$_2$)$_n$—, aryl, cycloalkyl, and heterocycle; m and n are each independently 0, 1, 2, 3 or 4; $R_1$ is a member selected from the group consisting of aryl, alkyl, arylalkyl, cycloalkyl and heterocycle; $R_a$ and $R_b$ are each independently members selected from the group consisting of hydrogen, alkyl, arylalkyl and heterocyclealkyl and hydroxyalkyl; $R_d$ and $R_e$ are each independently members selected from the group consisting of hydrogen, alkyl, alkoxy, alkoxyalkyl, aryl, arylalkyl, halo, haloalkyl, heterocycle, heterocyclealkyl, hydroxy and hydroxyalkyl, and $R_d$ and $R_e$ taken together with the atom to which they are attached form cycloalkyl; and X is a member selected from the group consisting of —CH$_2$—, —CHF—, —CF$_2$—, —O—, and —S—.

According to another embodiment of the present invention there is provided a compound of formula (VIa),

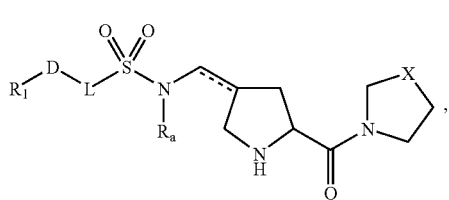
(VIa)

or therapeutically suitable salt, ester or prodrug, thereof, wherein

is a member selected from the group consisting of a single and double bond; D is a bond or is a member selected from the group consisting of —C(O)—, —C(O)—N($R_b$)—, —N($R_b$)—, —N($R_b$)—C(O)—, —N($R_b$)—S(O)$_2$—, —O—, and —S(O)$_2$—N($R_b$)—; L is a member selected from the group consisting of a bond, —(CH$_2$)$_m$—CR$_d$R$_e$—(CH$_2$)$_n$—, aryl, cycloalkyl, and heterocycle; m and n are each independently 0, 1, 2, 3 or 4; $R_1$ is a member selected from the group consisting of aryl, and heterocycle, wherein said aryl group and said heterocycle is further substituted with an aryl or a heterocyclic ring as defined herein; $R_a$ and $R_b$ are each independently members selected from the group consisting of hydrogen, alkyl, arylalkyl and heterocyclealkyl and hydroxyalkyl; $R_d$ and $R_e$ are each independently members selected from the group consisting of hydrogen, alkyl, alkoxy, alkoxyalkyl, aryl, arylalkyl, halo, haloalkyl, heterocycle, heterocyclealkyl, hydroxy and hydroxyalkyl, and $R_d$ and $R_e$ taken together with the atom to which they are attached form cycloalkyl; and X is a member selected from the group consisting of —CH$_2$—, —CHF—, —CF$_2$—, —O—, and —S—.

According to another embodiment of the present invention there is provided a compound of formula (VIb),

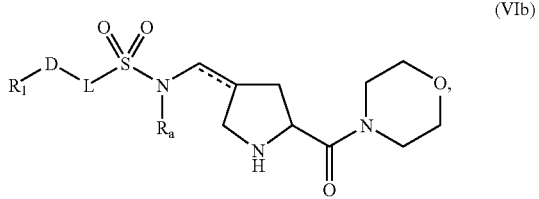

(VIb)

or therapeutically suitable salt, ester or prodrug, thereof, wherein

≈ is a member selected from the group consisting of a single and double bond; D is a bond or is a member selected from the group consisting of —C(O)—, —C(O)—N($R_b$)—, —N($R_b$)—, —N($R_b$)—C(O)—, —N($R_b$)—S(O)$_2$—, —O—, and —S(O)$_2$—N($R_b$)—; L is a member selected from the group consisting of a bond, —(CH$_2$)$_m$—CR$_d$R$_e$—(CH$_2$)$_n$—, aryl, cycloalkyl, and heterocycle; m and n are each independently 0, 1, 2, 3 or 4; R$_1$ is a member selected from the group consisting of aryl, alkyl, arylalkyl, cycloalkyl and heterocycle; R$_a$ and R$_b$ are each independently members selected from the group consisting of hydrogen, alkyl, arylalkyl and heterocyclealkyl and hydroxyalkyl; and R$_d$ and R$_e$ are each independently members selected from the group consisting of hydrogen, alkyl, alkoxy, alkoxyalkyl, aryl, arylalkyl, halo, haloalkyl, heterocycle, heterocyclealkyl, hydroxy and hydroxyalkyl, and R$_d$ and R$_e$ taken together with the atom to which they are attached form cycloalkyl.

According to another embodiment of the present invention there is provided a compound of formula (VII),

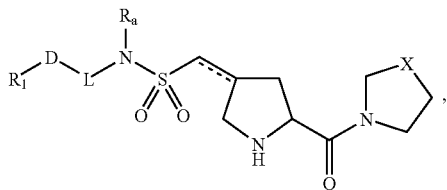

(VII)

or therapeutically suitable salt, ester or prodrug, thereof, wherein

≈ is a member selected from the group consisting of a single and double bond; D is a bond or is a member selected from the group consisting of —C(O)—, —C(O)—N($R_b$)—, —N($R_b$)—, —N($R_b$)—C(O)—, —N($R_b$)—S(O)$_2$—, —O—, and —S(O)$_2$—N($R_b$)—; L is a member selected from the group consisting of a bond, —(CH$_2$)$_m$—CR$_d$R$_e$—(CH$_2$)$_n$—, aryl, cycloalkyl, and heterocycle; m and n are each independently 0, 1, 2, 3 or 4; R$_1$ is a member selected from the group consisting of aryl, alkyl, arylalkyl, cycloalkyl and heterocycle; R$_a$ and R$_b$ are each independently members selected from the group consisting of hydrogen, alkyl, arylalkyl and heterocyclealkyl and hydroxyalkyl; R$_d$ and R$_e$ are each independently members selected from the group consisting of hydrogen, alkyl, alkoxy, alkoxyalkyl, aryl, arylalkyl, halo, haloalkyl, heterocycle, heterocyclealkyl, hydroxy and hydroxyalkyl, and R$_d$ and R$_e$ taken together with the atom to which they are attached form cycloalkyl; and X is a member selected from the group consisting of —CH$_2$—, —CHF—, —CF$_2$—, —O—, —S— and —CH$_2$O—.

According to another embodiment of the present invention there is provided a compound of formula (VIIa),

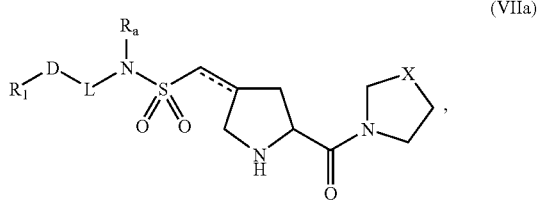

(VIIa)

or therapeutically suitable salt, ester or prodrug, thereof, wherein

≈ is a member selected from the group consisting of a single and double bond; D is a bond or is a member selected from the group consisting of —C(O)—, —C(O)—N($R_b$)—, —N($R_b$)—, —N($R_b$)—C(O)—, —N($R_b$)—S(O)$_2$—, —O—, and —S(O)$_2$—N($R_b$)—; L is a member selected from the group consisting of a bond, —(CH$_2$)$_m$—CR$_d$R$_e$—(CH$_2$)$_n$—, aryl, cycloalkyl, and heterocycle; m and n are each independently 0, 1, 2, 3 or 4; R$_1$ is a member selected from the group consisting of aryl, alkyl, arylalkyl, cycloalkyl and heterocycle; R$_a$ and R$_b$ are each independently members selected from the group consisting of hydrogen, alkyl, arylalkyl and heterocyclealkyl and hydroxyalkyl; R$_d$ and R$_e$ are each independently members selected from the group consisting of hydrogen, alkyl, alkoxy, alkoxyalkyl, aryl, arylalkyl, halo, haloalkyl, heterocycle, heterocyclealkyl, hydroxy and hydroxyalkyl, and R$_d$ and R$_e$ taken together with the atom to which they are attached form cycloalkyl; and X is a member selected from the group consisting of —CH$_2$—, —CHF—, —CF$_2$—, —O—, and —S—.

According to another embodiment of the present invention there is provided a compound of formula (VIIa),

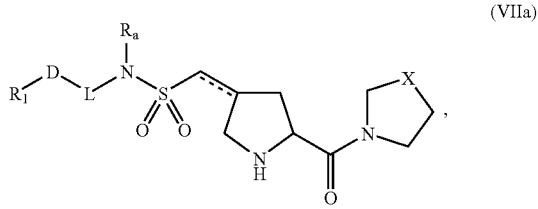

(VIIa)

or therapeutically suitable salt, ester or prodrug, thereof, wherein

is a member selected from the group consisting of a single and double bond; D is a bond or is a member selected from the group consisting of —C(O)—, —C(O)—N(R$_b$)—, —N(R$_b$)—, —N(R$_b$)—C(O)—, —N(R$_b$)—S(O)$_2$—, —O—, and —S(O)$_2$—N(R$_b$)—; L is a member selected from the group consisting of a bond, —(CH$_2$)$_m$—CR$_d$R$_e$—(CH$_2$)$_n$—, aryl, cycloalkyl, and heterocycle; m and n are each independently 0, 1, 2, 3 or 4; R$_1$ is a member selected from the group consisting of aryl, and heterocycle, wherein said aryl group and said heterocycle is further substituted with an aryl or a heterocyclic ring as defined herein; R$_a$ and R$_b$ are each independently members selected from the group consisting of hydrogen, alkyl, arylalkyl and heterocyclealkyl and hydroxyalkyl; R$_d$ and R$_e$ are each independently members selected from the group consisting of hydrogen, alkyl, alkoxy, alkoxyalkyl, aryl, arylalkyl, halo, haloalkyl, heterocycle, heterocyclealkyl, hydroxy and hydroxyalkyl, and R$_d$ and R$_e$ taken together with the atom to which they are attached form cycloalkyl; and X is a member selected from the group consisting of —CH$_2$—, —CHF—, —CF$_2$—, —O—, and —S—.

According to another embodiment of the present invention there is provided a compound of formula (VIIb),

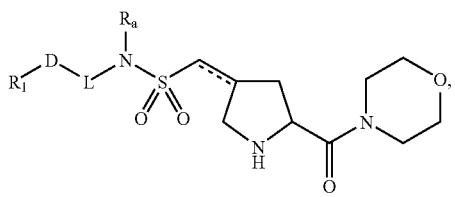

(VIIb)

or therapeutically suitable salt, ester or prodrug, thereof, wherein

is a member selected from the group consisting of a single and double bond; D is a bond or is a member selected from the group consisting of —C(O)—, —C(O)—N(R$_b$)—, —N(R$_b$)—, —N(R$_b$)—C(O)—, —N(R$_b$)—S(O)$_2$—, —O—, and —S(O)$_2$—N(R$_b$)—; L is a member selected from the group consisting of a bond, —(CH$_2$)$_m$—CR$_d$R$_e$—(CH$_2$)$_n$—, aryl, cycloalkyl, and heterocycle; m and n are each independently 0, 1, 2, 3 or 4; R$_1$ is a member selected from the group consisting of aryl, alkyl, arylalkyl, cycloalkyl and heterocycle; R$_a$ and R$_b$ are each independently members selected from the group consisting of hydrogen, alkyl, arylalkyl and heterocyclealkyl and hydroxyalkyl; and R$_d$ and R$_e$ are each independently members selected from the group consisting of hydrogen, alkyl, alkoxy, alkoxyalkyl, aryl, arylalkyl, halo, haloalkyl, heterocycle, heterocyclealkyl, hydroxy and hydroxyalkyl, and R$_d$ and R$_e$ taken together with the atom to which they are attached form cycloalkyl.

A method of inhibiting DPP-IV comprising administering a therapeutically effective amount of a compound of formula (I).

A method of inhibiting DPP-IV comprising administering a therapeutically effective amount of a compound of formula (II, IIa or IIb).

A method of inhibiting DPP-IV comprising administering a therapeutically effective amount of a compound of formula (III, IIIa or IIIb).

A method of inhibiting DPP-IV comprising administering a therapeutically effective amount of a compound of formula (IV, IVa or IVb).

A method of inhibiting DPP-IV comprising administering a therapeutically effective amount of a compound of formula (V, Va or Vb).

A method of inhibiting DPP-IV comprising administering a therapeutically effective amount of a compound of formula (VI, VIa or VIb).

A method of inhibiting DPP-IV comprising administering a therapeutically effective amount of a compound of formula (VII, VIIa or VIIb).

A method of treating disorders by inhibiting DPP-IV comprising administering a therapeutically effective amount of a compound of formula (I).

A method of treating disorders by inhibiting DPP-IV comprising administering a therapeutically effective amount of a compound of formula (II, IIa or IIb).

A method of treating disorders by inhibiting DPP-IV comprising administering a therapeutically effective amount of a compound of formula (III, IIIa or IIIb).

A method of treating disorders by inhibiting DPP-IV comprising administering a therapeutically effective amount of a compound of formula (IV, IVa or IVb).

A method of treating disorders by inhibiting DPP-IV comprising administering a therapeutically effective amount of a compound of formula (V, Va or Vb).

A method of treating disorders by inhibiting DPP-IV comprising administering a therapeutically effective amount of a compound of formula (VI, VIa or VIb).

A method of treating disorders by inhibiting DPP-IV comprising administering a therapeutically effective amount of a compound of formula (VII, VIIa or VIIb).

A method of treating diabetes, comprising administering a therapeutically effective amount of a compound of formula (I).

A method of treating diabetes, comprising administering a therapeutically effective amount of a compound of formula (II, IIa or IIb).

A method of treating diabetes, comprising administering a therapeutically effective amount of a compound of formula (III, IIIa or IIIb).

A method of treating diabetes, comprising administering a therapeutically effective amount of a compound of formula (IV, IVa or IVb).

A method of treating diabetes, comprising administering a therapeutically effective amount of a compound of formula (V, Va or Vb).

A method of treating diabetes, comprising administering a therapeutically effective amount of a compound of formula (VI, VIa or VIb).

A method of treating diabetes, comprising administering a therapeutically effective amount of a compound of formula (VII, VIIa or VIIb).

A method of treating type II diabetes, comprising administering a therapeutically effective amount of a compound of formula (I).

A method of treating type II diabetes, comprising administering a therapeutically effective amount of a compound of formula (II, IIa or IIb).

A method of treating type II diabetes, comprising administering a therapeutically effective amount of a compound of formula (III, IIIa or IIIb).

A method of treating type II diabetes, comprising administering a therapeutically effective amount of a compound of formula (IV, IVa or IVb).

A method of treating type II diabetes, comprising administering a therapeutically effective amount of a compound of formula (V, Va or Vb).

A method of treating type II diabetes, comprising administering a therapeutically effective amount of a compound of formula (VI, VIa or VIb).

A method of treating type II diabetes, comprising administering a therapeutically effective amount of a compound of formula (VII, VIIa or VIIb).

A method of treating hyperglycemia, comprising administering a therapeutically effective amount of a compound of formula (I).

A method of treating hyperglycemia, comprising administering a therapeutically effective amount of a compound of formula (II, IIa or IIb).

A method of treating hyperglycemia, comprising administering a therapeutically effective amount of a compound of formula (III, IIIa or IIIb).

A method of treating hyperglycemia, comprising administering a therapeutically effective amount of a compound of formula (IV, IVa or IVb).

A method of treating hyperglycemia, comprising administering a therapeutically effective amount of a compound of formula (V, Va or Vb).

A method of treating hyperglycemia, comprising administering a therapeutically effective amount of a compound of formula (VI, VIa or VIb).

A method of treating hyperglycemia, comprising administering a therapeutically effective amount of a compound of formula (VII, VIIa or VIIb).

A method of treating Syndrome X, comprising administering a therapeutically effective amount of a compound of formula (I).

A method of treating Syndrome X, comprising administering a therapeutically effective amount of a compound of formula (II, IIa or IIb).

A method of treating Syndrome X, comprising administering a therapeutically effective amount of a compound of formula (III, IIIa or IIIb).

A method of treating Syndrome X, comprising administering a therapeutically effective amount of a compound of formula (IV, IVa or IVb).

A method of treating Syndrome X, comprising administering a therapeutically effective amount of a compound of formula (V, Va or Vb).

A method of treating Syndrome X, comprising administering a therapeutically effective amount of a compound of formula (VI, VIa or VIb).

A method of treating Syndrome X, comprising administering a therapeutically effective amount of a compound of formula (VII, VIIa or VIIb).

A method of treating hyperinsulinemia, comprising administering a therapeutically effective amount of a compound of formula (I).

A method of treating hyperinsulinemia, comprising administering a therapeutically effective amount of a compound of formula (II, IIa or IIb).

A method of treating hyperinsulinemia, comprising administering a therapeutically effective amount of a compound of formula (III, IIIa or IIIb).

A method of treating hyperinsulinemia, comprising administering a therapeutically effective amount of a compound of formula (IV, IVa or IVb).

A method of treating hyperinsulinemia, comprising administering a therapeutically effective amount of a compound of formula (V, Va or Vb).

A method of treating hyperinsulinemia, comprising administering a therapeutically effective amount of a compound of formula (VI, VIa or VIb).

A method of treating hyperinsulinemia, comprising administering a therapeutically effective amount of a compound of formula (VII, VIIa or VIIb).

A method of treating obesity, comprising administering a therapeutically effective amount of a compound of formula (I).

A method of treating obesity, comprising administering a therapeutically effective amount of a compound of formula (II, IIa or IIb).

A method of treating obesity, comprising administering a therapeutically effective amount of a compound of formula (III, IIIa or IIIb).

A method of treating obesity, comprising administering a therapeutically effective amount of a compound of formula (IV, IVa or IVb).

A method of treating obesity, comprising administering a therapeutically effective amount of a compound of formula (V, Va or Vb).

A method of treating obesity, comprising administering a therapeutically effective amount of a compound of formula (VI, VIa or VIb).

A method of treating obesity, comprising administering a therapeutically effective amount of a compound of formula (VII, VIIa or VIIb).

A pharmaceutical composition comprising a therapeutically effective amount of a compound of formula (I) in combination with a pharmaceutically suitable carrier.

A pharmaceutical composition comprising a therapeutically effective amount of a compound of formula (II, IIa or IIb) in combination with a pharmaceutically suitable carrier.

A pharmaceutical composition comprising a therapeutically effective amount of a compound of formula (III, IIIa or IIIb) in combination with a pharmaceutically suitable carrier.

A pharmaceutical composition comprising a therapeutically effective amount of a compound of formula (IV, IVa or IVb) in combination with a pharmaceutically suitable carrier.

A pharmaceutical composition comprising a therapeutically effective amount of a compound of formula (V, Va or Vb) in combination with a pharmaceutically suitable carrier.

A pharmaceutical composition comprising a therapeutically effective amount of a compound of formula (VI, VIa or VIb) in combination with a pharmaceutically suitable carrier.

A pharmaceutical composition comprising a therapeutically effective amount of a compound of formula (VII, VIIa or VIIb) in combination with a pharmaceutically suitable carrier.

The present invention is also directed to a method of treating disorders mediated by DPP-IV through inhibition of enzymatic activity. Disorders known to be regulated through enzymatic activity are diabetes, especially type II diabetes, as well as hyperglycemia, Syndrome X, hyperinsulinemia, obesity, atherosclerosis, and various immunomodulatory diseases. Therefore, according to an embodiment of the present invention there are provided compounds of formula (I, II, IIa IIb, III, IIIa, IIIb, IV, IVa, IVb, V, Va, Vb, VI, VIa, VIb, VII, VIIa and VIIb), which are useful for the treatment of diabetes, especially type II diabetes, as well as hyperglycemia, Syndrome X, hyperinsulinemia, obesity, atherosclerosis, and various immunomodulatory diseases.

DEFINITIONS

As used throughout this specification and the appended claims, the following terms have the following meanings:

The term "alkenyl," as used herein, refers to a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy," as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl," as used herein, refers to an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl," as used herein, refers to an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl," as used herein, refers to an alkoxycarbonyl group, as defined herein, appended to the parent molecular moiety through a alkyl group, as defined herein.

The term "alkyl," as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl," as used herein, refers to an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy," as used herein, refers to an alkylcarbonyl group, as defined herein, appended to the parent molecular moiety through an oxygen atom, as defined herein.

The term "alkylsulfonyl," as used herein, refers to an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio," as used herein, refers to an alkyl group, as defined herein, appended to the parent molecular moiety through a sulfur atom.

The term "alkynyl," as used herein, refers to a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The alkynyl groups of this invention may be substituted with 0, 1, 2, or 3 substituents independently selected from alkoxy, alkoxyalkyl, alkoxycarbonyl, alkoxycarbonylalkyl, alkylcarbonyl, alkylcarbonylalkyl, heterocycle, heterocyclealkyl, hydroxy, and hydroxyalkyl.

The term "aryl," as used herein, refers to a monocyclic-ring system, or a bicyclic- or a tricyclic-fused ring system wherein one or more of the fused rings are aromatic. Representative examples of aryl include, but are not limited to, anthracenyl, azulenyl, fluorenyl, indanyl, indenyl, naphthyl, phenyl, and tetrahydronaphthyl.

The aryl groups of the present invention can be substituted with 0, 1, 2, or 3 substituents independently selected from alkyl, alkenyl, alkoxy, alkoxyalkyl, alkoxycarbonyl, alkoxycarbonylalkyl, alkyl, alkylcarbonyl, alkylcarbonyloxy, alkylsulfonyl, alkylthio, alkynyl, arylalkoxy, aryloxy, aryloxyalkyl, carboxy, carboxyalkyl, cyano, cyanoalkyl, formyl, halogen, haloalkyl, heterocycle, heterocyclealkyl, hydroxy, hydroxyalkyl, mercapto, nitro, perfluoroalkoxy, perfluoroalkyl, phenyl, $R_E R_F N-$, $R_G R_H NC(O)-$, and $R_G R_H NS(O)_2-$, wherein $R_E$ and $R_F$ are each independently selected from the group consisting of hydrogen, alkyl, alkylcarbonyl, alkoxycarbonyl, alkylsulfonyl, and $R_G$ and $R_H$ are each independently selected from the group consisting of hydrogen, alkyl, alkylcarbonyl and alkylsulfonyl.

The term "arylalkoxy," as used herein, refers to an aryl group, as defined herein, appended to the parent molecular moiety through an alkoxy group, as defined herein. Representative examples of arylalkoxy include, but are not limited to, 2-phenylethoxy, 3-naphth-2-ylpropoxy, and 5-phenylpentyloxy.

The term "arylalkyl," as used herein, refers to an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "arylcarbonyl," as used herein, refers to an aryl group, as defined herein, appended to the parent molecular moiety through a carbonyl group, as defined herein. Representative examples of arylcarbonyl include, but are not limited to, benzoyl and naphthoyl.

The term "aryloxy," as used herein, refers to an aryl group, as defined herein, appended to the parent molecular moiety through an oxy group, as defined herein.

The term "aryloxyalkyl," as used herein, refers to an aryloxy group, as defined herein, appended to the parent molecular moiety through an alkyl group, as defined herein.

The term "carbonyl," as used herein, refers to a $-C(O)-$ group.

The term "carboxy," as used herein, refers to a $-CO_2H$ group.

The term "cyano," as used herein, refers to a $-CN$ group.

The term "cyanoalkyl," as used herein, refers to a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "cycloalkyl," as used herein, refers to a monocyclic, bicyclic, or tricyclic ring system. Monocyclic ring systems are exemplified by a saturated cyclic hydrocarbon group containing from 3 to 8 carbon atoms. Examples of monocyclic ring systems include cyclopropyl, cyclobutyl, cyclopentyl, cyclohexyl, cycloheptyl, and cyclooctyl. Bicyclic ring systems are exemplified by a bridged monocyclic ring system in which two non-adjacent carbon atoms of the monocyclic ring are linked by an alkylene bridge of between one and three additional carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Tricyclic ring systems are exemplified by a bicyclic ring system in which two non-adjacent carbon atoms of the bicyclic ring are linked by a bond or an alkylene bridge of between one and three carbon atoms. Representative examples of tricyclic-ring systems include, but are not limited to, tricyclo[$3.3.1.0^{3,7}$]nonane and tricyclo[$3.3.1.1^{3,7}$]decane (adamantane).

The cycloalkyl groups of the present invention may be substituted with 0, 1, 2 or 3 substituents selected from alkyl, alkylcarbonyl, alkoxy, alkoxycarbonyl, alkenyl, alkynyl, aryl, aryloxy, aryloxyalkyl, cyano, halogen, hydroxy, hydroxyalkyl, nitro, $R_ER_FN$—, $R_GR_HNC(O)$—, and $R_GR_HNS(O)_2$—, wherein $R_E$ and $R_F$ are each independently selected from the group consisting of hydrogen, alkyl, alkylcarbonyl, alkoxycarbonyl, alkylsulfonyl and aryl, and $R_G$ and $R_H$ are each independently selected from the group consisting of hydrogen and alkyl.

The term "cycloalkylalkyl," as used herein, refers to a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "halo" or "halogen," as used herein, refers to —Cl, —Br, —I or —F.

The term "haloalkyl," as used herein, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "haloalkoxy," as used herein, refers to a haloalkyl group, as defined herein, appended to the parent molecular moiety through an oxygen atom.

The term "haloalkenyl," as used herein, refers to at least one halogen, as defined herein, appended to the parent molecular moiety through an alkenyl group, as defined herein. Representative examples of haloalkenyl include, but are not limited to, chloroethylenyl, 2-fluoroethylene, trifluorobutenyl, and dichloropropenyl.

The term "heterocycle" or "heterocyclic," as used herein, refers to a monocyclic, bicyclic, or tricyclic ring system. Monocyclic ring systems are exemplified by any 3 - or 4-membered ring containing a heteroatom independently selected from oxygen, nitrogen and sulfur; or a 5-, 6- or 7-membered ring containing one, two or three heteroatoms wherein the heteroatoms are independently selected from nitrogen, oxygen and sulfur. The 5-membered ring has from 0-2 double bonds and the 6- and 7-membered ring have from 0-3 double bonds. Representative examples of monocyclic ring systems include, but are not limited to, azetidinyl, azepanyl, aziridinyl, diazepinyl, 1,3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, piperidinyl, pyranyl, pyrazinyl, pyrazolyl, pyrazolinyl, pyrazolidinyl, pyridinyl, pyrimidinyl, pyridazinyl, pyrrolyl, pyrrolinyl, pyrrolidinyl, tetrahydrofuranyl, tetrahydrothienyl, tetrazinyl, tetrazolyl, thiadiazolyl, thiadiazolinyl, thiadiazolidinyl, thiazolyl, thiazolinyl, thiazolidinyl, thienyl, thiomorpholinyl, 1,1-dioxidothiomorpholinyl (thiomorpholine sulfone), thiopyranyl, triazinyl, triazolyl, and trithianyl. Bicyclic ring systems are exemplified by any of the above monocyclic ring systems fused to an aryl group as defined herein, a cycloalkyl group as defined herein, or another monocyclic ring system. Representative examples of bicyclic ring systems include but are not limited to, for example, benzimidazolyl, benzodioxinyl, benzothiazolyl, benzothienyl, benzotriazolyl, benzoxazolyl, benzofuranyl, benzopyranyl, benzothiopyranyl, cinnolinyl, indazolyl, indolyl, 2,3-dihydroindolyl, indolizinyl, naphthyridinyl, isobenzofuranyl, isobenzothienyl, isoindolyl, isoquinolinyl, phthalazinyl, 4H-pyrido[1,2-a]pyrimidin-4-one, pyranopyridinyl, quinolinyl, quinolizinyl, quinoxalinyl, quinazolinyl, tetrahydroisoquinolinyl, tetrahydroquinolinyl, and thiopyranopyridinyl. Tricyclic rings systems are exemplified by any of the above bicyclic ring systems fused to an aryl group as defined herein, a cycloalkyl group as defined herein, or a monocyclic ring system. Representative examples of tricyclic ring systems include, but are not limited to, acridinyl, carbazolyl, carbolinyl, dibenzo[b,d]furanyl, dibenzo[b,d]thienyl, naphtho[2,3-b]furan, naphtho[2,3-b]thienyl, phenazinyl, phenothiazinyl, phenoxazinyl, thianthrenyl, thioxanthenyl and xanthenyl.

According to the present invention, heterocycles may be substituted with 0, 1, 2 or 3 substituents independently selected from alkenyl, alkoxy, alkoxyalkyl, alkoxycarbonyl, alkoxycarbonylalkyl, alkyl, alkylcarbonyl, alkylcarbonylalkyl, alkylcarbonyloxy, alkylsulfonyl, alkylthio, alkynyl, aryl, arylalkoxy, aryloxyalkyl, arylalkyl, arylcarbonyl, aryloxy, carboxy, carboxyalkyl, cyano, cyanoalkyl, formyl, halogen, haloalkyl, a heterocycle ring, hydroxy, hydroxyalkyl, mercapto, nitro, oxo, phenyl, $R_ER_FN$—, $R_GR_HNC(O)$—, and $R_GR_HNS(O)_2$—, wherein $R_E$ and $R_F$ are each independently selected from the group consisting of hydrogen, alkyl, alkylcarbonyl, alkoxycarbonyl, alkylsulfonyl, and $R_G$ and $R_H$ are each independently selected from the group consisting of hydrogen and alkyl and wherein the heterocycle ring may be substituted with 0, 1 or 2 substituents independently selected from alkenyl, alkoxy, alkoxyalkyl, alkoxycarbonyl, alkoxycarbonylalkyl, alkyl, alkylcarbonyl, alkylcarbonylalkyl, alkylcarbonyloxy, alkylsulfonyl, alkylthio, alkynyl, aryl, arylalkoxy, arylalkyl, arylcarbonyl, aryloxy, carboxy, carboxyalkyl, cyano, cyanoalkyl, formyl, halogen, haloalkyl, hydroxy, hydroxyalkyl, mercapto, nitro and phenyl.

The term "heterocyclealkyl," as used herein, refers to a heterocycle, as defined herein, appended to the parent molecular moiety through an alkyl group, as defined herein. Representative examples of heterocyclealkyl include, but are not limited to, pyridin-3 -ylmethyl and 2-pyrimidin-2-ylpropyl and the like.

The term "hydroxy," as used herein, refers to an —OH group.

The term "hydroxyalkyl," as used herein, refers to a hydroxy group, as defined herein, appended to the parent molecular moiety through an alkyl group, as defined herein. Representative examples of hydroxyalkyl include, but are not limited to, 2-hydroxyethyl, 2-hydroxypropyl, 3-hydroxybutyl and the like.

The term "heterocyclecarbonyl," as used herein, refers to a heterocycle, as defined herein, appended to the parent molecular moiety through an carbonyl group, as defined herein. Representative examples of heterocyclecarbonyl include, but are not limited to, pyridin-3-ylcarbonyl and 2-pyrimidin-2-ylcarbonyl and the like.

The term "nitro," as used herein, refers to a —NO$_2$ group.

The term "perfluoroalkyl," as used herein, refers to an alkyl group that is exclusivly substituted with fluorine atoms.

The term "perfluoroalkoxy," as used herein, refers to an alkoxy group that exclusivly substituted with fluorine atoms.

The present compounds may exist as therapeutically suitable salts. The term "therapeutically suitable salt," refers to salts or zwitterions of the compounds which are water or oil-soluble or dispersible, suitable for treatment of disorders without undue toxicity, irritation, and allergic response, commensurate with a reasonable benefit/risk ratio, and effective for their intended use. The salts may be prepared during the final isolation and purification of the compounds or separately by reacting an amino group of the compounds with a suitable acid. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetic, trifluoroacetic, glutamate, para-toluenesulfonate, undecanoate, hydrochloric, hydrobromic, sulfuric, phosphoric, and the like. The amino groups of the compounds may also be quaternized with alkyl chlorides, bromides, and iodides such as methyl, ethyl, propyl, isopropyl, butyl, lauryl, myristyl, stearyl, and the like. The present invention contemplates pharmaceutically suitable salts formed at the nitrogen of formula (I, II, IIa, IIb, III, IIIa, IIIb, IV, IVa, IVb, V, Va, Vb, VI, VIa, VIb, VII, VIIa, and VIIb).

Basic addition salts may be prepared during the final isolation and purification of the present compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts derived from methylamine, dimethylamine, trimethylamine, triethylamine, diethylamine, ethylamine, tributlyamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine, ethylenediamine, ethanolamine, diethanolamine, piperidine, piperazine, and the like, are contemplated as being within the scope of the present invention.

The present compounds may also exist as therapeutically suitable prodrugs. The term "therapeutically suitable prodrug," refers to those prodrugs or zwitterions which are suitable for use in contact with the tissues of patients without undue toxicity, irritation, and allergic response, are commensurate with a reasonable benefit/risk ratio, and are effective for their intended use. The term "prodrug," refers to compounds that are rapidly transformed in vivo to the parent compounds of formula (I, II, IIa, IIb, III, IIIa, IIIb, IV, IVa, IVb, V, Va, Vb, VI, VIa, VIb, VII, VIIa, and VIIb) for example, by hydrolysis in blood.

Asymmetric centers may exist in the present compounds. Individual stereoisomers of the compounds are prepared by synthesis from chiral starting materials or by preparation of racemic mixtures and separation by conversion to a mixture of diastereomers followed by separation or recrystallization, chromatographic techniques, or direct separation of the enantiomers on chiral chromatographic columns. Starting materials of particular stereochemistry are either commercially available or are made by the methods described herein and resolved by techniques well-known in the art.

Geometric isomers may exist in the present compounds. The invention contemplates the various geometric isomers and mixtures thereof resulting from the disposal of substituents around a carbon-carbon double bond, a cycloalkyl group, or a heterocycloalkyl group. Substituents around a carbon-carbon double bond are designated as being of Z or E configuration and substituents around a cycloalkyl or heterocycloalkyl are designated as being of cis or trans configuration.

Therapeutic compositions of the present compounds comprise an effective amount of the same formulated with one or more therapeutically suitable excipients. The term "therapeutically suitable excipient," as used herein, represents a non-toxic, solid, semi-solid or liquid filler, diluent, encapsulating material, or formulation auxiliary of any type. Examples of therapeutically suitable excipients include sugars; cellulose and derivatives thereof; oils; glycols; solutions; buffering, coloring, releasing, coating, sweetening, flavoring, and perfuming agents; and the like. These therapeutic compositions may be administered parenterally, intracisternally, orally, rectally, or intraperitoneally.

Liquid dosage forms for oral administration of the present compounds comprise formulations of the same as emulsions, microemulsions, solutions, suspensions, syrups, and elixirs. In addition to the compounds, the liquid dosage forms may contain diluents and/or solubilizing or emulsifying agents. Besides inert diluents, the oral compositions may include wetting, emulsifying, sweetening, flavoring, and perfuming agents.

Injectable preparations of the present compounds comprise sterile, injectable, aqueous and oleaginous solutions, suspensions or emulsions, any of which may be optionally formulated with parenterally suitable diluents, dispersing, wetting, or suspending agents. These injectable preparations may be sterilized by filtration through a bacterial-retaining filter or formulated with sterilizing agents that dissolve or disperse in the injectable media.

Inhibition of DPP-IV by the compounds of the present invention may be delayed by using a liquid suspension of crystalline or amorphous material with poor water solubility. The rate of absorption of the compounds depends upon their rate of dissolution which, in turn, depends on their crystallinity. Delayed absorption of a parenterally administered compound may be accomplished by dissolving or suspending the compound in oil. Injectable depot forms of the compounds may also be prepared by microencapsulating the same in biodegradable polymers. Depending upon the ratio of compound to polymer and the nature of the polymer employed, the rate of release may be controlled. Depot injectable formulations are also prepared by entrapping the compounds in liposomes or microemulsions that are compatible with body tissues.

Solid dosage forms for oral administration of the present compounds include capsules, tablets, pills, powders, and granules. In such forms, the compound is mixed with at least one inert, therapeutically suitable excipient such as a carrier, filler, extender, disintegrating agent, solution retarding agent, wetting agent, absorbent, or lubricant. With capsules, tablets, and pills, the excipient may also contain buffering agents. Suppositories for rectal administration may be prepared by mixing the compounds with a suitable non-irritating excipient that is solid at ordinary temperature but fluid in the rectum.

The present compounds may be micro-encapsulated with one or more of the excipients discussed previously. The solid dosage forms of tablets, dragees, capsules, pills, and granules may be prepared with coatings and shells such as enteric and release-controlling. In these forms, the compounds may be mixed with at least one inert diluent and may optionally comprise tableting lubricants and aids. Capsules may also optionally contain opacifying agents that delay release of the compounds in a desired part of the intestinal tract.

Transdermal patches have the added advantage of providing controlled delivery of the present compounds to the body. Such dosage forms are prepared by dissolving or dispensing the compounds in the proper medium. Absorption enhancers may also be used to increase the flux of the compounds across the skin, and the rate of absorption may be controlled by providing a rate controlling membrane or by dispersing the compounds in a polymer matrix or gel.

Disorders that may be treated or prevented in a patient by administering to the patient, a therapeutically effective amount of compound of the present invention in such an amount and for such time as is necessary to achieve the desired result. The term "therapeutically effective amount," refers to a sufficient amount of a compound of formula (I, II, IIa IIb, III, IIIa, IIIb, IV, IVa, IVb, V, Va, Vb, VI, VIa, VIb, VII, VIIa, or VIIb) to effectively ameliorate disorders by inhibiting DPP-IV at a reasonable benefit/risk ratio applicable to any medical treatment. The specific therapeutically effective dose level for any particular patient will depend upon a variety of factors including the disorder being treated and the severity of the disorder; the activity of the compound employed; the specific composition employed; the age, body weight, general health, sex, and diet of the patient; the time of administration, route of administration, rate of excretion; the duration of the treatment; and drugs used in combination or coincidental therapy.

The total daily dose of the compounds of the present invention necessary to inhibit the action of DPP-IV in single or divided doses may be in amounts, for example, from about 0.01 to 50 mg/kg body weight. In a more preferred range, compounds of the present invention inhibit the action of DPP-IV in a single or divided doses from about 0.05 to 25 mg/kg body weight. Single dose compositions may contain such amounts or submultiple doses thereof of the compounds of the present invention to make up the daily dose. In general, treatment regimens comprise administration to a patient in need of such treatment from about 1 mg to about 1000 mg of the compounds per day in single or multiple doses.

Biological Data

Isolation of Rat DPP-IV

DPP-IV was purified to homogeneity (electrophoretic) from rat kidney as described in *Arch. Biochem. Biophy.* 1995, 323, 148-154. Rat kidney (120 g) was homogenized in 4 volumes of water and the homogenate centrifuged for 15 minutes at 1000 g. The pH of the supernatant was adjusted to 3.9 with 1 M HCl and the enzyme solubilized by autolysis for 18 hours at 37° C. The pH of the supernatant collected after centrifugation was adjusted to 7.2 with 1 M Trizma base and the enzyme was precipitated with $(NH_4)_2SO_4$ at 90% saturation (662 g solid ammonium sulfate per liter of solution). The solubilized precipitate was chromatographed on Sephadex G-200 (1 m×5 cm) equilibrated with a 10 mM Tris-HCl buffer pH 7.5 containing NaCl at a final concentration of 0.1 M and developed from the bottom. Fractions containing enzymatic activity were pooled, chromatographed on DE-52 (16×2.5 cm) equilibrated with 10 mM Tris-HCl, pH 7.5, and eluted with a 250-mL linear 0-0.4 M NaCl gradient prepared in 10 mM Tris-HCl. DPP-IV was then resolved from other brush border peptidases by chromatography on a phenyl Sepharose column (12×2 cm) equilibrated with 25% $(NH_4)_2SO_4$ at saturation (144 g ammonium sulfate per liter of 0.05 M Tris-HCl, pH 7.5). The enzyme was eluted in a homogeneous form with a 200-mL linear gradient of 25-0% $(NH_4)_2SO_4$, prepared in 0.05 M Tris HCl buffer.

Isolation of Human DPP-IV

Caco-2 cells were obtained from American Type Culture Collection (P.O. Box 3605, Manassas, Va.), cultured and maintained at 37° C. with 5% $CO_2$ in low glucose DMEM media supplemented with 10% Fetal Bovine Serum and antibiotic/antimycotic. In preparation for making an extract, cells were seeded at a density to achieve confluence within 7 days. The cells were cultured for an additional 14 days to allow for maximal DPPIV expression. On the day of harvest, cells were washed once with Dulbecco's PBS and solubilized in a 10 mM NaCl containing 50 mM Tris HCl, 0.5% Nonidet P40 and 0.3 ug/mL aprotinin at pH 8.0. The extract was clarified by centrifugation at 35,000 g for 30 minutes at 4° C. Human DPP-IV was purified from this extract supernatant, using precipitation with $(NH_4)_2SO_4$ at 90% saturation, as described for the rat DPP-IV. Human DPP-IV was purified from this solubilized precipitate by the same procedure as described for the solubilized precipitate of rat DPP-IV. The purified enzyme was stored frozen at −70° C. as drops collected in liquid nitrogen.

Inhibition Constant Determination for DPP-IV

DPP-IV activity was determined by measuring the rate of hydrolysis of a surrogate substrate Gly-Pro-7-amido-methylcoumarin (Gly-Pro-AMC, Catalogue #G-2761, Sigma, St. Louis, Mo.). The assay is carried out at room temperature in black 96 well polypropylene or polyethylene plates in a total volume of 100 µL per well. Appropriate dilutions of the compounds are made in DMSO and then diluted ten fold into water. 10 µL of 5 concentrations of the compound of formula (I, II, IIa, IIb, III, IIIa, IIIb, IV, IVa, IVb, V, Va, Vb, VI, VIa, VIb, VII, VIIa, and VIIb) (inhibitor) or 10% DMSO in water are added to individual wells containing 80 µL of DPP-IV diluted in assay buffer containing 25 mM HEPES (pH 7.5), 150 mM NaCl and 0.12 mg/mL BSA. After 10 minutes at room temperature, the reaction is initiated by adding 10 µL of either 280, 700, 1750, or 3500 µM Gly-Pro-AMC in water. The DPP-IV activity results in the formation of the fluorescent product amido-methylcoumarin (AMC) which is continuously monitored by excitation at 350 nm and measurement of fluorescent emission at 460 nm every 112 seconds for 37 minutes using an appropriate plate reader. The fluorescence at 460 nm is converted to nanomoles of AMC using a standard curve and the initial rate of AMC formation is calculated. For each concentration of each of the compounds of formula (I, II, IIa, IIb, III, IIIa, IIIb, IV, IVa, IVb, V, Va, Vb, VI, VIa, VIb, VII, VIIa, and VIIb) (inhibitor) or DMSO control, the initial rates are used to fit the rectangular hyperbola of Michaelis-Menten by non-linear regression analysis (GraphPad Software Prism 3.0). The ratio of the apparent Km/Vmax vs. inhibitor concentration is plotted and the competitive Ki is calculated by linear regression to be the negative x-intercept. The uncompetitve Ki is similarly calculated from the x-intercept of the plot of the reciprocal of the apparent Vmax versus the inhibitor concentration (Cornish-Bowden, A. 1995. Fundamentals of Enzyme Kinetics. Revised edition. Portland Press, Ltd., London, U.K.).

The compounds of the present invention were found to inhibit DPP-IV induced fluorescence with inhibitory constants in a range of about 0.0005 µM to about 7 µM. In a preferred range, the compounds of the present invention inhibited DPP-IV induced fluorescence with inhibitory constants in a range of about of about 0.0005 µM to about 1 µM; and in a more preferred range, the compounds of the present invention inhibited DPP-IV induced fluorescence with inhibitory constants in a range of about of about 0.0005 µM to about 0.5 µM.

As inhibitors of DPP-IV action, the compounds of the present invention are useful in treating disorders that are mediated by DPP-IV. Disorders that are mediated by DPP-IV include diabetes, type II diabetes, hyperglycemia, Syndrome X, hyperinsulinemia and obesity. Therefore the compounds of the present invention are useful in treating the disorder of diabetes, type II diabetes, hyperglycemia, Syndrome X, hyperinsulinemia and obesity.

Dipeptidyl-peptidase IV (DPP-IV, EC 3.4.14.5; CD26) is a post-proline cleaving serine protease with significant homology to other alpha-beta hydroxylases (e.g. prolyl oligopeptidase). DPP-IV is found throughout the body, both circulating in plasma and as a type II membrane protein produced by a variety of tissues, including kidney, liver and intestine. DPP-IV plays a role in the cleavage of specific substrates with accessible amino-terminal Xaa-Pro- or Xaa-Ala-dipeptide sequences, resulting in their inactivation or alteration in their biological activities. Important DPP-IV substrates include growth hormone releasing hormone, glucagon-like peptides GLP-1 and 2, gastric inhibitory polypeptide (GIP) and certain chemokines like RANTES (regulated on activation, normal T cell expressed and secreted), stromal cell-derived factor, eotaxin, and macrophage-derived chemokine (Mentlein, R. *Regulatory Peptides*, 1999, 85, 9-24).

The DPP-IV substrate, glucagon-like peptide GLP-1, is released from L cells in the distal small intestine and colon after oral ingestion of nutrients. The active GLP-1 (7-36) amide is an incretin that increases glucose stimulated insulin secretion (Drucker, D. J. *Diabetes,* 1998, 47, 159-169). Other activities attributed to GLP-1 (7-36) amide include stimulation of insulin gene expression, trophic effects on pancreatic beta cells, inhibition of glucagon secretion, promotion of satiety, inhibition of food intake, and slowing of gastric emptying (Drucker, D. J. *Diabetes,* 1998, 47, 159-169). These effects of GLP-1 (7-36) amide contribute to glucose homeostasis and the normalization of blood glucose levels in conditions of impaired glucose tolerance. In this regard, GLP-1 (7-36) amide has been demonstrated to reduce postprandial and fasting glycemia in patients with insulin-dependent and non-insulin-dependent diabetes mellitus (Nauck, et al., *Hormone Metab. Res.* 2002, 29, 411-416; Gutniak et al., *J. Internal Medicine,* 2001, 250, 81-87; Rauchman, et al., *Diabetologia.* 1997, 40, 205-11; Ahren, B., *BioEssays* 1998, 20, 642-51). GLP-1 based therapy has therapeutic potential for the treatment of type 2 diabetes. However, active GLP-1 (7-36) amide is rapidly converted to GLP-1 (9-36) amide by DPP-IV cleavage of the amino-terminal His-Ala- dipeptide of GLP-1 (7-36) amide (Mentlein, et al., *Eur. J. Biochem.* 1993, 214, 829-835). The resulting GLP-1 (9-36) amide is inactive and is an antagonist of the GLP-1 receptor (Knudson, et al., *Eur. J. Pharmacol.* 1996, 318, 429-35). The short half-life of GLP-1 (7-36) amide in the circulation (1-1.5 minutes) makes it impractical as a therapeutic agent and has led to the development of alternative strategies to enhance the anti-diabetogenic activity of GLP-1. One strategy is to increase the circulating half-life of GLP-1, by inhibiting DPP-IV activity (Deacon, et al., *Diabetes* 1995, 44 1126-31). Inhibition of DPP-IV in vivo increases the level of circulating GLP-1 (7-36) amide with a concomitant increase in its insulinotropic effect (Deacon, et al., *Diabetes.* 1998, 47, 764-9). A DPP-IV inhibitor has been demonstrated to improve glucose tolerance in non-insulin-dependent diabetes mellitus (Ahren B, et al., *Diabetes Care* 2002, 25, 869-875). Therefore, the compounds of the present invention, including but not limited to those specified in the examples may be used in the treatment of conditions caused by or associated with impaired glucose tolerance including the prevention or treatment of diabetes, especially non-insulin-dependent diabetes mellitus, hyperglycemia, hyperinsulinemia and metabolic syndrome (Johannsson, et al., *J. Endocrinol. Invest.* 1999, 22(5 Suppl), 41-6).

Striking similarities exist between the metabolic syndrome (syndrome X) and untreated growth hormone deficiency. Abdominal/visceral obesity and insulin resistance characterize both syndromes (Reaven, G M, *Physiol. Rev.* 1995, 75, 473-86; Johansson, et al., *Metabolism* 1995, 44, 1126-29). Growth hormone favorably effects some of the perturbations associated with abdominal/visceral obesity, including reduction in abdominal/visceral obesity, improved insulin sensitivity and lipoprotein metabolism and reduction in diastolic blood pressure (Barreto-Filho, et al., *J. Clin. Endocrinol. Metab.* 2002, 87(5), 2018-23; Colao et al., *J. Clin. Endocrinol. Metab.* 2002, 87(3), 1088-93; Gotherstrom, et al., *J. Clin. Endocrinol. Metab.* 2001, 86(10), 4657-65; Johannsson, et al., *J. Endocrinol. Invest.* 1999, 22(5 Suppl), 41-6; Johannsson, et al., *J. Clin. Endocrinol. Metab.* 1997, 82(3), 727-34).

For the treatment of diabetes or Syndrome X, compounds of the present invention may be used alone, or in combination with any existing anti-diabetic agent. Agents which may be used in combination with the compounds of the present invention include, but are not limited to insulin, an insulin analog such as mecasermin and the like, an insulin secretagogue such as nateglinide and the like, a biguanide such as metformin and the like, a sulfonylurea such as chlorpropamide, glipizide, glyburide, and the like, an insulin sensitizing agent such as a PPARγ agonist such as troglitazone, pioglitazone, rosiglitazone, and the like, an α-glucosidase inhibitor such as acarbose, voglibose, miglitol and the like, an aldose reductase inhibitor such as zopolrestat and the like, a metiglinide such as repaglinide and the like, a glycogen phosphorylase inhibitor, GLP-1 or a mimetic of GLP-1 such as exendin-4, or other such anti-diabetic agents that are known to one skilled in the art. The ability of the compounds of the present invention to treat diabetes, alone or in combination with another agent, may be demonstrated according to the methods described by Zander, M.; Mustafa, T.; Toft-Nielsen, M.-B.; Madsbad, S.; Holst, J. J. in *Diabetes Care* 2001, 24, 720-725; or, according to the methods described herein.

DPP-IV-mediated proteolysis has been established as a major route of growth hormone releasing hormone (GHRH) degradation and inactivation (Kubiak, et al., *Drug Metab. Dispos.* 1989, 17, 393-7). GHRH-derivatives that are resistant to DPP-IV cleavage are more potent in increasing serum growth hormone levels when administered i.v. due to longer stability in vivo. DPP-IV inhibition would be predicted to increase GHRH levels and thus serum growth hormone levels. Therefore, the compounds of the present invention, including but not limited to those specified in the examples may be used in the treatment of conditions associated with deficiency in growth hormone including metabolic disorders (central obesity, dyslipidemia), osteoporosis and frailty of aging.

Diabetic dyslipidemia is characterized by multiple lipoprotein defects including moderately high serum levels of cholesterol and triglycerides, small LDL particles and low levels of HDL cholesterol. The dyslipidemia associated with non-insulin-dependent diabetes mellitus is improved in conjunction with improved diabetic condition following treatment with GLP-1 (Junti-Berggren, et al., *Diabetes Care* 1996, 19, 1200-6). DPP-IV inhibition is predicted to increase the level of circulating GLP-1 (7-36) amide and thereby would be effective in the treatment of diabetic dyslipidemia and associated complications. Therefore, the compounds of the present invention, including but not limited to those specified in the examples may be used in the treatment of hypercholesterolemia, hypertriglyceridemia and associated cardiovascular disease.

Parenteral injection of GLP-1 (7-36) amide in healthy men, obese men or patients with non-insulin-dependent diabetes mellitus has been reported to promote satiety and to suppress food intake (Flint, et al., *J. Clin. Invest.* 1998, 101, 515-520; Naslund, et al., *Am. J. Clin. Nutr.* 1998, 68, 525-530; Gutzwiller, et al., *Am. J. Physiol.* 1999, 276, R1541-R1544.) DPP-IV inhibition is predicted to increase the level of circulating GLP-1 (7-36) amide and thereby increases satiety in obesity and non-insulin-dependent diabetes mellitus. Therefore, the compounds of the present invention, including but not limited to those specified in the examples may be used in the treatment of obesity.

For the treatment of obesity, compounds of the present invention may be used alone, or in combination with any existing anti-obesity agent as described by Flint, A.; Raben, A.; Astrup, A.; Holst, J. J. in *J. Clin. Invest.* 1998, 101, 515-520 or by Toft-Nielsen, M.-B.; Madsbad, S.; Holst, J. J. in *Diabetes Care* 1999, 22, 1137-1143. Agents which may be used in combination with the compounds of the present invention include, but are not limited to fatty acid uptake inhibitors such as orlistat and the like, monoamine reuptake inhibitors such as sibutramine and the like, anorectic agents such as dexfenfluramine, bromocryptine, and the like, sympathomimetics such as phentermine, phendimetrazine, mazindol, and the like, thyromimetic agents, or other such anti-obesity agents that are known to one skilled in the art.

DPP-IV is expressed on a fraction of resting T cells at low density but is strongly upregulated following T-cell activation. DPP-IV may have important functions on T cells and in the immune system. Synthetic inhibitors of the enzymatic activity of CD26 have been shown to suppress certain immune reactions in vitro and in vivo. In vitro recombinant soluble DPP-IV enhances proliferative responses of peripheral blood lymphocytes to stimulation with soluble tetanus toxoid antigen. In addition, the enhancing effect requires DPP-IV enzyme activity (Tanaka, et al., *Proc. Natl. Acad. Sci.* 1994, 91, 3082-86; Tanaka, et al., *Proc. Natl. Acad. Sci.* 1993, 90, 4583). Soluble DPP-IV up-regulates the expression of the costimulatory molecule CD86 on monocytes through its dipeptidyl peptidase IV activity suggesting that soluble DPP-IV enhances T cell immune response to recall antigen via its direct effect on antigen presenting cells (Ohnuma, et al., *J. Immunol.* 2001, 167(12), 6745-55). Consequently, DPP-IV inhibition would be predicted to suppress certain immune responses and thus have therapeutic benefit in the treatment of immunomodulatory diseases. Therefore, the compounds of the present invention, including but not limited to those specified in the examples may be used in the treatment of rheumatoid arthritis, multiple sclerosis, scleraderma, chronic inflammatory bowel disease or syndrome and allograft rejection in transplantation.

Chemokine receptors, especially CCR5 and CXCR4, act as cofactors for HIV-1 entry into CD4+ cells and their corresponding ligands may suppress HIV entry and thus replication. The CXC chemokine, stromal cell derived factor-1 (SDF-1) is a chemokine for resting T-lymphocytes and monocytes. SDF-1 exists as two splice variants, SDF-1alpha and SDF-1beta that differ by four additional C-terminal residues in SDF-1beta. Truncation of the N-terminal Lys-Pro-residues from both SDF-1 alpha and SDF-1 beta results in the loss of their chemotactic and antiviral activities in vitro (Ohtsuki, et al, *FEBS Lett.* 1998, 431, 236-40; Shioda, et al., *Proc. Natl. Acad. Sci.* 1998, 95(11), 6331-6; Proost, et al., *FEBS Lett.* 1998, 432, 73-6). DPP-IV inactivates SDF-1 alpha as a ligand for CXCR4 that is a T cell chemotactic receptor as well as the major co-receptor for T-tropic HIV-1 strains. DPP-IV inhibition would be predicted to increase full-length SDF-1 levels and thereby suppress HIV-1 entry into CXCR4+ cells. Therefore, the compounds of the present invention, including but not limited to those specified in the examples may be used in the treatment of HIV infection (AIDS).

Synthetic Methods

The compounds and processes of the present invention will be better understood in connection with the following synthetic schemes which together illustrate the methods by which the compounds of the invention may be prepared. The synthesis of compounds of formula (I, II, IIa, IIb, III, IIIa, IIIb, IV, IVa, IVb, V, Va, Vb, VI, VIa, VIb, VII, VIIa, and VIIb) wherein the groups $R_1$, D, L, B, A and X are as defined above unless otherwise noted below, are exemplified below.

Abbreviations which have been used in the descriptions of the scheme and the examples that follow are: DMA for dimethylacetamide; DAST for (diethylamino)sulfur trifluoride; DMAP for 4-(dimethylamino)pyridine; DMSO for dimethylsulfoxide; NMP for N-methylpyrrolidinone; DMF for N,N-dimethylformamide; DCC for 1,3-dicyclohexylcarbodiimide, DIC for 2-dimethylaminoisopropyl chloride hydrochloride; EDCI for 1-(3-dimethylaminopropyl)-3-ethylcarbodiimide hydrochloride; HATU for O-(7-azabenzotriazol-1-yl)-N, N, N', N'-tetramethyluronium hexafluorophosphate; HBTU for O-benzotriazole-1-yl-N, N, N', N'-tetramethyluronium hexafluorophosphate; HOAt for 1-hydroxy-7-azabenzotriazole; HOBt for 1-hydroxybenzotriazole hydrate; MP for macroporous; Ms for methanesulfonyl; RP-HPLC for reverse phase high pressure liquid chromatography; TBTU for 2-(1H-benzotriazol-1-yl)-1,1,3,3-tetramethyluronium tetrafluoroborate; TFA for trifluoroacetic acid; THF for tetrahydrofuran; and PS for polymer supported.

The compounds and processes of the present invention will be better understood in connection with the following synthetic schemes which together illustrate the methods by which the compounds of the invention may be prepared. Compounds of the present invention, may be made through the these Schemes or through similar methods conducted by one skilled in the art.

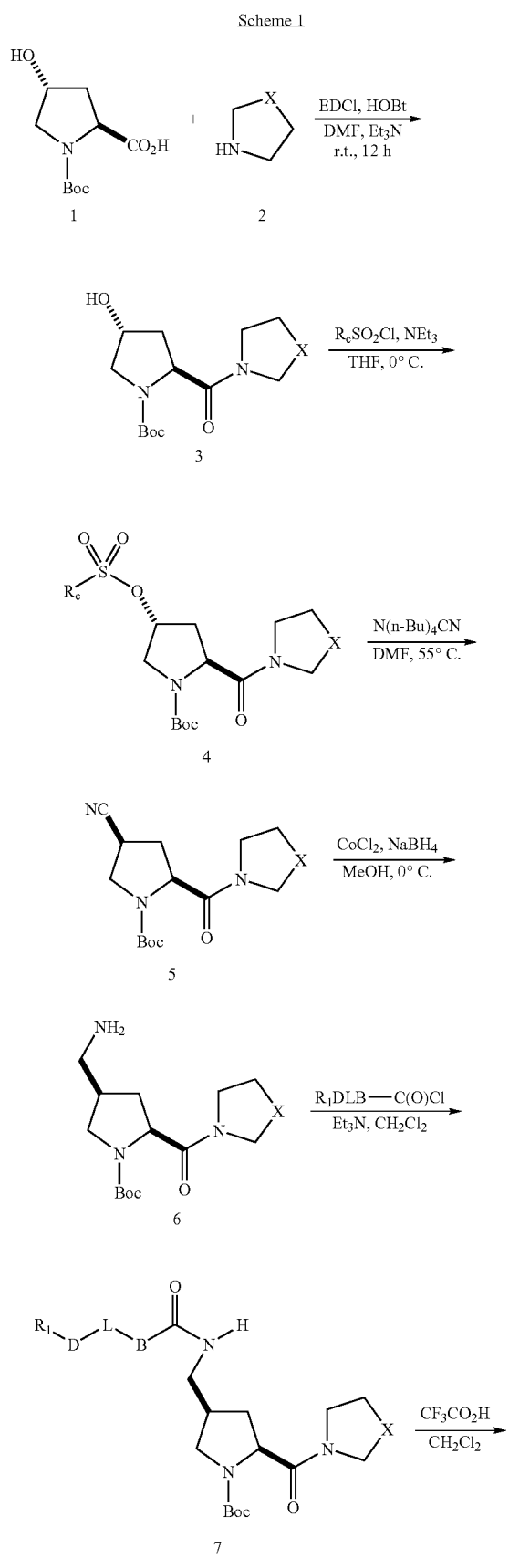

As shown in Scheme 1, compounds of formula 1 when treated with compounds of formula 2 in the presence of coupling reagents such as but not limited to EDCI, DCC, DIC, HATU, HBTU, an auxiliary nucleophile such as but not limited to HOBt and HOAt and a base such as but not limited to diisopropylethylamine, triethylamine, N-methylmorpholine in solvents such as but not limited to N,N-dimethylformamide and methylene chloride, will provide compounds of formula 3. Compounds of formula 3 when treated with reagents of formula $R_cSO_2$—Cl (wherein $R_c$ is a member selected from the group consisting of methyl, p-toluene, and phenyl) which are selected from the group consisting of methanesulfonyl chloride, para-toluenesulfonyl chloride and benzenesulfonyl chloride in the presence of triethylamine in solvents such as THF or dichloromethane will provide mesylates, tolsylates or bezylates of formula 4. The treatment of compounds of formula 4 which contain a mesylate, tosylate or besylate with reagents such as tetrabutylammonium cyanide in solvents like DMF under heated condtions or sodium cyanide in DMF or DMSO will provide compounds of formula 5. Nitrile compounds of formula 5 may be reduced using conditions known to those skilled in the art such as but not limited to cobalt chloride, sodium borohydride in alcoholic solvents such as methanol or ethanol to provide amines of formula 6. Other conditions useful for the reduction of the nitrile group to the amine include subjecting compounds of formula 5 to an atmosphere of hydrogen in the presence of Raney-nickel in methanolic ammonia. Compounds of formula 6 when treated with acid chlorides of formula $R_1DLB$-C(O)—Cl and a base such as but not limited to triethylaamine and N-methylmorpholine in solvents such as but not limited to dichloromethane will provide compounds of formula 7. Compounds of formula 7 when treated with trifluoroacetic acid in dichloromethane or hydrochloric acid in acetic acid or dioxane will provide compounds of formula 8 which are representative of compounds of the present invention. Alternatively, compounds of formula 7 may be treated with other conditions known to those skilled in the art or demonstrated in Greene, T. W. and Wuts, G. M. "Protective groups in Organic Synthesis", third ed. John Wiley & Sons, 1999, that will deprotect a tert-butyl oxycarbonyl group that is used as a nitrogen protecting group to provide compounds of formula 8.

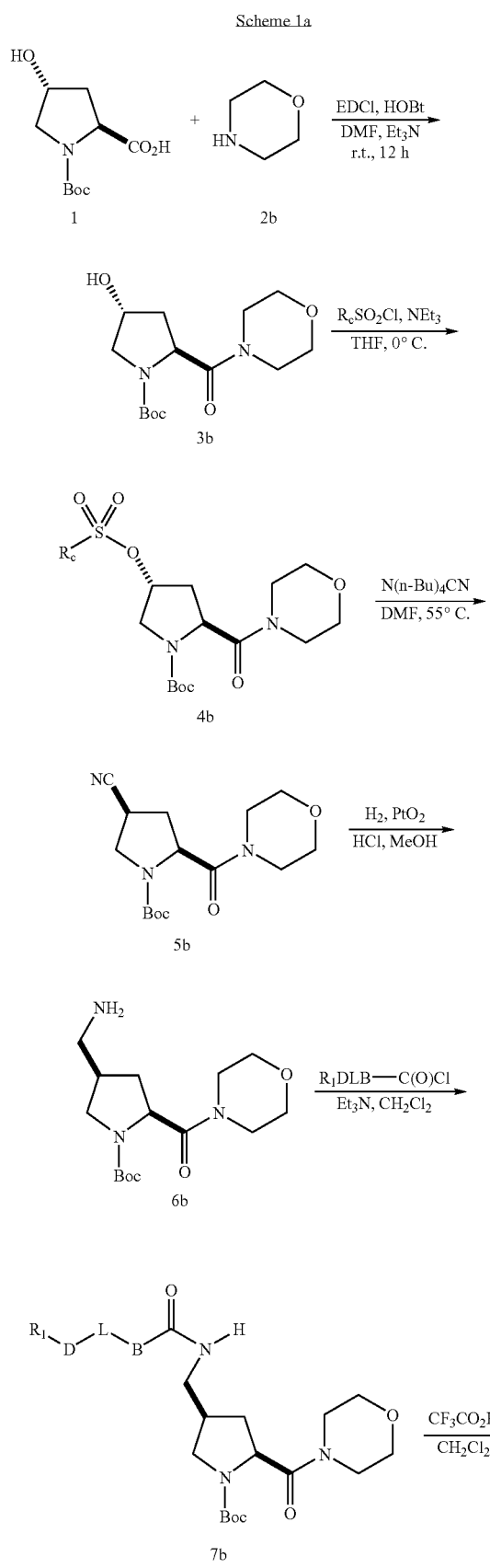

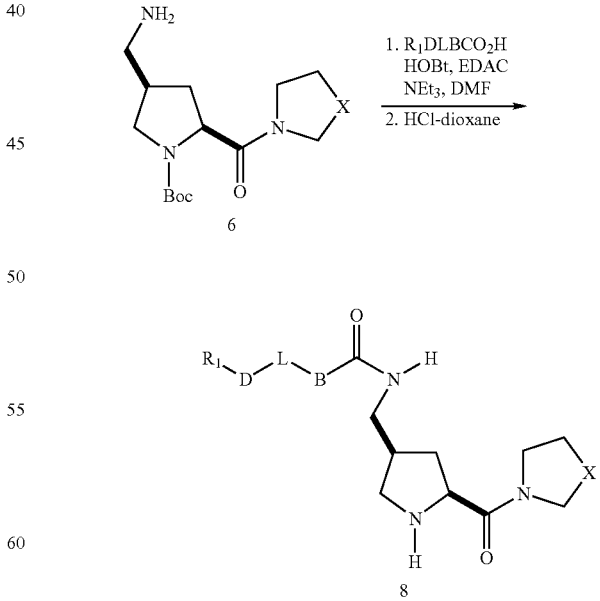

-continued

Alternatively, compounds of formula 1 may be treated according to conditions outlined in Scheme 1a substituting compounds of formula 2 with compounds of formula 2b to provide compounds of formula 3b. Compounds of formula 3b when treated with $R_cSO_2Cl$ (wherein $R_c$ is defined above) and triethylamine in THF followed by treatment with tetrabutylammonium cyanide in DMF as outlined in Scheme 1 will provide compounds of formula 5b. Compounds of formula 5b when subjected to catalytic hydrogenation conditions known to those skilled in the art will provide compounds of formula 6b. Compounds of formula 6b when treated with $R_1DLB-C(O)Cl$ and triethylamine in dichloromethane followed by trifluoroacetic acid in dichloromethane known to those skilled in the art to effect tert-butyloxycarbonyl deprotection as outlined in Scheme 1 will provide compounds of formula 8b, which are representative of compounds of the present invention.

Similarly, compound of formula 6 when treated with carboxylic acids of formula $R_1DLB-CO_2H$, coupling reagents such as but not limited to EDCI, DCC, DIC, HATU, HBTU, an auxiliary nucleophile such as but not limited to HOBt and HOAt and a base such as but not limited to diisopropylethylamine, triethylamine, N-methylmorpholine in solvents such as but not limited to N,N-dimethylformamide and methylene chloride to provide a compound that when deprotected using hydrochloric acid in dioxane will provide compounds of formula 8 which are representative of compounds of the present invention.

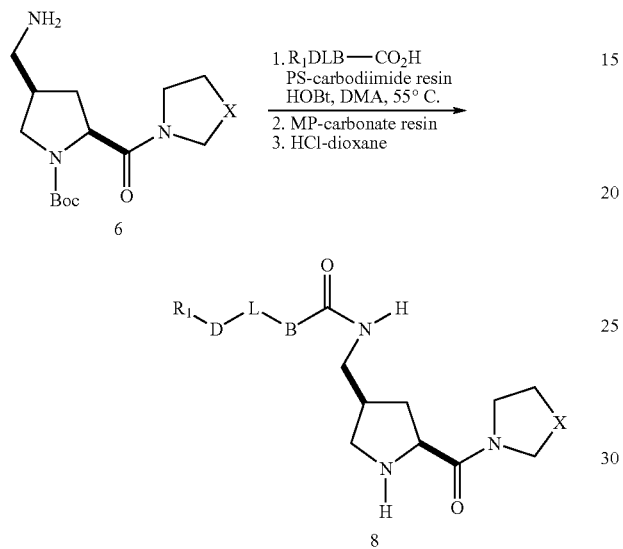

Furthermore, compounds of formula 6 may be utilizes as a combinatorial synthetic core useful for generating libraries of compounds of formula 8 which are representative of the compounds of the present invention.

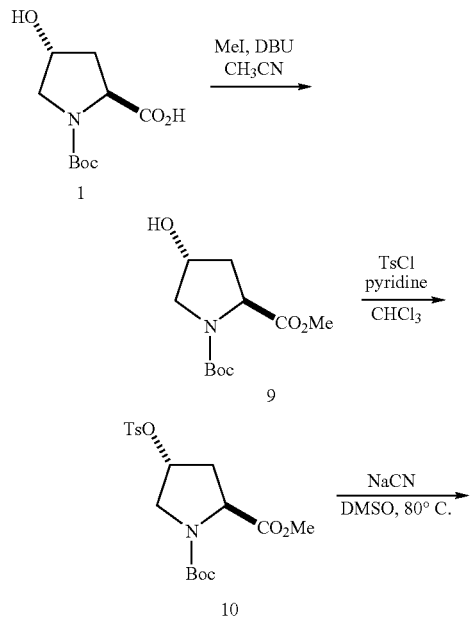

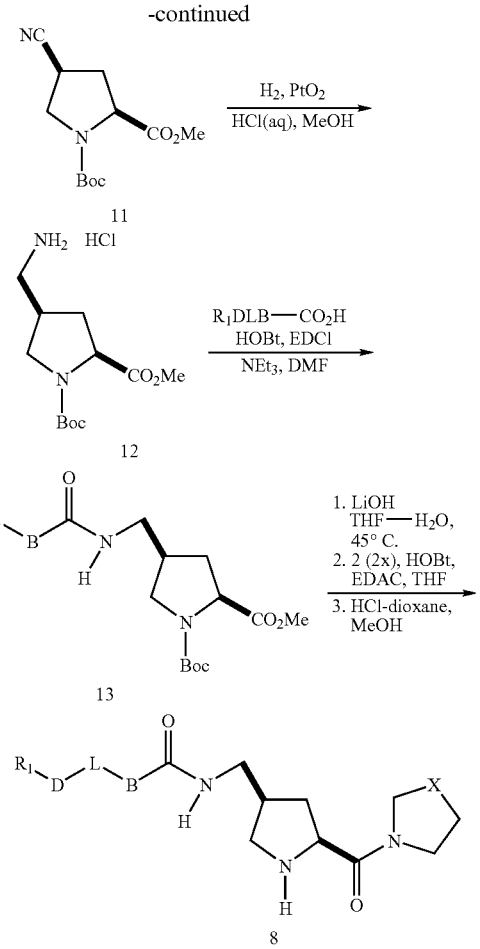

As shown in Scheme 4, compounds of formula 1 when treated with methyl iodide in the presence of DBU (1,8-diazabicyclo[5.4.0]undec-7-ene) in acetonitrile will provide compounds of formula 9. The alcohol group of compounds of formula 9 when treated with TsCl (p-toluenesulfonyl chloride) in the presence of pyridine and a solvent such as but not limited to chloroform will provide a compound of formula 10. Compound of formula 10 when treated with sodium cyanide in DMSO (dimethyl sulfoxide) under heated conditions will provide compounds of formula 11. Compounds of formula 11 when treated with an atmosphere of hydrogen in the presence of platinum oxide in a solvent such as but not limited to methanol containing aqueous hydrochloric acid will provide amines of formula 12. The amine functionality of compound of formula 12 when treated with a carboxylic acid of formula $R_1DLB\text{-}CO_2H$ in the presence of coupling reagents such as but not limited to EDCI, DCC, DIC, HATU, HBTU, an auxiliary nucleophile such as but not limited to HOBt and HOAt and a base such as but not limited to diisopropylethylamine, triethylamine, N-methylmorpholine in solvents such as but not limited to N,N-dimethylformamide and methylene chloride, will provide compounds of formula 13. Compounds of formula 13 when treated with lithium hydroxide in an aqueous solution such as but not limited to aqueous THF, or aqueous isopropanol under slight heating conditions will hydrolize the ester of the carboxylic acid. The carboxylic acid when treated with compounds of formula 2 in the presence of coupling reagents such as but not limited to EDCI, an auxiliary nucleophile such as HOBt in solvents such as but not limited to THF will provide compounds which when subjected to BOC deprotecting conditions will provide compounds of formula 8 which are representative of compounds of the present invention.

Scheme 5

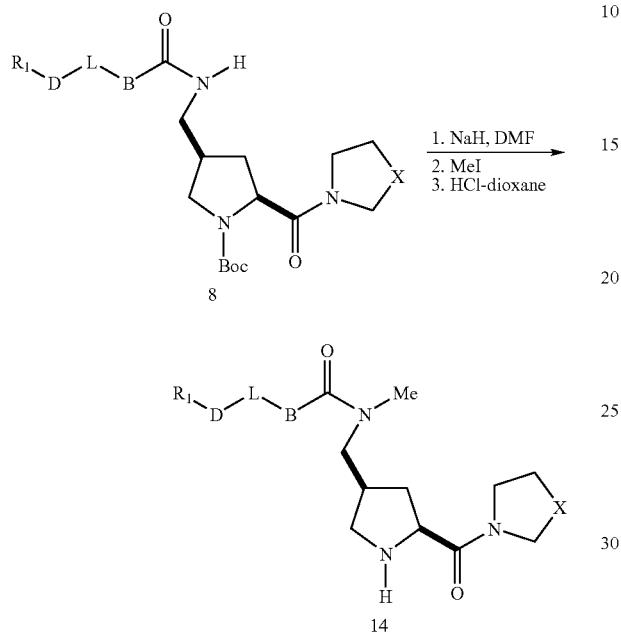

As shown in Scheme 5, compounds of formula 8 when subjected to sodium hydride in DMF followed by the addition of methyl iodide will provide an N-methylated compound which when subjected to Boc deprotecting conditions previously mentioned will provide compounds of formula 14 which are representative of the compounds of the present invention.

Scheme 6

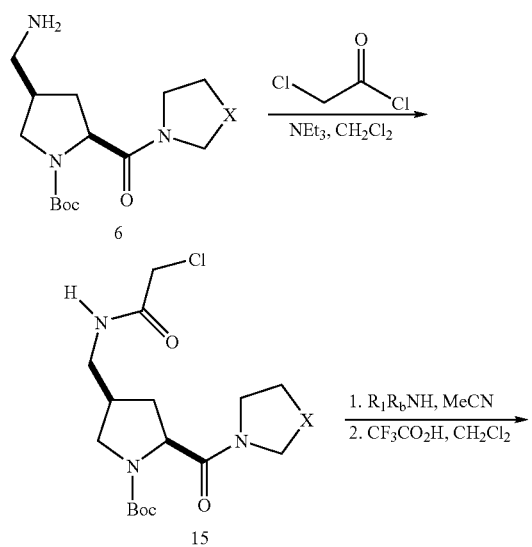

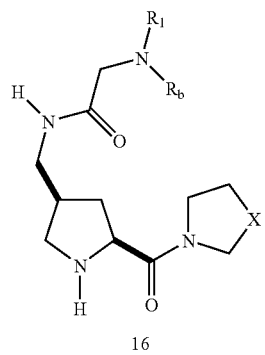

As shown in Scheme 6, compounds of formula 6 when treated with chloroacetyl chloride and triethylamine in dichloromethane will provide compounds of formula 15. Compounds of formula 15 when treated with amines of formula $R_1R_bNH$ (wherein $R_1$ and $R_b$ are defined within the scope of this invention) in acetonitrile will provide an amine which when treated to conditions known to deprotect Boc protecting groups as was previously discussed will provide compounds of formula 16 which are representative of the compounds of the present invention.

Scheme 7

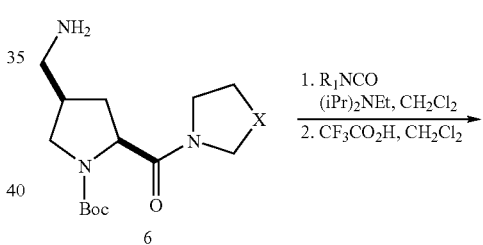

As shown in Scheme 7, compounds of formula 6 when treated with compounds of formula $R_1NCO$, in the presence of a base such as but not limited to diisopropylethylamine in dichloromethane will provide ureas that when treated with reagents known to deprotect Boc protecting groups such as but not limited to trifluoroacetic acid in dichloromethane, will provide compounds of formula 16 which are representative of the compounds of the present invention.

Scheme 8

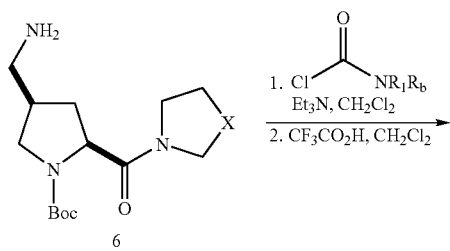

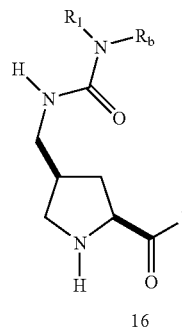

Scheme 9

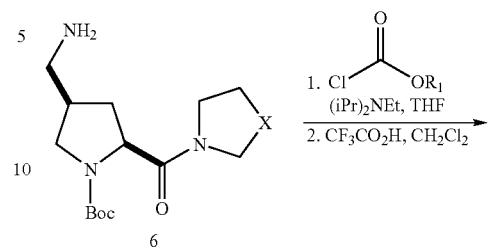

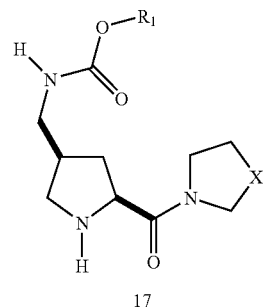

Alternatively, as shown in Scheme 8, compounds of formula 6 when treated with compounds of formula R₁R_bNC(O)Cl in the presence of a base such as but not limited to triethylamine in dichloromethane will also provide ureas that when treated with reagents known to deprotect Boc protecting groups such as but not limited to trifluoroacetic acid in dichloromethane, will provide compounds of formula 16 which are representative of the compounds of the present invention.

As shown in Scheme 9, compounds of formula 6 when treated with compounds of formula R₁OC(O)Cl in the presence of a base such as but not limited to diisopropylethylamine in THF will provide a carbamate that when treated to conditions known to deprotect Boc protecting groups such as but not limited to trifluoroacetic acid in dichloromethane, will provide compounds of formula 17 which are representative of the compounds of the present invention.

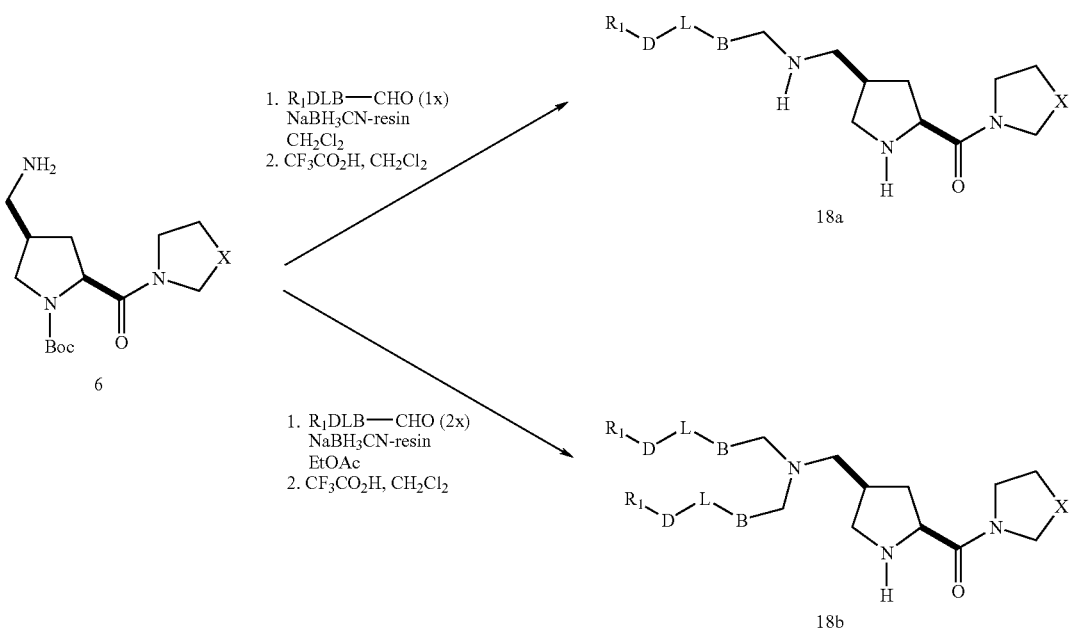

As shown in Scheme 10, compounds of formula 6 when treated with either 1 or 2 equivalents of aldehydes of formula $R_1DLB\text{-}CHO$ under reductive amination conditions will provide the monoalkylated or dialkylated product which when subjected to Boc deprotecting conditions will provide compounds of formula 18a or 18b which are representative of compounds of the present invention.

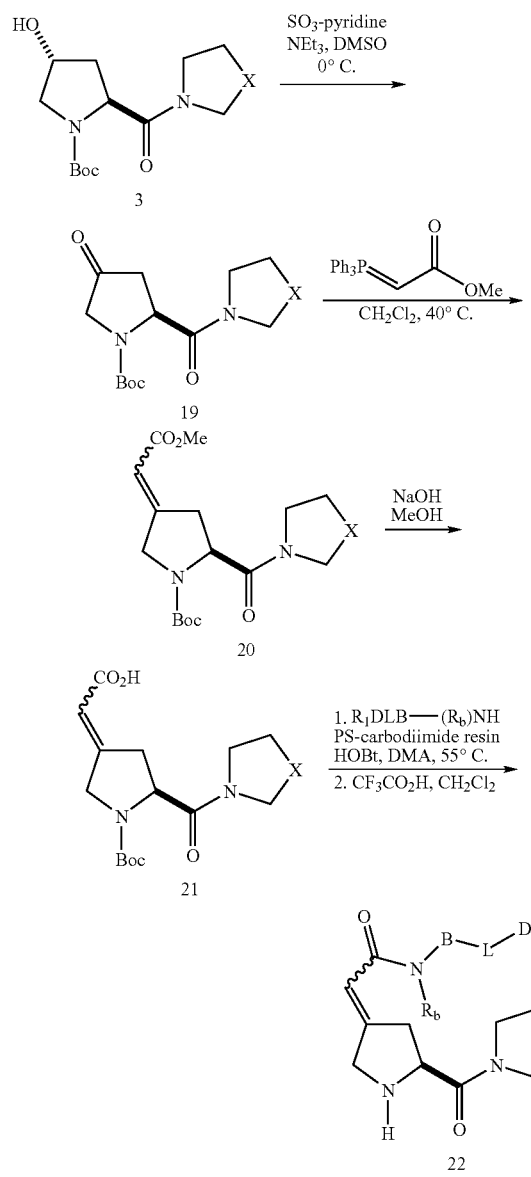

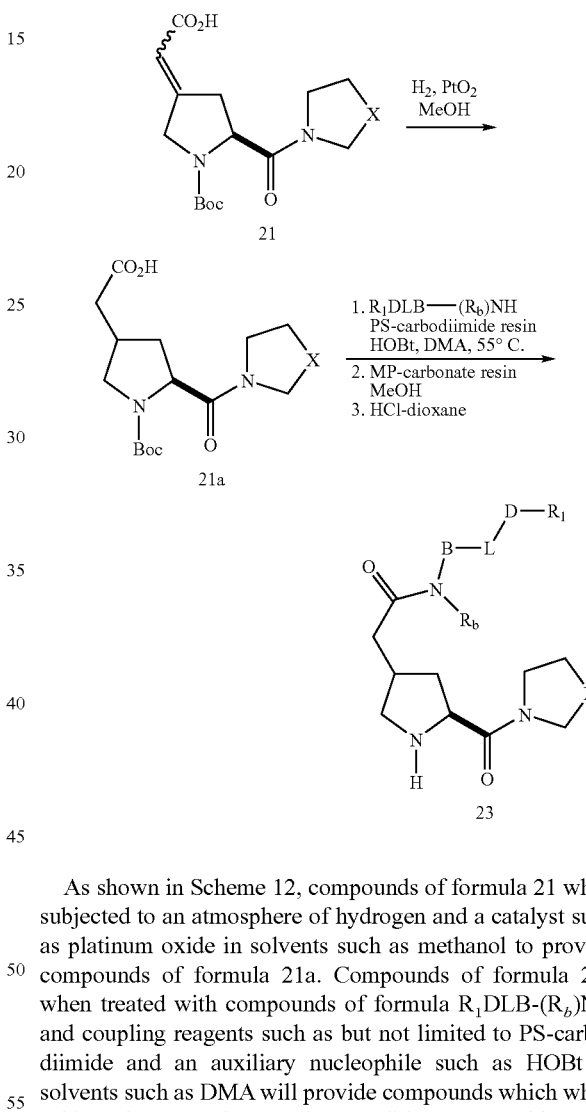

known to those skilled in the art such as but not limited to sodium hydroxide in aqueous methanol will provide compounds of formula 21. Compounds of formula 21 when treated with compounds of formula $R_1DLB\text{-}(R_b)NH$ and a coupling reagent such as but not limited to PS-carbodiimide and an auxiliary nucleophile such as HOBt in solvents such as DMA will provide compounds which when subjected to Boc deprotecting conditions to provide compounds of formula 22 which are representative of the present invention.

As shown in Scheme 11, compounds of formula 3 when treated with sulfur trioxide pyridine complex in the presence of triethylamine in DMSO at cooled temperatures will provide ketones of formula 19. Alternatively, other oxidizing conditions may be utilized in the conversion of compounds of formula 3 to compounds of formula 19 as would be known to those skilled in the art. Compounds of formula 19 when treated with methyl (triphenylphosphoranylidene) acetate in dichloromethane under heated conditions will provide compounds of formula 20. Compounds of formula 20 when subjected to conditions that will hydrolize esters as As shown in Scheme 12, compounds of formula 21 when subjected to an atmosphere of hydrogen and a catalyst such as platinum oxide in solvents such as methanol to provide compounds of formula 21a. Compounds of formula 21a when treated with compounds of formula $R_1DLB\text{-}(R_b)NH$ and coupling reagents such as but not limited to PS-carbodiimide and an auxiliary nucleophile such as HOBt in solvents such as DMA will provide compounds which when subjected to Boc deprotecting conditions to provide compounds of formula 23 which are representative of the present invention.

Scheme 13

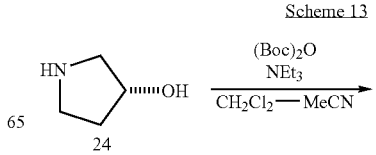

24

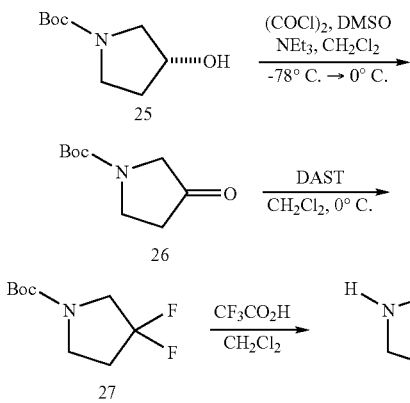

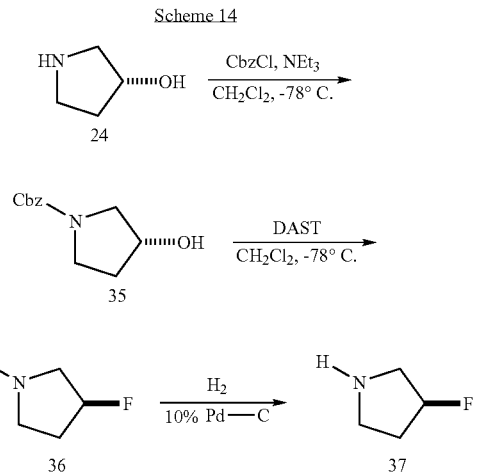

As shown in Scheme 13, compounds of formula 25 when treated under oxidative conditions of oxalyl chloride in DMSO followed by the addition of triethylamine will provide the ketone of formula 26. The ketone of formula 26 when treated with DAST ((diethylamino)sulfur trifluoride) in dichloromethane will provide difluoro compounds of formula 27. The Boc group of compounds of formula 27 may be removed using trifluoroacetic acid in dichloromethane to provide compounds of formula 28.

Similarily, compounds of formula 35 which contain an alcohol when treated with DAST followed by conditions known to remove Cbz protecting groups will provide compounds of formula 37. Both compounds of formula 28 and 37 may be subjected to the synthetic Schemes listed above to generate compounds of the present invention that contain a mono- or difluoropyrrolidine.

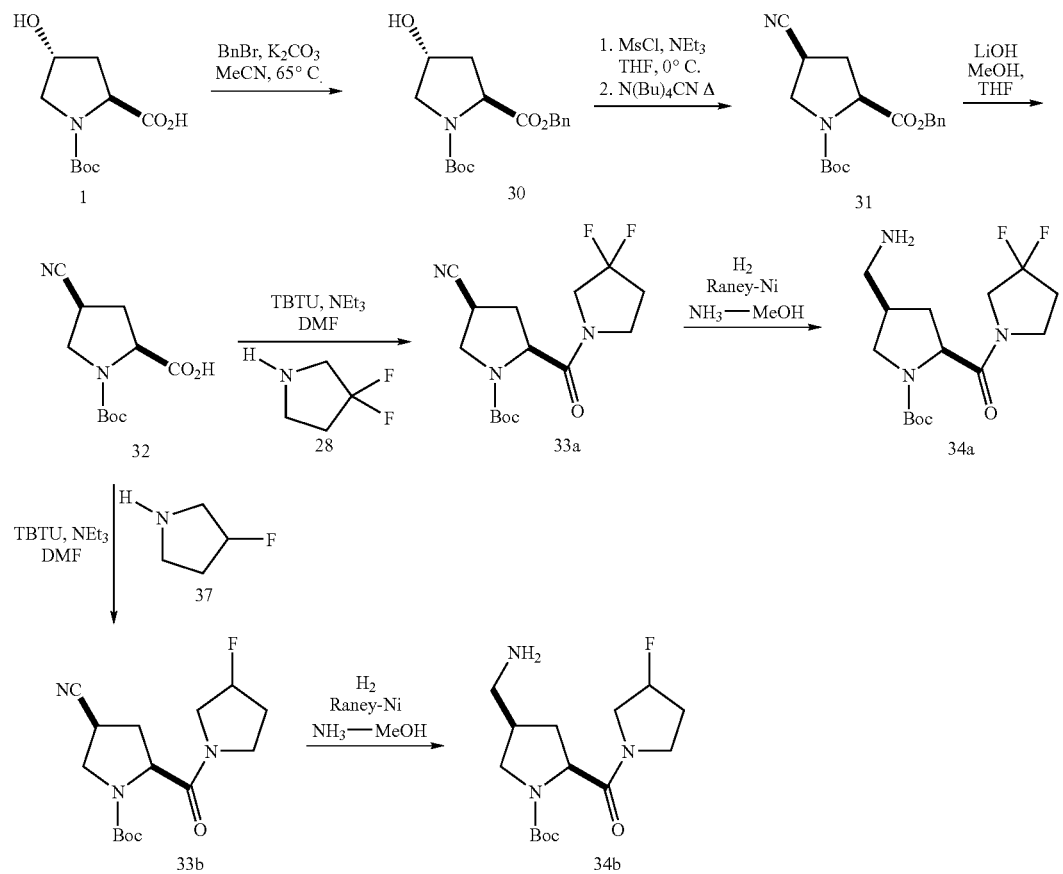

As shown in Scheme 15, compounds of formula 32 may be treated with compounds of formula 28 or 37 in the presence of TBTU and a base such as triethylamine in solvents such as but not limited to DMF to provide compounds of formula 33a and 33b. Compounds of formula 33a or compounds of formula 33b when treated to an atmosphere of hydrogen and Raney-Nickel in methanolic ammonia will provide compounds of formula 34a and compounds of formula 34b, respectively. Compounds of 34a and compounds of formula 34b when subjected to conditions described by Schemes listed above will provide compounds representative of the present invention which contain a mono- or difluoride atoms on the pyrrolidine ring.

The compounds and processes of the present invention will be better understood by reference to the following examples, which are intended as an illustration of and not a limitation upon the scope of the invention. Further, all citations herein are incorporated by reference.

Compounds of the invention were named by Chemdraw Ultra version 7.0.3 CambridgeSoft Corporation., Cambridge, Mass. or were given names consistent with Chemdraw Ultra nomenclature.

EXPERIMENTALS

Example 1

(5S)-N-(4-piperidin-1-yl-phenyl)-2-[5-(thiaxolidine-3-carbonyl)-pyrrolidin-3-ylidene]-acetamide Example 1A (2S)-4-Oxo-2-(thiazolidine-3-carbonyl)-pyrrolidine-1-carboxylic acid tert-butyl ester (2S, 4R)-4-Hydroxy-2-(thiazolidine-3-carbonyl)-pyrrolidine-1-carboxylic acid tert-butyl ester (3.34 g, 0.0111 mol, Example 17A) was dissolved in DMSO and cooled to 0° C. To the cold solution, triethylamine (7.37 g, 0.0729 mol) and sulfur trioxide pyridine complex (8.44 g, 0.0530 mol) were added. The mixture was stirred at 0° C. for 2 hours, brought to room temperature and quenched with water. The mixture was extracted with ethyl acetate and washed with 1 M HCl (60 mL), saturated NaHCO$_3$ (2×40 mL) and brine (1×30 mL). The organic layer was dried with Na$_2$SO$_4$, filtered, concentrated, and purified by column chromatography (ethyl acetate/hexane, 1/1) to give the titled compound 2.05 g. MS (ESI APCI) m/e 299 (M−H)$^+$; $^1$H NMR (300 MHz, methanol-d$_4$): δ ppm 5.07 (d, 1H), 4.80 (m, 1H), 4.57-4.68 (m, 2H), 4.45 (m, 1H), 3.85 (d, 2H), 3.78 (m, 2H), 3.17 (t, 1H), 3.05 (m, 2H), 2.44-2.49 (d, 1H), 1.47 (s, 9H).

Example 1B (2S)-4-Methoxycarbonylmethylene-2-(thiazolidine-3-carbonyl)-pyrrolidine-1-carboxylic acid tert-butyl ester To a solution of Example 1A (5.77 g, 0.0192 mol) in anhydrous dichloromethane (30 mL) was added methyl (triphenylphosphoranylidene)-acetate (8.22 g, 0.0246 mol) and the resulting solution heated to 40° C. for two days. The mixture was cooled, concentrated and purified by column chromatography (ethyl acetate/hexane, 4/6) to provide the titled compound (3.42 g). MS (ESI APCI) m/e 355 (M−H)$^+$; $^1$H NMR (400 MHz, DMSO-d$_6$): δ ppm 5.87 (m, 1H), 4.41-4.78 (m, 4H), 4.31 (d, 1H), 3.74-3.78 (m, 2H), 3.17 (t, 2H), 3.04 (t, 1H), 2.74-2.80 (d, 1H), 1.40 (s, 9H).

Example 1C (2S)-4-Carboxymethylene-2-(thiazolidine-3-carbonyl-pyrrolidine-1-carboxylic acid tert-butyl ester Example 1B (3.42 g, 0.0096 mol) in methanol (10 mL) was treated with 1 M aqueous NaOH (25 mL) and the mixture was stirred at room temperature for 5.5 hours. The mixture was concentrated under reduced pressure, the residue was treated with 1 M HCl and extracted with dichloromethane (3×100 mL). The combined organic layers were dried with magnesium sulfate, filtered, and concentrated to give the titled compound (2 g). MS (ESI APCI) m/e 243 (M−Boc+H)$^+$; $^1$H NMR (300 MHz, CDCl$_3$): δ ppm 5.60 (d, 0.5H), 5.17 (d, 0.5H), 4.47-4.65 (m, 3H), 4.24-4.30 (m, 1H), 3.87 (m, 1H), 3.67 (m, 1H), 3.24 (d, 1H). 3.11 (m, 1H), 2.98 (m, 1H), 2.15 (d, 1H), 1.45 (dd, 9H).

Example 1

(5S)-N-(4-piperidin-1-yl-phenyl)-2-[5-(thiaxolidine-3-carbonyl)-pyrrolidin-3-ylidene]-acetamide Example 1C (65.0 mg, 0.190 mmol) was dissolved in dichloromethane (2.0 mL), treated with PS-Carbodiimide resin (250 mg, 0.253 mmol), and stirred for 5-10 minutes. 4-Piperidinoaniline (22.3 mg, 0.126 mmol) was added and the mixture was stirred for 4.5 hours. The resin was filtered off, washed with methanol, and the filtrate was concentrated to dryness. The reaction mixture was purified by HPLC (reverse phase, 0.1% TFA/acetonitrile gradient). The pure product was de-protected by treatment with trifluoroacetic acid (1.0 mL) in dichloromethane (1.0 mL) for 2 hours. The resulting final product was purified by HPLC (reverse phase, 0.1% TFA/acetonitrile gradient). 17.3 mg, 26% overall yield. MS (ESI APCI) m/e 399 (M−H)$^+$; $^1$H NMR (400 MHz, DMSO): δ ppm 10.7 (d, 2H), 8.95 (s, 1H), 7.57 (d, 2H), 7.30 (s, 2H), 5.93 (s, 1H), 5.34-5.41 (d, 1H), 4.82 (d, 1H), 4.60 (d, 1H), 4.40 (d, 1H), 4.19 (d, 1H), 4.08 (d, 1H), 3.96 (m, 1H), 3.75-3.80 (m, 1H), 3.65 (m, 1H), 3.15 (m, 1H), 3.04-3.07 (m, 1H), 1.77 (s, 3H), 1.59 (s, 2H).

Example 2

(5S)-1-(1-(5-thiazolidine-3-carbonyl)-pyrrolidin-3-yl)-acetyl)-piperdin-4-yl)1,3-dihydro-benzoimidazol-2-one Example 2A (2S)-4-Carboxymethyl-2-(thiazolidine-3-carbonyl)-pyrrolidine-1-carboxylic acid tert-butyl ester A mixture of Example 1C (3.11 g, 0.0090 mol) and platinum oxide (280 mg) in methanol (15 mL) was stirred under an atmosphere of hydrogen at 60 psi pressure for 38 hours at room temperature. Filtration of the catalyst and evaporation of the solvent under reduced pressure provided the desired compound (3.0 g). MS (ESI APCI) m/e 245 (M−Boc+H)$^+$; $^1$H NMR (400 MHz, DMSO-d$_6$): δ ppm 4.37-4.66 (m, 2H), 3.65 (m, 2H), 3.09 (s, 2H), 2.90 (m, 2H), 2.34-2.44 (m, 1H), 2.32 (dd, 1H), 1.91 (m, 1H), 1.41 (s, 9H).

Example 2

(3R, 5S)-1-(1-(5-thiazolidine-3-carbonyl)-pyrrolidin-3-yl)-acetyl)-piperdin-4-yl)1,3-dihydro-benzoimidazol-2-one A vial was charged with PS-Carbodiimide resin (0.15 mmol, 3 eq.), and to the vessel was added the 4-(2-keto-1-benzimidazolinyl)piperidine (0.061 mmol, 1.25 eq.), HOBt (0.049 mmol, 1 eq.) and Example 2A (0.049 mmol, 1 eq.) in 4 mL dimethylacetamide. The vessel was sealed and heated to 55° C. overnight with agitation. After cooling, the mixture was diluted with methanol (4 mL) and filtered. The resin was washed with additional methanol (4 mL), and the combined filtrates were transferred to a vial containing MP-Carbonate resin (0.15 mmol, 3 eq.) and shaken for 4 hours at ambient temperature. The resin was filtered, washed with methanol and the combined filtrates evaporated under reduced pressure to afford the amide product. The resulting residue was treated with 1 mL of 4 M HCl/dioxane for 4 hours at ambient temperature and evaporated to dryness under reduced pressure. The residue was dissolved in 1:1 DMSO/methanol (1.4 mL) and purified by RP-HPLC to provide the titled compound. MS (ESI) m/e 444 (M+H)$^+$; $^1$H NMR (500 MHz, CD$_3$OD) δ ppm 1.85 (m, 2H) 2.39 (m, 2H) 2.66 (m, 2H) 2.78 (m, 4H) 3.17 (m, 4H) 3.74 (m, 2H) 3.90 (m, 1H) 4.09 (m, 1H) 4.63 (m, 7H) 7.06 (m, 3H) 7.23 (m, 1H).

Example 3

(5S)-N-(2-phenoxy-ethyl)-2-5-(thiazolidine-3-carbonyl)-pyrrolidin-3-yl)-acetamide Example 3 was prepared in the same manner as Example 2, by substituting 2-phenoxyphenethylamine for 4-(2-keto-1-benzimidazolinyl)piperidine. MS (ESI) m/e 364 (M+H)$^+$; $^1$H NMR (500 MHz, CD$_3$OD) δ ppm 2.19 (m, 1H) 2.43 (m, 2H) 2.64 (m, 2H) 2.77 (m, 2H) 3.07 (m, 3H) 3.69 (m, 5H) 4.05 (m, 2H) 4.55 (m, 3H) 6.93 (m, 3H) 7.27 (m, 2H).

Example 4

(5S)-N,N-dibenzyl-2-((5-thiazolidine-3-carbonyl)-pyrrolidin-3-yl)-acetamide

Example 4 was prepared in the same manner as Example 2, by substituting dibenzylamine for 4-(2-keto-1-benzimidazolinyl)piperidine. MS (ESI) m/e 424 (M+H)$^+$; $^1$H NMR (500 MHz, CD$_3$OD) δ ppm 1.60 (m, 1H), 2.15 (m, 1H), 2.30 (m, 1H), 2.67 (m, 2H), 2.96 (m, 4H), 3.77 (m, 3H), 4.59 (m, 7H), 7.29 (m, 10H).

Example 5

(5S)-N-(4-chloro-phenyl)-2-(5-(thiazolidine-3-carbonyl)-pyrrolidin-3-yl)-acetamide Example 5 was prepared in the same manner as Example 2, by substituting 4-chloroaniline for 4-(2-keto-1-benzimidazolinyl)piperidine. MS (ESI) m/e 354 (M+H)$^+$; $^1$H NMR (500 MHz, DMSO-d$_6$) δ ppm 2.12 (m, 1H), 2.67 (m, 1H), 3.07 (m, 2H), 3.76 (m, 6H), 4.55 (m, 3H), 7.35 (d, J=9.04 Hz, 2H), 7.60 (d, J=8.73 Hz, 2H), 8.63 (s, 1H), 9.48 (m, 2H), 10.12 (s, 1H).

Example 6

(5S)-1-(4-(4-chlorophenyl)-piperazine-1-yl)-2-(5-(thiazolidine-3-carbonyl)-pyrrolidin-3-yl)-ethanone Example 6 was prepared in the same manner as Example 2, by substituting 1-(4-chlorophenyl)piperazine for 4-(2-keto-1-benzimidazolinyl)piperidine. MS (ESI) m/e 423 (M+H)$^+$; $^1$H NMR (500 MHz, CD$_3$OD) δ ppm 2.66 (m, 2H), 2.77 (m, 2H), 3.10 (m, 7H), 3.76 (m, 7H), 4.65 (m, 5H), 6.95 (d, J=9.04 Hz, 2H), 7.22 (d, J=8.42 Hz, 2H).

Example 7

(5S)-N-(2-(1H-indole-3-yl)-ethyl)-2-(5-(thiazolidine-3-carbonyl)-pyrrolidin-3-yl)-acetamide Example 7 was prepared in the same manner as Example 2, by substituting tryptamine for 4-(2-keto-1-benzimidazolinyl)piperidine. MS (ESI) m/e 387 (M+H)$^+$; $^1$H NMR (500 MHz, DMSO-d$_6$) δ ppm 2.02 (m, 2H), 2.28 (m, 2H), 2.83 (m, 2H), 3.09 (m, 1H), 3.33 (s, 2H), 3.71 (m, 5H), 4.59 (m, 4H), 7.05 (m, 3H), 7.34 (t, J=8.58 Hz, 1H), 7.52 (d, J=7.80 Hz, 1H), 8.01 (d, J=5.30 Hz, 1H), 8.59 (s, 1H), 9.45 (s, 1H), 10.78 (s, 1H).

Example 8

(5S)-N-(3-chlorobenzyl)-2-(5-(thiazolidine-3-carbonyl)-pyrrolidin-3-yl)-acetamide Example 8 was prepared in the same manner as Example 2, by substituting 3-chlorobenzylamine for 4-(2-keto-1-benzimidazolinyl)piperidine. MS (ESI) m/e 368 (M+H)$^+$; $^1$H NMR (500 MHz, DMSO-d$_6$) δ ppm 2.05 (m, 1H), 2.37 (d, J=7.17 Hz, 2H), 2.86 (d, J=79.53 Hz, 1H), 3.08 (m, 3H), 3.72 (m, 4H), 4.27 (d, J=5.61 Hz, 1H), 4.58 (m, 4H), 7.30 (m, 4H), 8.47 (d, J=5.30 Hz, 1H), 8.60 (s, 1H), 9.46 (s, 1H).

Example 9

(3S, 5S)-Pentanedioic Acid Phenylamide-5-(thiazolidine-3-(carbonyl)-pyrrolidin-3-yl)methyl)-amide A vial containing PS-Carbodiimide resin (0.19 mmol, 3 eq.), glutaranilic acid (0.079 mmol, 1.25 eq.), HOBt (0.063 mmol, 1 eq.) and Example 17D (0.063 mmol, 1 eq.) in 4 mL of dimethylacetamide was sealed and heated to 55° C. overnight with agitation. After cooling, the mixture was diluted with methanol (4 mL) and filtered, the resin was washed with additional methanol (4 mL), and the combined filtrates were transferred to a vial containing MP-Carbonate resin (0.15 mmol, 3 eq.) and shaken for 4 hours at ambient temperature. The resin was filtered, washed with methanol and the combined filtrates concentrated under reduced pressure to provide the amide product. The resulting residue was treated with 1 mL of 4 M HCl/dioxane for 4 hours at ambient temperature and concentrated to dryness under reduced pressure. The residue was dissolved in 1:1 DMSO/methanol (1.4 mL) and purified by RP-HPLC to provide the titled compound. MS (ESI) m/e 405 (M+H)$^+$; $^1$H NMR (500 MHz, pyridine-d$_5$) δ ppm 1.94 (d, J=39.97 Hz, 1H), 2.33 (m, 2H), 2.50 (m, 2H), 2.66 (m, 4H), 2.83 (m, 2H), 2.94 (m, 2H), 3.37 (m, 1H), 3.55 (m, 2H), 3.81 (m, 2H), 4.60 (m, 2H), 5.00 (m, 1H), 7.11 (t, J=7.32 Hz, 1H), 7.37 (m, 2H), 8.05 (d, J=7.93 Hz, 2H), 8.90 (d, J=3.97 Hz, 1H), 10.74 (s, 1H).

Example 10

(3S, 5S)-2-(4-methanesulfonyl-phenyl)-N-(5-(thiazolidine-3-carbonyl)-pyrrolidin-3-ylmethyl)-acetamide Example 10 was prepared in the same manner as Example 9, by substituting 4-methylsulphonylphenylacetic acid for glutaranilic acid. MS (ESI) m/e 412 (M+H)+; $^1$H NMR (500 MHz, pyridine-$d_5$) δ ppm 1.93 (m, 2H), 2.66 (m, 1H), 2.81 (m, 2H), 2.94 (m, 3H), 3.20 (m, 3H), 3.39 (m, 1H), 3.58 (m, 2H), 3.83 (m, 3H), 4.66 (m, 2H), 4.98 (m, 1H), 6.58 (s, 1H), 7.67 (m, 2H), 8.08 (m, 2H), 9.22 (s, 1H).

Example 11

(3S, 5S)-N-({[5-(Thiazolidine-3-carbonyl)-pyrrolidin-3-ylmethyl]-carbamoyl}-methyl)-benzamide Example 11 was prepared in the same manner as Example 9, by substituting hippuric acid for glutaranilic acid. MS (ESI) m/e 377 (M+H)+; $^1$H NMR (500 MHz, pyridine-$d_5$) δ ppm 1.94 (m, 3H), 2.71 (m, 2H), 2.94 (m, 2H), 3.43 (m, 1H), 3.57 (m, 2H), 3.81 (m, 2H), 4.47 (m, 2H), 4.66 (m, 1H), 5.06 (m, 1H), 7.43 (m, 5H), 8.25 (m, 2H), 9.16 (t, J=5.64 Hz, 1H), 9.67 (br s, 1H).

Example 12

(3S, 5S)-2-(4-Hydroxy-trans-cyclohexylamino)-N-[5-(thiazolidine-3-carbonyl)-pyrrolidin-3-ylmethyl]-acetamide

Example 12 A (2S, 4R)-4-[(2-Chloro-acetylamino)-methyl]-2-(thiazolidine-3-carbonyl)-pyrrolidine-1-carboxylic acid tert-butyl ester To a mixture of Example 17D (0.585 mmol) and triethylamine (163 µL, 11.7 mmol) in 5 mL of methylene chloride was added chloroacetyl chloride (65 µL, 0.82 mmol). The mixture was stirred for 1 hour after which methanol was added, and the mixture was purified by reverse-phase HPLC to provide the titled compound. MS (ESI) m/z 392 [M+H]+.

Example 12

(3S, 5S)-2-(4-Hydroxy-trans-cyclohexylamino)-N-[5-(thiazolidine-3-carbonyl)-pyrrolidin-3-ylmethyl]-acetamide Example 12A (35 mg, 0.089 mmol) and trans-4-hydroxy-cyclohexylamine (55 mg, 0.196 mmol) in 2 mL of acetonitrile was stirred for 72 hours. The mixture was purified by reverse-phase HPLC to provide the desired amine. MS (ESI) m/z+471 [M+H]+. The Boc protecting group was removed as described in Example 17 to provide the titled compound. MS (ESI) m/z+371 [M+H]+.

Example 13

(3S, 5S)-2-(3-Methoxy-phenoxy)-N-[5-(thiazolidine-3-carbonyl)-pyrrolidin-3-ylmethyl]-acetamide Example 13 was prepared in the same manner as Example 9, by substituting 3-methoxyphenoxyacetic acid for glutaranilic acid. MS (ESI) m/e 380 (M+H)+; $^1$H NMR (500 MHz, pyridine-$d_5$) δ ppm 1.88 (m, 1H), 1.95 (m, 2H), 2.67 (m, J=13.43 Hz, 2H), 2.83 (m, 2H), 2.96 (m, 2H), 3.40 (m, 1H), 3.62 (m, 3H), 3.78 (m, 3H), 4.62 (m, 1H), 4.80 (m, 1H), 5.00 (m, 1H), 6.65 (m, 6H), 9.06 (s, 1H).

Example 14

(3S, 5S)-N-5-(thiazolidine-3-carbonyl)-pyrrolidine-3-ylmethyl)-2-(toluene-4-sulfonylamino)acetamide Example 14 was prepared in the same manner as Example 9, by substituting N-(p-toluene sulfonyl)glycine for glutaranilic acid. MS (ESI) m/e 427 (M+H)+; $^1$H NMR (500 MHz, pyridine-$d_5$) δ ppm 1.98 (s, 2H), 2.17 (m, 2H), 2.86 (m, 2H), 3.36 (m, 1H), 3.54 (m, 4H), 3.78 (m, 2H), 4.09 (s, 2H), 4.47 (d, J=8.54 Hz, 1H), 4.65 (m, 2H), 4.93 (m, 1H), 8.02 (m, 4H), 9.05 (s, 2H), 9.81 (s, 2H).

Example 15

(3S, 5S)-4-(4-Methoxy-phenyl)-4-oxo-N-[5-(thiazolidine-3-carbonyl)-pyrrolidine-3-ylmethyl]-butyramide Example 15 was prepared in the same manner as Example 9, by substituting 3-(4-methoxybenzoyl)propionic acid for glutaranilic acid. MS (ESI) m/e 406 (M+H)+; $^1$H NMR (500 MHz, pyridine-$d_5$) δ ppm 1.96 (m, 2H), 2.71 (m, 2H), 2.82 (m, 2H), 2.94 (m, 1H), 3.45 (m, 2H), 3.57 (dd, J=14.04, 6.71 Hz, 2H), 3.70 (m, 3H), 3.83 (m, 4H), 4.64 (m, 2H), 5.11 (m, 1H), 7.01 (m, 4H), 8.11 (d, J=8.85 Hz, 2H), 9.02 (s, 1H).

Example 16

(3S, 5S)-1-(4-Cyano-phenyl)-3-[5-(thiazolidine-3-carbonyl)-pyrrolidin-3-ylmethyl]-urea To a solution of Example 17D (32 mg, 0.1 mmol) in anhydrous dichloromethane (3 mL) was added N,N-diisopropylethylamine (0.035 mL, 0.2 mmol), followed by 4-cyanophenyl isocyanate (15.85 mg, 0.11 mmol). The mixture was stirred for 8 hours at room temperature, concentrated under reduced pressure, and the residue partitioned between ethyl acetate (10 mL) and H$_2$O (5 mL). The aqueous layer was extracted with ethyl acetate (2×5 mL), and the combined organic layers were dried (sodium sulfate), filtered, and concentrated to an oil. The oil was dissolved in anhydrous dichloromethane (3 mL) and trifluoroacetic acid (0.075 mL) and dichloromethane (0.075 mL) were added to this solution via syringe. The mixture was allowed to stir for 5 hours at room temperature and then concentrated under reduced pressure to provide the titled compound. MS (ESI) m/e 360 (M+H)+, 358 (M−H)−; 1H NMR (400 MHz, CD$_3$OD) δ ppm 1.72 (m, 1H), 2.64 (m, 2H) 3.02 (m, 1H) 3.10 (m, 1H) 3.16 (m, 1H) 3.27 (m, 1H) 3.45 (m, 1H) 3.69 (m, 1H) 3.83 (m, 1H), 4.47 (m, 1H) 4.61 (m, 2H) 7.31 (d, 2H) 7.53 (d, 2H).

Example 17

(3S, 5S)-1-Cyclopentyl-3-[5-(thiazolidine-3-carbonyl)-pyrrolidin-3-ylmethyl]-urea

Example 17A (2S, 4R)-4-Hydroxy-2-(thiazolidine-3-carbonyl)-pyrrolidine-1-carboxylic acid tert-butyl ester To a mixture of trans-Boc-L-hydroxyproline (50.0 g, 0.22 mol), 1-[3-(dimethylamino)propyl]-3-ethylcarbodiimide hydrochloride (49.7 g, 0.26 mol) and HOBT (35.1 g, 0.26 mol) in DMF/dichloromethane (250 mL/70 mL) at room temperature was added triethylamine (30 mL, 0.22 mol) and thiazolidine (17.9 mL, 0.23 mol). The mixture was stirred at room temperature for 24 hours, the solvent was removed under reduced pressure and the resulting viscous liquid purified using flash silica gel chromatography eluting with 100% ethyl acetate to provide the titled compound. MS (ESI) m/e 303(M+H)$^+$; $^1$H NMR (500 MHz, DMSO-d$_6$): δ ppm 1.35-1.40 (s, 9H), 2.35-2.45 (m, 1H), 2.90-3.00 (m, 2H), 3.05-3.15 (m, 2H), 3.60-3.70 (m, 2H), 3.62-3.80 (m, 2H), 4.35 (m, 0.5H), 4.75 (m, 0.5H), 4.55 (m, 1H), 4.90 (m, 1H).

Example 17B (2S, 4R)-4-Methanesulfonyloxy-2-(thiazolidine-3-carbonyl)-pyrrolidine-1-carboxylic acid tert-butyl ester To a mixture of Example 17A (19.9 g, 66 mmol) and triethylamine (9.5 mL, 70 mmol) in THF (200 mL) at 0° C. under nitrogen was added methanesulfonyl chloride (15.08 g, 132 mmol) drop wise over 30 minutes. The mixture was allowed to warm up to room temperature, stirred for 12 hours, and then concentrated under reduced pressure. The residue was partitioned between water and ethyl acetate and the aqueous layer was extracted with ethyl acetate (3×300 mL). The combined organic layers were dried (magnesium sulfate), filtered and concentrated to a yellow oil. The yellow oil was purified using a Biotage 65+ eluting with 100% ethyl acetate to provide the titled compound. MS (ESI) m/e 380 (M+H)$^+$; 1H NMR (300 MHz, CD$_3$OD) δ ppm 1.44 (m, 9H) 2.22 (m, 1H) 2.65 (m, 1H) 3.05 (m, 1H) 3.14 (d, 3H) 3.17 (m, 1H) 3.74 (m, 3.73 Hz, 1H) 3.81 (m, 2H) 4.00 (m, 1H) 4.53 (m, 1H) 4.70 (m, 2H) 5.32 (m, 1H).

Example 17C (2S 4S)-4-Cyano-2-(thiazolidine-3-carbonyl)-pyrrolidine-1-carboxylic acid tert-butyl ester To a solution of Example 17B (16.55 g, 44 mmol) in dry DMF (100 mL) under nitrogen was added tetrabutylammonium cyanide (50 g, 200 mmol). The mixture was heated to 50° C. for 60 hours and then poured into cold water and extracted with ethyl acetate (3×250 mL). The combined organic layers were dried (magnesium sulfate) and concentrated under reduced pressure. The residue was purified by flash silica gel chromatography with 50% ethyl acetate/50% hexane to provide the titled compound (12 g). MS (ESI) m/e 312 (M+H)$^+$, 310 (M–H)$^-$; $^1$H NMR (400 MHz, CD$_3$OD) δ ppm 1.44 (m, 9H) 2.10 (m, 1H) 2.79 (m, 1H) 3.05 (m, 1H) 3.17 (m, 1H) 3.33 (m, 1H) 3.57 (dd, 1H) 3.83 (m, 2H) 3.96 (m, 1H) 4.48 (m, 1H) 4.65 (m, 2H).

Example 17D (2S, 4R)-4-Aminomethyl-2-(thiazolidine-3-carbonyl-pyrrolidine-1-carboxylic acid tert-butyl ester To a mixture of Example 17C (31.1 g, 0.1 mol) and cobalt (II) chloride (11.9 g, 0.05 mol) in methanol (300 mL) at 0° C. was added in portions sodium borohydride (15.2 g, 0.4 mol). The mixture was stirred for 1 hour at room temperature, the solvent was azeotroped off with chloroform (5×300 mL). The residue was purified by silica gel chromatography with 10% methanol/90% dichloromethane/0.2% ammonium hydroxide to provide the title compound (15 g). MS (ESI) m/e 316 (M+H)$^+$; $^1$H NMR (400 MHz, CD$_3$OD) δ ppm 1.39 (m, 9H) 2.35 (m, 1H) 2.50 (m, 1H) 2.72 (m, 2H) 3.00 (m, 1H) 3.13 (m, 2H) 3.75 (m, 2H) 3.94 (m, 1H) 4.57 (m, 2H).

Example 17

(3S, 5S)-1-Cyclopentyl-3-[5-(thiazolidine-3-carbonyl)-pyrrolidin-3-ylmethyl]-urea To a mixture of Example 17D (32.0 mg, 0.1 mmol) and triethylamine (0.03 mL, 0.2 mmol) in anhydrous dichloromethane (2 mL) was added pyrrolidine-1-carbonyl chloride (16.0 mg, 0.12 mmol) and the mixture was allowed to stir for 6 hours at room temperature. The mixture was concentrated under reduced pressure and the residue was chromatographed on a Biotage 40M eluting with 20% hexane/80% ethyl acetate to provide a yellow oil. The oil was dissolved in anhydrous dichloromethane (5 mL) and trifluoroacetic acid (0.075 mL) in dichloromethane (0.075 mL) were added to the mixture via syringe. The mixture was allowed to stir for 5 hours at room temperature and concentrated under reduced pressure to provide the titled compound. MS (ESI) m/e 313 (M+H)$^+$; $^1$H NMR (400 MHz, CD$_3$OD) δ ppm 1.72 (m, 1H) 1.91 (t, 4H) 2.66 (m, 2H) 3.08 (m, 1H) 3.16 (m, 2H) 3.26 (m, 2H) 3.30 (t, 4H) 3.45 (m, 1H) 3.74 (m, 1H) 3.87 (m, 1H) 4.51 (m, 1H) 4.62 (m, 2H).

Example 18

(3S, 5S)-N-[5-(Thiazolidine-3-carbonyl)-pyrrolidin-3-ylmethyl]-isophthalamic acid methyl ester

Example 18A (2S, 4R)-4-[(3-Methoxycarbonyl-benzoylamino)-methyl]-2-(thiazolidine-3-carbonyl)-pyrrolidine-1-carboxylic acid tert-butyl ester To a solution of monomethyl isophthalate (226 mg, 1.26 mmol) in anhydrous N,N-dimethylformamide (8 mL) was added 1-hydroxybenzotriazole monohydrate (204 mg, 1.51 mmol), followed by 1-[3-(dimethylamino)propyl]-3-ethylcarbodiimide hydrochloride (288 mg, 1.51 mmol) and triethylamine (0.180 mL, 1.26 mmol). The mixture was stirred at room temperature for 30 minutes followed by the addition of a solution of Example 17D (380 mg, 1.2 mmol) in anhydrous N,N-dimethylformamide (2 mL). The mixture was allowed to stir at room temperature for 16 hours, concentrated under reduced pressure. The residue was diluted with dichloromethane (20 mL) and extracted with 1 M HCl (20 mL), saturated sodium bicarbonate (20 mL) and brine (20 mL) respectively. The organic layer was separated and dried (Na$_2$SO$_4$), filtered and concentrated to a light yellow oily solid which was chromatographed on a Biotage 40M with ethyl acetate to provide the titled compound. MS (APCI) m/e 478 (M+H)$^+$.

Example 18

(3S, 5S)-N-[5-(Thiazolidine-3-carbonyl)-pyrrolidin-3-ylmethyl]-isophthalamic acid methyl ester A solution of Example 18A (100 mg) in 4 M HCl in dioxane (2 mL) was stirred at room temperature for 16 hours, and concentrated under reduced pressure. The residue was taken up and concentrated under reduced pressure under the following solvents, methanol (10 mL), ether (10 mL) and dichloromethane (10 mL) to provide the titled compound as a pale yellow solid.

MS (ESI) m/e 378 (M+H)$^+$; $^1$H NMR (500 MHz, CD$_3$OD): δ ppm 1.80 (m, 1H), 2.74 (m, 1H), 2.82 (m, 1H), 3.09 (m, 1H), 3.16 (q, 1H), 3.23 (dd, 1H), 3.33 (m, 1H), 3.56 (m, 3H), 3.74 (m, 1H), 3.88 (m, 1H), 3.93 (d, 3H), 4.52 (m, 1H), 4.67 (m, 2H), 7.61 (m, 1H), 8.07 (m, 1H), 8.19 (d, 1H), 8.49 (m, 1H).

Example 19

(3S, 5S)-N-Methyl-N-[5-(thiazolidine-3-carbonyl)-pyrrolidin-3-ylmethyl]-benzamide To a mixture of Example 17D (202.1 mg, 0.64 mmol) and triethylamine (0.14 mL) in anhydrous dichloromethane (5 mL) was added benzoyl chloride (0.08 mL, 0.64 mmol) dropwise. The mixture was allowed to stir for 6 hours at room temperature and then concentrated under reduced pressure. The residue was partitioned between ethyl acetate (30 mL) and H$_2$O (10 mL). The aqueous layer was extracted with ethyl acetate (2×20 mL). The combined organic layers were dried (Na$_2$SO$_4$), filtered, and concentrated under reduced pressure to an oil, which was chromatographed using a Biotage 40M eluting with 20% hexane/80% ethyl acetate to provide (2S, 4R)-4-(benzoylamino-methyl)-2-(thiazolidine-3-carbonyl)-pyrrolidine-1-carboxylic acid tert-butyl ester as a brown oil. MS (ESI) m/e 420 (M+H)$^+$, 418 (M–H)$^-$.

To a solution of (2S, 4R)-4-(benzoylamino-methyl)-2-(thiazolidine-3-carbonyl)-pyrrolidine-1-carboxylic acid tert-butyl ester (180 mg, 0.43 mmol) in anhydrous DMF (8 mL) was added sodium hydride (13 mg, 0.56 mmol) under nitrogen. The mixture stirred for 15 minutes followed by the addition of methyl iodide (0.04 mL, 0.64 mmol). The mixture was allowed to stir for 2 hours at room temperature, concentrated under reduced pressure, and the residue was partitioned between ethyl acetate (10 mL) and H$_2$O (5 mL). The aqueous layer was extracted with ethyl acetate (2×10 mL), and the combined organic layers were dried (Na$_2$SO$_4$), filtered, and concentrated under reduced pressure to provide a yellow oil. To a solution of the oil in dichloromethane (10 mL) was added a solution of 4N HCl in dioxane (2 mL, 8 mmol) and the mixture was allowed to stir for 12 hours at room temperature. The mixture was concentrated under reduced pressure and the residue purified by RP-HPLC (CH$_3$CN/H$_2$O/TFA). MS (ESI) m/e 334 (M+H)$^+$, 332 (M–H)$^-$; 1H NMR (500 MHz, CD$_3$OD) δ ppm 2.70 (m, 1H) 3.02 (s, 3H) 3.10 (m, 1H) 3.17 (t, 1H) 3.55 (m, 2H) 3.66 (m, 1H) 3.78 (m, 2H) 3.87 (m, 1H) 4.53 (m, 1H) 4.67 (m, 2H) 7.44 (dd, 2H) 7.48 (m, 3H).

Example 20

(3S, 5S)-3-Bromo-N-[5-(thiazolidine-3-carbonyl)-pyrrolidin-3-ylmethyl]-benzamide Example 20 was prepared in the same manner as Example 9, by substituting 3-bromobenzoic acid for glutaranilic acid. MS (ESI) m/e 398 (M+H)$^+$; $^1$H NMR (500 MHz, pyridine-d$_5$) δ ppm 2.01 (m, 2H), 2.49 (s, 2H), 2.86 (m, 2H), 3.56 (m, 2H), 3.94 (dd, J=10.92, 7.17 Hz, 2H), 4.63 (m, 2H), 5.14 (m, 2H), 8.09 (d, J=7.80 Hz, 3H), 8.36 (s, 2H), 9.49 (br s, 2H).

Example 21

(3S, 5S)-2,3-Dimethyl-N-[5-(thiazolidine-3-carbonyl)-pyrrolidin-3-ylmethyl]-benzamide Example 21 was prepared in the same manner as Example 9, by substituting 2,3-dimethylbenzoic acid for glutaranilic acid. MS (ESI) m/e 348 (M+H)$^+$; $^1$H NMR (500 MHz, pyridine-d$_5$) δ ppm 2.08 (m, 1H), 2.08 (m, 3H), 2.36 (m, 3H), 2.89 (m, 2H), 3.20 (m, 1H), 3.60 (m, 2H), 3.84 (m, 4H), 4.03 (d, J=9.98 Hz, 1H), 4.66 (m, 2H), 5.22 (m, 1H), 7.09 (m, 2H), 7.41 (m, 1H), 7.95 (s, 2H), 9.20 (s, 1H).

Example 22

(3S, 5S)-N-[5-(Thiazolidine-3-carbonyl)-pyrrolidin-3-ylmethyl]-isophthalamic acid To a solution of Example 18A (100 mg) in tetrahydrofuran (0.5 mL) and ethanol (0.5 mL) was added 2 M NaOH (1 mL) and the resulting mixture was stirred at room temperature for 16 hours. The mixture was adjusted to a pH 2-3 by the addition of 1 M HCl, extracted with ethyl acetate (3×15 mL) and the combined organic layers washed with brine (15 mL), dried (Na$_2$SO$_4$), filtered and concentrated to provide a white solid which was processed as described in Example 18 to provide the titled compound as a pale yellow solid. MS (ESI) m/e 364 (M+H)$^+$; $^1$H NMR (500 MHz, CD$_3$OD) δ ppm 1.82 (m, 1H), 2.74 (m, 1H), 2.83 (m, 1H), 3.09 (m, 1H), 3.17 (q, 1H), 3.24 (dd, 1H), 3.33 (m, 1H), 3.55 (m, 2H), 3.64 (m, 1H), 3.75 (m, 1H), 3.88 (m, 1H), 4.52 (m, 1H), 4.66 (m, 2H), 7.60 (m, 1H), 8.06 (t, 1H), 8.20 (d, 1H), 8.49 (m, 1H).

Example 23

(3S, 5S)-3-Methanesulfonyl-N-[5-(thiazolidine-3-carbonyl)-pyrrolidin-3-ylmethyl]-benzamide Example 23 was prepared in the same manner as example 18 by substituting 3-methyl sulfonyl benzoic acid for monomethyl isophthalate. MS (ESI) m/e 398 (M+H)$^+$; $^1$H NMR (500 MHz, CD$_3$OD): δ ppm 1.19 (m, 1H,) 1.81 (m, 1H), 2.75 (m, 1H), 2.82 (m, 1H), 3.05 (m, 2H), 3.27 (m, 4H), 3.52 (m, 3H), 3.75 (m, 1H), 3.88 (m, 1H), 4.52 (m, 1H), 4.67 (m, 2H), 7.76 (m, 1H,) 8.16 (m, 2H), 8.40 (d, 1H).

Example 24

(3S, 5S)-4-Hydroxy-N-[5-(thiazolidine-3-carbonyl)-pyrrolidin-3-ylmethyl]-benzamide Example 24 was prepared in the same manner as Example 9, by substituting 4-hydroxybenzoic acid for glutaranilic acid. MS (ESI) m/e 336 (M+H)$^+$; $^1$H NMR (500 MHz, pyridine-d$_5$) δ ppm 2.01 (m, 1H), 2.49 (m, 1H), 2.83 (m, 2H), 3.12 (d, J=7.80 Hz, 1H), 3.55 (m, 1H), 3.78 (m, 4H), 3.94 (d, J=7.80 Hz, 1H), 4.61 (m, 2H), 5.16 (m, 1H), 8.25 (m, 5H), 9.11 (br s, 2H).

Example 25

(3S, 5S)-2,3-Dihydro-benzo[1,4]dioxine-6-carboxylic acid [5-(thiazolidine-3-carbonyl)-pyrrolidin-3-ylmethyl]-amide To a solution of Example 17D (31.6 mg, 0.1 mmol) in anhydrous dichloromethane (1 mL) was added triethylamine (0.021 mL, 0.15 mmol) followed by 2,3-dihydro-1,4-benzodioxine-6-carbonyl chloride (23.8 mg, 0.12 mmol). The mixture was shaken overnight at room temperature and concentrated under reduced pressure, MS (APCI) m/e 472 (M+H)+. The residue was dissolved in anhydrous dichloromethane (0.5 mL) and trifluoroacetic acid (0.5 mL) was added. The mixture was allowed to stir for 5 hours at room temperature, concentrated under reduced pressure, and the residue purified by reverse-phase HPLC to provide the titled compound. MS (ESI) m/e 372 (M+H)+; $^1$H NMR (500 MHz, $CD_3OD$): δ ppm 1.75-2.4 (m, 1H), 2.74 (m, 2H), 3.15 (m, 3H), 3.33 (m, 1H), 3.47 (m, 3H), 3.75 (m, 1H), 3.87 (m, 1H), 4.28 (m, 4H), 4.51 (m, 1H), 4.66 (m, 2H), 6.90 (dd, 1H), 7.33 (m, 2H).

Example 26

(3S, 5S)-2,2-Difluoro-benzo[1,3]dioxole-5-carboxylic acid [5-(thiazolidine-3-carbonyl)-pyrrolidin-3-ylmethyl]-amide Example 26 was prepared in the same manner as described in Example 25 by substituting 2,2-difluoro-1,3-benzodioxole-5-carbonyl chloride for 2,3-dihydro-1,4-benzodioxine-6-carbonyl chloride. MS (ESI) m/e 400 (M+H)+; $^1$H NMR (500 MHz, $CD_3OD$): δ ppm 1.79 (m, 1H), 2.76 (m, 2H), 3.08 (t, 1H), 3.16 (q, 1H), 3.24 (m, 1H), 3.33 (m, 1H), 3.50 (m, 3H), 3.75 (m, 1H), 3.87 (m, 1H), 4.51 (m, 1H), 4.64 (m, 2H), 7.31 (d, 1H), 7.69 (m, 2H).

Example 27

(3S, 5S)-N-[5-(Thiazolidine-3-carbonyl)-pyrrolidin-3-ylmethyl]-3-trifluoromethoxy-benzamide Example 27 was prepared in the same manner as example 9, by substituting 3-(trifluoromethoxy)benzoic acid for glutaranilic acid. MS (ESI) m/e 404 (M+H)+; $^1$H NMR (500 MHz, pyridine-$d_5$) δ ppm 2.03 (m, 1H), 2.49 (m, 1H), 2.86 (m, 1H), 3.18 (m, 1H), 3.57 (m, 2H), 3.80 (m, 4H), 3.97 (dd, J=10.92, 7.17 Hz, 1H), 4.63 (m, 2H), 5.15 (m, 1H), 7.41 (m, 3H), 8.13 (m, J=6.24 Hz, 2H), 9.61 (br s, 2H).

Example 28

(3S, 5S)-N-[5-(Thiazolidine-3-carbonyl)-pyrrolidin-3-ylmethyl]-3-[1,2,4]triazol-1-ylmethyl-benzamide Example 28A (2S, 4R)-4-[(3-Chloromethyl-benzoylamino)-methyl]-2-(thiazolidine-3-carbonyl)-pyrrolidine-1-carboxylic acid tert-butyl ester To a solution of Example 17D (95 mg, 0.3 mmol) in anhydrous dichloromethane (3 mL) was added triethylamine (0.063 mL, 0.45 mmol) followed by 3-(chloromethy)benzoyl chloride (0.051 mL, 0.36 mmol). The mixture was shaken overnight at room temperature, concentrated under reduced pressure, and the residue was purified by reverse-phase HPLC, MS (APCI) m/e 472 (M+H)+.

Example 28

(3S, 5S)-N-[5-(Thiazolidine-3-carbonyl)-pyrrolidin-3-ylmethyl]-3-[1,2,4]triazol-1-ylmethyl-benzamide Example 28A (23.4 mg, 0.05 mmol) was dissolved in anhydrous N,N-dimethylformamide (1 mL) and treated with 1,2,4-triazole (4 mg, 0.06 mmol), anhydrous potassium carbonate (10.3 mg, 0.075 mmol) and a catalytic amount of potassium iodide (1.2 mg) at 60° C. for 5 hours. The mixture was diluted with water and extracted with ethyl acetate (3×30 mL). The combined organic layers were washed with water and brine respectively, dried ($Na_2SO_4$), filtered, and concentrated under reduced pressure. The residue was treated with dichloromethane (0.5 mL) and trifluoroacetic acid (0.5 mL) at room temperature for 5 hours, concentrated under reduced pressure, and the residue purified by reverse-phase HPLC to provide the titled compound. MS (ESI) m/e 472 (M+H)+; $^1$H NMR (500 MHz, $CD_3OD$): δ ppm 1.78 (s, 1H), 2.72 (d, 2H), 3.07 (t, 1H), 3.15 (t, 1H), 3.22 (d, 1H), 3.51 (m, 3H), 3.72 (m, 1H), 3.88 (m, 1H), 4.50 (m, 1H), 4.63 (m, 2H), 5.50 (s, 2H), 7.50 (m, 2H), 7.78 (d, 2H), 8.01 (s, 1H), 8.60 (s, 1H).

Example 29

(3S, 5S)-3-Chloro-N-[5-(thiazolidine-3-carbonyl)-pyrrolidin-3-ylmethyl]-benzamide Example 29 was prepared in the same manner as Example 9, by substituting 3-chlorobenzoic acid for glutaranilic acid. MS (ESI) m/e 354 (M+H)+; $^1$H NMR (500 MHz, pyridine-$d_5$) δ ppm 2.03 (m, 2H), 2.49 (m, 1H), 2.87 (m, 1H), 3.18 (m, 1H), 3.57 (m, 2H), 3.79 (m, 3H), 3.97 (m, 1H), 4.62 (m, 2H), 5.19 (m, 1H), 7.32 (m, 1H), 7.45 (m, 1H), 8.05 (d, J=7.80 Hz, 1H), 8.20 (d, J=1.87 Hz, 1H), 8.23 (m, 2H), 9.50 (s, 1H).

Example 30

(3S, 5S)-3-(1H-Tetrazol-5-yl)-N-[5-(thiazolidine-3-carbonyl)-pyrrolidin-3-ylmethyl]-benzamide Example 30A (2S, 4R)-4-[(3-Cyano-benzoylamino)-methyl]-2-(thiazolidine-3-carbonyl)-pyrrolidine-1-carboxylic acid tert-butyl ester To a solution of Example 17D (1.38 g, 4.38 mmol) in anhydrous dichloromethane (25 mL) was added triethylamine (0.9 mL) followed by 3-cyanobenzoyl chloride (0.727 g, 4.38 mmol) and the mixture was stirred for 4 hours at room temperature. The mixture was concentrated under reduced pressure and the residue partitioned between ethyl acetate (50 mL) and $H_2O$ (20 mL). The aqueous layer was extracted with ethyl acetate (2×30 mL) and the combined organic layers dried ($Na_2SO_4$), filtered, and concentrated to an oil which was chromatographed on a Biotage 40M eluting with 10% hexane/90% ethyl acetate to provide the titled compound. MS (ESI) m/e 445 (M+H)+, 443 (M−H)−; 1H NMR (300 MHz, $CD_3OD$) δ ppm 1.39 (s, 6H) 1.45 (s, 3H) 1.65 (m, 1H) 2.53 (m, 2H) 3.05 (m, 1H) 3.19 (m, 2H) 3.46 (m, 2H) 3.78 (m, 2H) 4.61 (m, 3H) 7.66 (t, 1H) 7.89 (d, 1H) 8.11 (d, 1H) 8.17 (s, 1H).

Example 30B (2S, 4R)-4-{[3-(1H-Tetrazol-5-yl)-benzoylamino]-methyl}-2-(thiazolidine-3-carbonyl)-pyrrolidine-1-carboxylic acid tert-butyl ester To a solution of Example 30A (300 mg, 0.67 mmol) in anhydrous DMF (4 mL) was added sodium azide (522 mg, 8.04 mmol) followed by ammonium chloride (428.8 mg, 8.04 mmol). The mixture was flushed with nitrogen, then exposed to microwave irradiation (20W, 175° C.) for 15 minutes. The mixture was concentrated under reduced pressure to afford a brown oil. The brown oil was purified by RP-HPLC to provide the titled compound. MS (ESI) m/e 488 (M+H)$^+$, 486 (M−H)$^-$; 1H NMR (300 MHz, CD$_3$OD) δ ppm 1.39 (s, 6H) 1.47 (s, 3H) 1.68 (m, 1H) 1.94 (m, 1H) 2.59 (m, 2H) 3.02 (m, 1H) 3.14 (m, 1H) 3.23 (m, 1H) 3.48 (m, 2H) 3.79 (m, 2H) 4.56 (m, 2H) 4.72 (m, 1H) 7.55 (t, 1H) 7.82 (d, 1H) 8.18 (dd, 1H) 8.44 (s, 1H).

Example 30

(3S, 5S)-3-(1H-Tetrazol-5-yl)-N-[5-(thiazolidine-3-carbonyl)-pyrrolidin-3-ylmethyl]-benzamide To a solution of Example 30B (292.8 mg, 0.6 mmol) dissolved in methanol (10 mL) was added a solution of 4N HCl in dioxane (1.5 mL, 4 M, 6 mmol) via syringe at room temperature. The mixture was allowed to stir for 12 hours at room temperature, concentrated under reduced pressure to provide the titled compound. MS (ESI) m/e 388 (M+H)$^+$, 386 (M−H)$^-$; 1H NMR (500 MHz, CD$_3$OD) δ ppm 1.97 (m, 1H) 2.86 (m, 2H) 3.16 (m, 2H) 3.39 (m, 1H) 3.61 (s, 2H) 3.69 (m, 1H) 3.76 (s, 2H) 3.97 (m, 1H) 4.53 (m, 2H) 7.69 (m, 1H) 8.07 (m, 1H) 8.20 (m, 1H) 8.57 (s, 1H).

Example 31

(3S, 5S)-2,3-Dihydro-benzofuran-5-carboxylic acid [5-(thiazolidine-3-carbonyl)-pyrrolidin-3-ylmethyl]-amide Example 31 was prepared in the same manner as Example 25 by substituting 2,3-dihydro-1-benzofuran-5-carbonyl chloride for 2,3-dihydro-1,4-benzodioxine-6-carbonyl chloride. MS (ESI) m/e 362 (M+H)$^+$; 1H NMR (500 MHz, CD$_3$OD): δ ppm 1.79 (dd, 1H), 2.74 (m, 2H), 3.07 (t, 1H), 3.16 (q, 1H), 3.23 (m, 3H), 3.48 (m, 4H), 3.73 (m, 1H), 3.87 (m, 1H), 4.50 (m, 1H), 4.63 (m, 4H), 6.77 (d, 1H), 7.63 (d, 1H), 7.70 (s, 1H).

Example 32

(3S, 5S)-3-Methanesulfonylaminocarbonyl-N-[5-(thiazolidine-3-carbonyl)-pyrrolidin-3-ylmethyl]-benzamide

Example 32A

3-Methanesulfonylaminocarbonyl-benzoic acid methyl ester

To a mixture of isophthalic acid monomethyl ester (500.0 mg, 2.8 mmol), methanesulfonamide (340 mg, 3.6 mmol) and DMAP (440 mg, 3.6 mmol) in anhydrous dichloromethane (30 mL) was added 1-[3-(dimethylamino)propyl]-3-ethylcarbodiimide hydrochloride (690 mg, 3.6 mmol). The mixture was allowed to stir for 12 hours at room temperature and then concentrated under reduced pressure. The residue was chromatographed on a Biotage 40M eluting with 2% methanol/98% dichloromethane to provide the titled compound. MS (ESI) m/e 259 (M+H)$^+$, 257 (M−H)$^-$; 1H NMR (300 MHz, CD$_3$OD) δ ppm 3.36 (s, 3H) 3.95 (s, 3H) 7.64 (t, J=7.80 Hz, 1H) 8.13 (dd, J=7.80, 1.36 Hz, 1H) 8.25 (m, 1H) 8.55 (m, 1H).

Example 32B

3-Methanesulfonylaminocarbonyl-benzoic acid

A mixture of Example 32A (627 mg, 2.43 mmol) and lithium hydroxide monohydrate (112 mg, 2.67 mmol) in THF (15 mL) was stirred for 12 hours at room temperature after which the pH was adjusted to 6 by addition of 1 M HCl solution (3 mL, 3 mmol). The mixture was concentrated under reduced pressure, and the residue was partitioned between dichloromethane (30 mL) and H$_2$O (10 mL). The aqueous layer was extracted with ethyl acetate (2×20 mL), and the combined organic layers were dried (Na$_2$SO$_4$), filtered, and concentrated under reduced pressure to provide a white powder as the titled compound. MS (ESI) m/e 244 (M+H)$^+$, 242 (M−H)$^-$; 1H NMR (500 MHz, CD$_3$OD) δ ppm 3.38 (s, 3H) 7.64 (t, 1H) 8.11 (m, 1H) 8.27 (m, 1H) 8.54 (m, 1H).

Example 32C (2S, 4R)-4-[(3-Methanesulfonylaminocarbonyl-benzoylamino)-methyl]-2-(thiazolidine-3-carbonyl)-pyrrolidine-1-carboxylic acid tert-butyl ester To a solution of Example 32B (401 mg, 1.27 mmol) in anhydrous DMF (10 mL) was added triethylamine (0.3 mL), followed by Example 17D (281 mg, 1.40 mmol), HOBt (189.0 mg, 1.40 mmol) and 1-[3-(dimethylamino)propyl]-3-ethylcarbodiimide hydrochloride (269 mg, 1.40 mmol). The mixture was allowed to stir for 12 hours at room temperature and then concentrated under reduced pressure. The residue was purified by RP-HPLC to provide the titled compound. MS (ESI) m/e 541 (M+H)$^+$, 539 (M−H)$^-$; 1H NMR (400 MHz, CD$_3$OD) δ ppm 1.41 (s, 5H) 1.44(s, 4H), 1.66 (m, 1H), 2.49 (m, 1H), 2.59 (m, 1H), 3.03 (m, 1H), 3.13 (m, 1H), 3.21 (m, 1H), 3.48 (m, 2H) 3.75 (m, 2H) 3.85 (m, 1H) 4.53 (m, 2H) 4.66 (m, 1H), 7.47 (t, 1H) 7.89 (dd, 1H) 8.15 (dd, 1H) 8.45 (d, 1H).

Example 32

(3S, 5S)-3-Methanesulfonylaminocarbonyl-N-[5-(thiazolidine-3-carbonyl)-pyrrolidin-3-ylmethyl]-benzamide To a solution of Example 32C (372.1 mg, 0.69 mmol) in methanol (5 mL) was slowly added a solution of 4 M HCl in dioxane (1.6 mL, 6.4 mmol) at 0° C. over 10 minutes via addition funnel. The mixture was allowed to stir for 5 hours at room temperature and then was concentrated under reduced pressure to provide the titled compound. MS (ESI) m/e 441 (M+H)$^+$, 439 (M−H)$^-$; 1H NMR (400 MHz, CD$_3$OD) δ ppm 1.80 (m, 1H), 2.74 (m, 1H), 2.84 (m, 1H), 3.09 (m, 1H), 3.16 (t, 1H), 3.24 (m, 1H), 3.52 (dd, 2H), 3.55

(m, 1H), 3.74 (m, 1H), 3.88 (m, 1H), 4.51 (m, 1H), 4.65 (d, 1H), 4.70 (d, 1H), 7.63 (m, 1H) 8.06 (d, 1H) 8.10 (d, 1H) 8.39 (s, 1H).

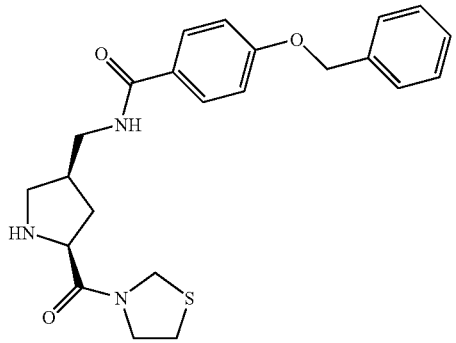

Example 33

(3S, 5S)-4-Benzyloxy-N-[5-(thiazolidine-3-carbonyl)-pyrrolidin-3-ylmethyl]-benzamide Example 33 was prepared in the same manner as Example 9, by substituting 4-benzyloxybenzoic acid for glutaranilic acid. MS (ESI) m/e 426 (M+H)$^+$; $^1$H NMR (500 MHz, pyridine-d$_5$) δ ppm 2.00 (m, 1H), 2.49 (m, 1H), 2.83 (m, 3H), 3.13 (s, 1H), 3.54 (m, 1H), 3.78 (m, 4H), 3.91 (dd, J=11.07, 7.33 Hz, 1H), 4.62 (m, 2H), 5.10 (m, 2H), 7.14 (m, J=8.42 Hz, 3H), 7.36 (m, 3H), 7.49 (d, J=7.17 Hz, 2H), 8.24 (d, J=8.42 Hz, 2H), 9.20 (m, 1H).

Example 34

(3S, 5S)-3-Imidazol-1-ylmethyl-N-[5-(thiazolidine-3-carbonyl)-pyrrolidin-3-ylmethyl]-benzamide Example 34 was prepared in the same manner as Example 28 by substituting imidazole for 1,2,4-triazole. MS (ESI) m/e 400 (M+H)$^+$; $^1$H NMR (500 MHz, CD$_3$OD): δ ppm 1.29 (s, 1H), 1.80 (d, 1H), 2.79 (m, 2H), 3.13 (m, 3H), 3.51 (m, 3H), 3.72 (m, 1H), 3.88 (dd, 1H), 4.49 (dd, 1H), 4.65 (m, 2H), 5.52 (s, 2H), 7.58 (m, 4H), 7.87 (m, 2H), 8.97 (d, 1H).

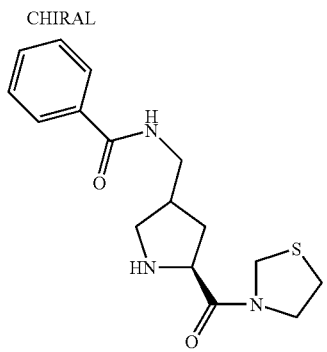

Example 35

(3S, 5S)-N-[5-(Thiazolidine-3-carbonyl)-pyrrolidin-3-ylmethyl]-benzamide

Example 35 was prepared in the same manner as described in Example 17, by substituting benzoyl chloride for pyrrolidine-1-carbonyl chloride. MS (ESI) m/e 320 (M+H)$^+$, 318 (M−H)$^-$; $^1$H NMR (400 MHz, CD$_3$OD): δ ppm 1.76-1.85 (m, 1H), 2.70-2.78 (m, 1H), 2.79-2.87 (m, 1H), 3.05 (t, 1H), 3.15(t, 1H), 3.20-3.29 (m, 1H), 3.41-3.47 (m, 1H), 3.51 (d, 2H), 3.73-3.77 (m, 1H), 3.83-3.91 (m, 1H), 4.52(dd, 1H), 4.60-4.70 (m, 2H), 7.42-7.50 (m, 2H), 7.52-7.57 (m, 1H), 7.80-7.85 (m, 2H).

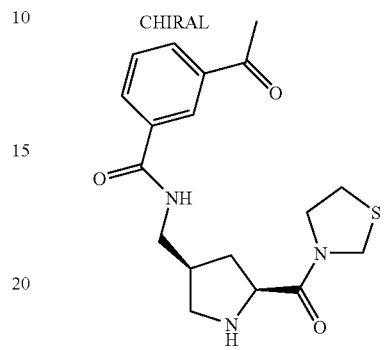

Example 36

(3S, 5S)-3-Acetyl-N-[5-(thiazolidine-3-carbonyl)-pyrrolidin-3-ylmethyl]-benzamide Example 36 was prepared in the same manner as Example 18 by substituting 3-acetylbenzoic acid for monomethyl isophthalate. MS (ESI) m/e 332 (M+H)$^+$; $^1$H NMR (500 MHz, CD$_3$OD): δ ppm 1.19 (m, 1H), 1.81 (dd, 1H), 2.37 (m, 1H), 2.64 (d, 3H), 2.74 (m, 1H), 2.83 (m, 1H), 3.05 (m, 1H), 3.16 (q, 1H), 3.24 (m, 1H), 3.52 (m, 3H), 3.74 (m, 1H), 3.88 (m, 1H), 4.52 (m, 1H), 4.69 (m, 1H), 7.63 (m, 1H), 8.07 (t, 1H), 8.18 (d, 1H), 8.44 (m, 1H).

Example 37

(3S, 5S)-Benzo[1,3]dioxole-5-carboxylic acid [5-(thiazolidine-3-carbonyl)-pyrrolidin-3-ylmethyl]-amide Example 37 was prepared in the same manner as Example 9, by substituting piperonylic acid for glutaranilic acid. MS (ESI) m/e 364 (M+H)$^+$; $^1$H NMR (500 MHz, pyridine-d$_5$) δ ppm 2.02 (m, 1H), 2.84 (m, 2H), 3.13 (d, J=8.11 Hz, 1H), 3.56 (m, 2H), 3.79 (m, 4H), 3.95 (d, J=7.80 Hz, 1H), 4.62 (m, 2H), 5.16 (m, 1H), 5.98 (m, 2H), 6.91 (m, 1H), 7.79 (m, 3H), 9.18 (s, 1H).

Example 38

(3S, 5S)-4-Methanesulfonyl-N-[5-(thiazolidine-3-carbonyl)-pyrrolidin-3-ylmethyl]-benzamide Example 38 was prepared in the same manner as Example 18 by substituting 4-methyl sulfonyl benzoic acid for monomethyl isophthalate. MS (ESI) m/e 398 (M+H)$^+$; $^1$H NMR (500 MHz, CD$_3$OD): δ ppm 1.19 (dd, 1H), 1.81 (m, 1H), 2.76 (m, 2H), 3.09 (m, 5H), 3.24 (dd, 1H), 3.55 (m, 3H), 3.75 (m, 1H), 3.88 (m, 1H), 4.52 (m, 1H), 4.66 (m, 2H), 8.05 (m, 4H).

Example 39

(3S, 5S)-3-Dimethylamino-N-[5-(pyrrolidine-1-carbonyl)-pyrrolidin-3-ylmethyl]-benzamide

Example 39A (2S, 4R)-4-Hydroxy-2-(pyrrolidine-1-carbonyl)-pyrrolidine-1-carboxylic acid tert-butyl ester Trans-Boc-L-hydroxyproline (3 g, 13.0 mmol), 1-[3-(dimethylamino)propyl]-3-ethylcarbodiimide hydrochloride (2.98 g, 15.56 mmol) and HOBt (2.10 g, 15.56 mmol) were dissolved in DMF/dichloromethane (25 mL/5 mL) followed by the addition of triethylamine (16.3 mL) and pyrrolidine (0.925 g, 13.0 mmol). The mixture was stirred at room temperature for 24 hours, concentrated under reduced pressure and the resulting liquid was purified with flash silica gel chromatography eluting with 100% ethyl acetate to provide the titled compound. MS (ESI) m/e 285(M+H)$^+$; $^1$H NMR (300 MHz, CDCl$_3$) δ ppm 1.40 (s, 5H) 1.45 (s, 4H) 1.86 (m, 2H) 1.99 (m, 2H) 2.08 (m, 1H) 2.20 (m, 2H) 3.41 (m, 2H) 3.55 (m, 2H) 3.69 (m, 1H) 4.53 (m, 1H) 4.61 (m, 1H).

Example 39B (2S, 4S)-4-Cyano-2-(pyrrolidine-1-carbonyl)-pyrrolidine-1-carboxylic acid tert-butyl ester To a mixture of Example 39A (1.88 g, 6.6 mmol) and triethylamine (0.92 mL, 6.6 mmol) in THF (20 mL) at 0° C. under nitrogen was added methanesulfonyl chloride (1.51 g, 13.2 mmol). The mixture was allowed to warm up to room temperature and stirred for 12 hours after which it was concentrated under reduced pressure, and the residue was partitioned between water and ethyl acetate. The aqueous layer was extracted with ethyl acetate (3×30 mL) and the combined organic layers were dried (MgSO$_4$), filtered and concentrated under reduced pressure to provide a yellow liquid. The yellow liquid was taken up in 100 mL of dry DMF under nitrogen and tetrabutylammonium cyanide (5 g, 20 mmol) was added to the solution. The mixture was heated to 50° C. for 60 hours after which the mixture was poured into cold water and extracted with ethyl acetate (3×25 mL). The combined organic layers were dried (MgSO$_4$), filtered, concentrated under reduced pressure and purified by flash silica gel chromatography eluting with 50% ethyl acetate/50% hexane to provide the titled compound. MS (DCI/NH$_3$) m/e 294 (M+H)$^+$; $^1$H NMR (300 MHz, CDCl$_3$) δ ppm 1.43 (s, 5H) 1.49 (s, 4H) 1.86 (m, 2H) 1.99 (m, 2H) 2.03 (m, 1H) 2.10 (m, 2H) 3.40 (m, 2H) 3.52 (m, 2H) 3.69 (m, 1H) 4.58 (m, 1H) 4.65 (m, 1H).

Example 39C (2S, 4R)-4-Aminomethyl-2-(pyrrolidine-1-carbonyl)-pyrrolidine-1-carboxylic acid tert-butyl ester Example 39B (1.45 g, 5 mmol) was taken up in a solution of aqueous ammonia in methanol (60 mL, 20% v/v). Raney nickel 2800 (14.6 g, 0.14 mmol) that had been washed three times with methanol was added to the NH$_3$-methanol solution at room temperature and the mixture was shaken under 60 psi of hydrogen for 2.5 hours. The mixture was filtered through a nylon membrane and concentrated under reduced pressure. The residue was purified by silica gel chromatography with 10% methanol/90% dichloromethane/0.2% ammonium hydroxide. MS (ESI) m/e 298 (M+H)$^+$; $^1$H NMR (300 MHz, CD$_3$OD) δ ppm 1.43 (m, 9H) 1.62 (dd, 1H) 1.89 (m, 2H) 2.02 (m, 2H) 2.54 (m, 2H) 3.04 (m, 1H) 3.23 (m, 1H) 3.46 (m, 4H) 3.63 (m, 1H) 3.77 (m, 1H) 4.52 (m, 1H).

Example 39

(3S, 5S)-3-Dimethylamino-N-[5-(pyrrolidine-1-carbonyl)-pyrrolidin-3-ylmethyl]-benzamide To a solution of Example 39C (32 mg, 0.11 mmol) in anhydrous dichloromethane (5 mL) was added triethylamine (0.14 mL) followed by 3-dimethylaminobenzoyl chloride (0.014 mL, 0.11 mmol). The mixture was allowed to stir for 12 hours at room temperature, concentrated under reduced pressure, and the residue was partitioned between ethyl acetate (30 mL) and H$_2$O (10 mL). The aqueous layer was extracted with ethyl acetate (2×20 mL), and the combined organic layers were dried (Na$_2$SO$_4$), filtered, and concentrated under reduced pressure to provide a brown oil.

To a mixture of the brown oil in anhydrous dichloromethane (2 mL) was added trifluoroacetic acid (0.075 mL) in dichloromethane (0.075 mL). The mixture was stirred for 8 hours at room temperature, concentrated under reduced pressure and purified by RP-HPLC to provide the titled compound. MS (ESI) m/e 345 (M+H)$^+$, 343 (M−H)$^−$; $^1$H NMR (400 MHz, CD$_3$OD) δ ppm 1.78 (m, 1H) 1.91 (m, 2H) 2.02 (m, 2H) 2.73 (m, 1H) 2.85 (m, 1H) 3.20 (m, 6H) 3.28 (m, 1H) 3.45 (m, 3H) 3.53 (m, 2H) 3.58 (m, 2H) 4.59 (m, 1H) 7.52 (m, 2H) 7.66 (m, 1H) 7.81 (m, 1H).

Example 40

(3S, 5S)-4-Phenoxy-N-[5-(thiazolidine-3-carbonyl)-pyrrolidin-3-ylmethyl]-benzamide Example 40 was prepared in the same manner as Example 9, by substituting 4-phenoxybenzoic acid for glutaranilic acid. MS (ESI) m/e 412 (M+H)$^+$; $^1$H NMR (500 MHz, pyridine-d$_5$) δ ppm 2.02 (m, 1H), 2.84 (m, 1H), 3.20 (m, 1H), 3.57 (m, 1H), 3.80 (m, 6H), 3.97 (dd, J=10.76, 7.33 Hz, 1H), 4.62 (m, 2H), 5.18 (m, 1H), 7.11 (m, 5H), 7.37 (t, J=8.11 Hz, 2H), 7.92 (m, 2H), 8.23 (d, J=8.73 Hz, 2H), 9.33 (t, J=5.61 Hz, 1H).

Example 41

(3S, 5S)-3-Amino-N-[5-(thiazolidine-3-carbonyl)-pyrrolidin-3-ylmethyl]-benzamide Example 41 was prepared in the same manner as Example 9, by substituting N-Boc-3-aminobenzoic acid for glutaranilic acid. MS (ESI) m/e 335 (M+H)$^+$; $^1$H NMR (500 MHz, pyridine-d$_5$) δ ppm 1.99 (m, 2H), 2.84 (m, 7H), 3.14 (d, J=8.73 Hz, 1H), 3.68 (m, 7H), 4.61 (m, 2H), 5.16 (m, 1H), 7.04 (d, J=5.61 Hz, 1H), 7.51 (d, J=7.80 Hz, 1H), 7.79 (s, 1H), 9.16 (m, 1H).

Example 42

(3S, 5S)-4-Hydroxy-N-[5-(pyrrolidine-1-carbonyl)-pyrrolidin-3-ylmethyl]-benzamide To a solution Example 39C (32 mg, 0.11 mmol), 4-hydroxybenzoic acid (14 mg, 0.1 mmol), HOBt (18 mg, 0.13 mmol) in anhydrous DMF (5 mL) was added 1-[3-(dimethylamino)propyl]-3-ethylcarbodiimide hydrochloride (25 mg, 0.13 mmol) and triethylamine (0.03 mL, 0.18 mmol). The mixture was stirred for 12 hours at room temperature, and concentrated under reduced pressure to provide a yellow oil.

To a solution of the yellow oil residue in anhydrous dichloromethane (2 mL) was added trifluoroacetic acid in dichloromethane solution (0.15 mL, 50% trifluoroacetic acid/50% dichloromethane, 1 mmol). The mixture was stirred for 8 hours at room temperature, and then it was concentrated under reduced pressure and purified by RP-HPLC to provide the titled compound. MS (DCI/NH$_3$) m/e 318 (M+H)$^+$; $^1$H NMR (500 MHz, CD$_3$OD) δ ppm 1.77 (m, 1H) 1.89 (m, 2H) 1.99 (m, 2H) 2.73 (m, 1H) 2.83 (m, 1H) 3.26 (dd, 1H) 3.33 (m, 1H) 3.43 (m, 2H) 3.49 (m, 2H) 3.56 (m, 2H) 4.58 (m, 1H) 6.84 (d, 2H) 7.87 (d, 2H).

Example 43

(3S, 5S)-3-Hydroxy-N-[5-(thiazolidine-3-carbonyl)-pyrrolidin-3-ylmethyl]-benzamide Example 43 was prepared in the same manner as Example 9, by substituting 3-hydroxybenzoic acid for glutaranilic acid. MS (ESI) m/e 336 (M+H)$^+$; $^1$H NMR (500 MHz, pyridine-d$_5$) δ ppm 2.01 (m, 1H), 2.84 (m, 4H), 3.15 (m, 1H), 3.54 (m, 2H), 3.80 (m, 4H), 3.93 (m, 1H), 4.61 (m, 2H), 5.17 (m, 1H), 7.32 (m, 2H), 7.75 (d, J=7.48 Hz, 1H), 8.11 (m, 1H), 9.31 (d, J=5.61 Hz, 1H).

Example 44

(3S, 5S-N-[5-(Pyrrolidine-1-carbonyl)-pyrrolidin-3-ylmethyl]-isophthalamic acid

Example 44 was prepared in the same manner as described in Example 18 and Example 22 by substituting Example 17D with Example 39C. MS (ESI) m/e 346 (M+H)$^+$; $^1$H NMR (500 MHz, CD$_3$OD) δ ppm 1.77 (m, 1H) 1.93 (m, 2H) 2.01 (m, 2H) 2.72 (m, 1H) 2.81 (m, 1H) 3.23 (dd, 1H) 3.33 (m, 1H) 3.45 (m, 2H) 3.51 (m, 4H) 4.54 (t, 1H) 7.60 (m, 1H) 8.05 (d, 1H) 8.20 (d, 1H) 8.49 (s, 1H) 8.85 (s, 1H).

Example 45

(3S, 5S)-3-Dimethylamino-N-[5-(thiazolidine-3-carbonyl)-pyrrolidin-3-ylmethyl]-benzamide Example 45 was prepared in the same manner as Example 9, by substituting 3-dimethylaminobenzoic acid for glutaranilic acid. MS (ESI) m/e 363 (M+H)$^+$; $^1$H NMR (500 MHz, pyridine-d$_5$) δ ppm 2.01 (m, 1H), 2.82 (m, 10H), 3.16 (m, 1H), 3.55 (m, 2H), 3.76 (m, 4H), 3.96 (m, 1H), 4.61 (m, 2H), 5.18 (m, 1H), 6.86 (dd, J=8.11, 2.50 Hz, 1H), 7.33 (m, 1H), 8.55 (m, 1H), 9.30 (m, 1H).

Example 46

(3S, 5S)-3-Methoxy-N-[5-(thiazolidine-3-carbonyl)-pyrrolidin-3-ylmethyl]-benzamide Example 46 was prepared in the same manner as Example 9, by substituting 3-methoxybenzoic acid for glutaranilic acid. MS (ESI) m/e 350 (M+H)$^+$; $^1$H NMR (500 MHz, pyridine-d$_5$) δ ppm 2.01 (m, 1H), 2.84 (m, 3H), 3.16 (s, 1H), 3.68 (m, 9H), 3.96 (m, 1H), 4.62 (m, 2H), 5.17 (m, 1H), 7.10 (dd, J=8.11, 2.18 Hz, 1H), 7.35 (m, 1H), 7.82 (m, 2H), 9.40 (d, J=5.61 Hz, 1H).

Example 47

(3S, 5S)-N-[5-(Pyrrolidine-1-carbonyl)-pyrrolidin-3-ylmethyl]-isophthalamic acid methyl ester Example 47 was prepared in the same manner as Example 18 by substituting Example 17D with Example 39C. MS (ESI) m/e 360 (M+H)$^+$; $^1$H NMR (500 MHz, CD$_3$OD): δ ppm 1.75 (m, 1H), 1.93 (m, 2H), 2.01 (m, 2H), 2.72 (m, 2H), 3.22 (dd, 1H), 3.51 (m, 7H), 3.94 (s, 3H), 4.49 (t, 1H), 4.80 (m, 2H), 7.61 (m, 1H), 8.06 (m, 1H), 8.19 (dd, 1H), 8.48 (m, 1H).

Example 48

(3S, 5S)-Quinoxaline-6-carboxylic acid [5-(thiazolidine-3-carbonyl)-pyrrolidin-3-ylmethyl]-amide Example 48 was prepared in the same manner as Example 25 by substituting 8-quinoxaline carbonyl chloride for 2,3-dihydro-1,4-benzodioxine-6-carbonyl chloride. MS (ESI) m/e 372 (M+H)$^+$; $^1$H NMR (500 MHz, CD$_3$OD): δ ppm 1.86 (m, 1H), 2.78 (m, 1H), 2.87 (m, 1H), 3.08 (m, 1H), 3.17 (m, 1H), 3.28 (d, 1H), 3.59 (m, 4H), 3.76 (m, 1H), 3.89 (m, 1H), 4.53 (t, 1H), 4.68 (m, 2H), 8.19 (d, 1H), 8.25 (m, 1H), 8.58 (m, 1H), 8.97 (d, 2H).

Example 49

(3S, 5S)-2-Amino-N-[5-(thiazolidine-3-carbonyl)-pyrrolidin-3-ylmethyl]-benzamide Example 49 was prepared in the same manner as Example 9, by substituting N-Boc-2-aminobenzoic acid for glutaranilic acid. MS (ESI) m/e 335 (M+H)$^+$; $^1$H NMR (500 MHz, pyridine-d$_5$) δ ppm 2.01 (m, 1H), 2.83 (m, 5H), 3.12 (s, 1H), 3.71 (m, 8H), 4.63 (m, 2H), 5.16 (m, 1H), 6.60 (t, J=7.49 Hz, 1H), 7.01 (m, 1H), 7.87 (m, 1H), 9.12 (s, 1H).

Example 50

(3S, 5S)-Benzo[1,3]dioxole-5-carboxylic acid [5-(pyrrolidine-1-carbonyl)-pyrrolidin-3-ylmethyl]-amide Example 50 was prepared in the same manner as Example 42 by substituting Benzo[1,3]dioxole-5-carboxylic acid for 4-hydroxybenzoic acid. MS (DCI/NH$_3$) m/e 346 (M+H)$^+$; $^1$H NMR (500 MHz, CD$_3$OD) δ ppm 1.75 (m, 1H) 1.91 (m, 2H) 2.00 (m, 2H) 2.70 (m, 1H) 2.78 (m, 1H) 3.22 (dd, 1H) 3.45 (m, 4H) 3.52 (m, 2H) 3.58 (m, 1H) 4.56 (t, 1H) 6.03 (m, 2H) 6.88 (m, 1H) 7.30 (m, 1H) 7.41 (m, 1H).

Example 51

(3S, 5S)-2,3-Dihydro-benzofuran-5-carboxylic acid [5-(pyrrolidine-1-carbonyl)-pyrrolidin-3-ylmethyl]-amide Example 51 was prepared in the same manner as Example 25 by substituting 2,3-dihydro-1-benzofuran-5-carbonyl chloride and Example 39C for 2,3-dihydro-1,4-benzodioxine-6-carbonyl chloride and Example 17D respectively. MS (ESI) m/e 344 (M+H)$^+$; $^1$H NMR (500 MHz, CD$_3$OD): δ ppm 1.75 (m, 1H), 1.93 (m, 2H), 2.01 (m, 2H), 2.70 (m, 1H), 2.78 (m, 1H), 3.22 (m, 3H), 3.47 (m, 7H), 3.56 (m, 1H), 4.53 (t, 1H), 4.62 (t, 2H), 6.77 (d, 1H), 7.63 (m, 1H), 7.70 (s, 1H).

Example 52

(3S, 5S)-Pyridine-2-carboxylic acid [5-(thiazolidine-3-carbonyl)-pyrrolidin-3-ylmethyl]-amide Example 52 was prepared in the same manner as Example 9, by substituting pyridine-2-carboxylic acid for glutaranilic acid. MS (ESI) m/e 321 (M+H)+; 1H NMR (500 MHz, pyridine-d5) δ ppm 1.80 (m, 1H), 2.60 (m, 4H), 2.93 (m, 1H), 3.32 (m, 1H), 3.56 (m, 4H), 3.73 (m, 1H), 4.39 (m, 2H), 4.96 (m, 1H), 7.13 (m, 1H), 7.52 (t, J=7.63 Hz, 1H), 8.10 (dd, J=7.48, 3.81 Hz, 1H), 8.31 (m, 1H), 9.24 (m, 1H).

Example 53

(3S, 5S)-1-Methyl-1H-pyrrole-2-carboxylic acid [5-(thiazolidine-3-carbonyl)-pyrrolidin-3-ylmethyl]-amide Example 53 was prepared in the same manner as Example 17 by substituting 1-methyl-1H-pyrrole-2-carbonyl chloride for pyrrolidine-1-carbonyl chloride. MS (ESI) m/e 323 (M+H)+, 321 (M−H)−; 1H NMR (400 MHz, CD3OD) δ ppm 1.78 (m, 1H) 2.73 (m, 2H) 3.06 (m, 1H) 3.15 (m, 1H) 3.21 (m, 1H) 3.48 (m, 1H) 3.72 (m, 1H) 3.85 (s, 3H) 4.50 (m, 1H) 4.65 (m, 2H) 6.05 (dd, 1H) 6.74 (m, 1H) 6.82 (d, 1H).

Example 54

(3S, 5S)-1-Phenyl-cyclopropanecarboxylic acid [5-(thiazolidine-3-carbonyl)-pyrrolidin-3-ylmethyl]-amide Example 54 was prepared in the same manner as Example 9, by substituting 1-phenyl-1-cyclopropanecarboxylic acid for glutaranilic acid. MS (ESI) m/e 360 (M+H)+; 1H NMR (500 MHz, pyridine-d5) δ ppm 1.01 (m, 4H), 1.78 (m, 2H), 2.58 (m, 1H), 2.88 (m, 5H), 3.33 (t, J=10.53 Hz, 1H), 3.47 (t, J=6.41 Hz, 2H), 3.57 (m, 1H), 3.80 (m, 2H), 4.62 (m, 2H), 4.99 (m, 1H), 7.08 (m, 1H), 7.41 (m, 4H).

Example 55

(3S, 5S)-Thiazole-4-carboxylic acid [5-(thiazolidine-3-carbonyl)-pyrrolidin-3-ylmethyl]-amide

Example 55A (2S, 4R)-4-{[(Thiazole-4-carbonyl)-amino]-methyl}-2-(thiazolidine-3-carbonyl)-pyrrolidine-1-carboxylic acid tert-butyl ester To a solution of thiazole-4-carboxylic acid (2.25 g, 17.6 mmol) and HOBt (2.60 g, 19.2 mmol) in anhydrous DMF (80 mL) at 0° C. was added 1-[3-(dimethylamino)propyl]-3-ethylcarbodiimide hydrochloride (3.69 g, 19.2 mmol) followed by the dropwise addition of a solution of Example 17D (5.07 g, 16 mmol) in anhydrous DMF (50 mL) over 10 minutes, after which anhydrous triethylamine (4.45 mL, 32 mmol) was added to the mixture via syringe. The mixture was allowed to stir for 12 hours at room temperature, concentrated under reduced pressure and the residue was partitioned between ethyl acetate (100 mL) and H2O (30 mL). The aqueous layer was extracted with ethyl acetate (2×50 mL), and the combined organic layers were dried (Na2SO4), filtered, and concentrated to provide a yellow solid. The yellow solid was crystallized from ethyl acetate (30 mL). The white crystals were dried under vacuum at 40° C. for 12 hours to provide a white powder (4.8 g) as the titled compound. MS (ESI) m/e 427 (M+H)+, 425 (M−H)−; 1H NMR (500 MHz, CD3OD) δ ppm 1.41 (s, 5H) 1.44(s, 4H), 1.66 (m, 1H), 2.49 (m, 1H), 2.59 (m, 1H), 3.03 (m, 1H), 3.13 (m, 1H), 3.21 (m, 1H), 3.48 (m, 2H) 3.75 (m, 2H) 3.85 (m, 1H) 4.53 (m, 2H) 4.66 (m, 1H), 8.25 (s, 1H), 8.99 (s, 1H).

Example 55

(3S, 5S)-Thiazole-4-carboxylic acid [5-(thiazolidine-3-carbonyl)-pyrrolidin-3-ylmethyl]-amide To a solution of Example 55A (4.8 g, 11.3 mmol) in anhydrous methanol (10 mL) a solution of 4 M HCl in dioxane (22.5 mL, 90 mmol) was slowly added via addition funnel at 0° C. over 30 minutes. The mixture was stirred for 4 hours at room temperature and concentrated under reduced pressure to provide a yellow oil. The oil was dissolved in water, frozen, and lyophilized to provide a white power as the titled product. MS (ESI) m/e 327 (M+H)+, 325 (M−H)−; 1H NMR (500 MHz, CD3OD) δ ppm 1.80 (m, 1H), 2.74 (m, 1H), 2.84 (m, 1H), 3.09 (m, 1H), 3.16 (t, 1H), 3.24 (m, 1H), 3.52 (dd, 2H), 3.55 (m, 1H), 3.74 (m, 1H), 3.88 (m, 1H), 4.51 (m, 1H), 4.65 (d, 1H), 4.70 (d, 1H), 8.33 (s, 1H) 9.11 (s, 1H).

Example 56

(3S, 5S)-Thiophene-3-carboxylic acid [5-(thiazolidine-3-carbonyl)-pyrrolidin-3-ylmethyl]-amide Example 56 was prepared in the same manner as Example 9, by substituting thiophene-3-carboxylic acid for glutaranilic acid. MS (ESI) m/e 326 (M+H)+; 1H NMR (500 MHz, pyridine-d5) δ ppm 1.75 (m, 1H), 2.26 (m, 3H), 2.59 (m, 3H), 2.87 (m, 1H), 3.30 (m, 1H), 3.56 (m, 4H), 4.38 (m, 2H), 4.90 (m, 1H), 7.62 (m, 1H), 8.13 (m, 1H), 9.03 (m, 1H).

Example 57

(3S, 5S)-6-Chloro-N-[5-(thiazolidine-3-carbonyl)-pyrrolidin-3-ylmethyl]-nicotinamide Example 57 was prepared in the same manner as Example 17 by substituting 6-chloro-nicotinoyl chloride for pyrrolidine-1-carbonyl chloride. MS (ESI) m/e 355 (M+H)+, 353 (M−H)−; 1H NMR (400 MHz, CD3OD) δ ppm 1.80 (m, 1H) 2.74 (m, 1H) 2.83 (m, 1H) 3.16 (m, 2H) 3.23 (m, 1H) 3.52 (m, 2H) 3.56 (m, 1H) 3.75 (m, 1H) 3.89 (m, 1H) 4.51 (m, 1H) 4.67 (m, 2H) 7.57 (d, 1H) 8.20 (dd, 1H) 8.80 (d, 1H).

Example 58

(3S, 5S)-1H-Indole-3-carboxylic acid [5-(thiazolidine-3-carbonyl)-pyrrolidin-3-ylmethyl]-amide Example 58 was prepared in the same manner as Example 9, by substituting indole-3-carboxylic acid for glutaranilic acid. MS (ESI) m/e 359 (M+H)+; 1H NMR (500 MHz, pyridine-d5) δ ppm 1.83 (m, 1H), 2.26 (m, 3H), 2.61 (m, 3H), 2.92 (m, 1H), 3.37 (m, 1H), 3.55 (m, 3H), 3.72 (m, 1H), 4.40 (m, 2H), 4.93 (m, 1H), 7.15 (m, 3H), 8.12 (m, 1H), 8.69 (m, 1H), 12.48 (m, 1H).

Example 59

(3S, 5S)-3-Methyl-thiophene-2-carboxylic acid [5-(pyrrolidine-1-carbonyl)-pyrrolidin-3-ylmethyl]-amide Example 59 was prepared in the same manner as Example 42 by substituting 3-methyl-thiophene-2-carboxylic acid for 4-hydroxybenzoic acid. MS (DCI/NH$_3$) m/e 322 (M+H)$^+$; 1H NMR (500 MHz, CD$_3$OD) δ ppm 1.75 (m, 1H) 1.91 (m, 2H) 2.01 (m, 2H) 2.46 (m, 3H) 2.70 (m, 1H) 2.78 (m, 1H) 3.22 (dd, 1H) 3.46 (m, 2H) 3.51 (m, 2H) 3.58 (m, 1H) 4.57 (t, 1H) 6.94 (m, 1H) 7.44 (m, 1H).

Example 60

(3S, 5S)-Furan-2-carboxylic acid [5-(thiazolidine-3-carbonyl)-pyrrolidin-3-ylmethyl]-amide Example 60 was prepared in the same manner as Example 17 by substituting 2-furoyl chloride for pyrrolidine-1-carbonyl chloride. MS (ESI) m/e 310 (M+H)$^+$ 308 (M−H)$^-$; $^1$H NMR (400 MHz, CD$_3$OD) δ ppm 1.79 (m, 1H) 2.71 (m, 1H) 2.76 (m, 1H) 3.07 (m, 1H) 3.16 (m, 2H) 3.46 (m, 2H) 3.51 (m, 1H) 3.73 (m, 1H) 3.87 (m, 1H) 4.50 (m, 1H) 4.63 (m, 2H) 6.59 (m, 1H) 7.15 (m, 1H) 7.67 (m, 1H).

Example 61

(3S, 5S)-Pyrazine-2-carboxylic acid [5-(thiazolidine-3-carbonyl)-pyrrolidin-3-ylmethyl]-amide Example 61 was prepared in the same manner as Example 9, by substituting pyrazine-2-carboxylic acid for glutaranilic acid. MS (ESI) m/e 322 (M+H)$^+$; $^1$H NMR (500 MHz, pyridine-d$_5$) δ ppm 1.83 (m, 1H), 2.27 (m, 2H), 2.59 (m, 2H), 2.69 (m, 1H), 2.94 (m, 1H), 3.34 (m, 2H), 3.57 (m, 3H), 3.71 (m, 1H), 4.40 (m, 2H), 4.86 (m, 1H), 8.24 (m, 1H), 9.36 (m, 2H).

Example 62

(3S, 5S)-3-Methyl-thiophene-2-carboxylic acid [5-(thiazolidine-3-carbonyl)-pyrrolidin-3-ylmethyl]-amide Example 62 was prepared in the same manner as Example 9, by substituting 3-methylthiophene-2-carboxylic acid for glutaranilic acid. MS (ESI) m/e 340 (M+H)$^+$; $^1$H NMR (500 MHz, pyridine-d$_5$) δ ppm 1.80 (m, 1H), 2.29 (m, 3H), 2.40 (m, 2H), 2.59 (m, 2H), 2.72 (m, 1H), 2.91 (m, 1H), 3.30 (m, 1H), 3.37 (m, 1H), 3.52 (m, 2H), 3.60 (m, 1H), 3.74 (m, 1H), 4.42 (m, 1H), 4.95 (m, 1H), 6.68 (m, 1H), 7.18 (m, 1H), 8.69 (m, 1H).

Example 63

(3S, 5S)-Thiazole-4-carboxylic acid [5-(pyrrolidine-1-carbonyl)-pyrrolidin-3-ylmethyl]-amide Example 63 was prepared in the same manner as Example 42 by substituting thiazole-4-carboxylic acid for 4-hydroxybenzoic acid. MS (DCI/NH$_3$) m/e 309 (M+H)$^+$; 1H NMR (500 MHz, CD$_3$OD) δ ppm 1.78 (m, 1H) 1.90 (m, 2H) 2.01 (m, 2H) 2.72 (m, 1H) 2.83 (m, 1H) 3.25 (m, 1H) 3.44 (m, 2H) 3.52 (m, 3H) 3.58 (m, 2H) 4.58 (t, 1H) 8.27 (d, 1H) 9.01 (d, 1H).

Example 64

(3S, 5S)-Cyclohexanecarboxylic acid [5-(pyrrolidine-1-carbonyl)-pyrrolidin-3-ylmethyl]-amide

Example 64A (2S, 4R)-4-[(Cyclohexanecarbonyl-amino)-methyl]-2-(pyrrolidine-1-carbonyl)-pyrrolidine-1-carboxylic acid tert-butyl ester To a stirred solution of (2S, 4R)-4-aminomethyl-2-(pyrrolidine-1-carbonyl)pyrrolidine-1-carboxylic acid tert-butyl ester (0.15 g, 0.51 mmol, Example 39C) in dichloromethane (2 mL) at room temperature was added cyclohexanecarbonyl chloride (0.092 g, 0.65 mmol) and triethylamine (0.10 mL, 0.75 mmol). The mixture was stirred at room temperature for 12 hours, concentrated under reduced pressure and the residue taken up in water and extracted with ethyl acetate (2×). The combined ethyl acetate layers were washed consecutively with saturated aqueous NaHCO$_3$, 10% KHSO$_4$ (aq), brine, dried (MgSO$_4$), filtered and concentrated under reduced pressure. The residue was purified by flash chromatography with 30-40% ethyl acetate:hexane to provide the title compound. MS (CI) m/z 408 (M+1)$^+$; $^1$H NMR (300 MHz, CDCl$_3$) δ ppm 4.40-4.28 (m, 1H), 3.88-3.66 (m, 2H), 3.56-3.25 (m, 4H), 3.22-3.16 (m, 2H), 2.57 (m, 2H), 2.55 (m, 1H), 1.99-1.61, (m, 13H), 1.41 (m, 9H), 1.51 (m, 2H).

Example 64

(3S, 5S)-Cyclohexanecarboxylic acid [5-(pyrrolidine-1-carbonyl)-pyrrolidin-3-ylmethyl]-amide Example 64A (0.038 g, 0.064 mmol) and 4 M HCl in dioxane (3 mL) were stirred at room temperature for 3 hours. Volatiles were evaporated under reduced pressure. Diethyl ether was added to the residue, and the formed precipitate was filtered. The solid was washed several times with diethyl ether (50 mL) and was dried under reduced pressure to provide title compound. MS (CI) m/z 303 (M+1)$^+$; $^1$H NMR (300 MHz, methanol-d4): δ ppm 9.89 (bs, 1H), 8.58 (m, 1H), 7.96 (m, 2H), 7.46 (m, 2H), 4.36-4.47 (m, 1H), 3.50-3.57(m, 1H), 3.27-3.44 (m, 7H), 3.01 (m, 1H), 2.70-2.57 (m, 2H), 2.42-2.52 (m, 4H).

Example 65

(2S, 4R)-(4-{[(Pyridin-2-ylmethyl)-amino]-methyl}-pyrrolidin-2-yl)-thiazolidin-3-yl-methanone To a solution of Example 17D (31 mg, 0.1 mmol) in anhydrous dichloromethane (5 mL) was slowly added 2-pyridinecarboxaldehyde (11 mg, 0.1 mmol) and the mixture was allowed to stir for 2 hours at room temperature. Polymer supported NaBH$_3$CN resin (100 mg, 0.4 mmol) was added and the mixture was allowed to shake for 12 hours, filtered, and concentrated under reduced pressure to provide a yellow oil.

To a solution of the yellow oil residue in anhydrous dichloromethane (2 mL) was added trifluoroacetic acid in dichloromethane solution (0.15 mL, 50% trifluoroacetic acid/50% dichloromethane, 1 mmol) via syringe. The mixture was allowed to stir for 8 hours at room temperature, concentrated under reduced pressure, and purified with RP-HPLC to provide the titled compound. MS (ESI) m/e 307 (M+H)$^+$; $^1$H NMR (400 MHz, CD$_3$OD) δ ppm 1.83 (m, 1H) 2.86 (m, 1H) 2.89 (m, 1H) 2.96 (m, 2H) 3.15 (m, 2H) 3.70 (m, 2H) 3.78 (m, 1H) 3.90 (m, 2H) 4.52 (m, 1H) 4.65 (m, 1H) 4.72 (m, 2H) 7.17 (dd, 1H) 7.41 (m, 1H) 7.46 (m, 1H) 7.87 (dd, 1H).

Example 66

(2S, 4S)-(4-{[Bis-(3-chloro-benzyl)-amino]-methyl}-pyrrolidin-2-yl)-thiazolidin-3-yl-methanone To a solution of Example 17D (31 mg, 0.1 mmol) in anhydrous ethyl acetate (5 mL) was added 3-chlorobenzaldehyde (32 mg, 0.2 mol) via syringe. The mixture was allowed to stir for 2 hours at room temperature after which polymer supported NaBH$_3$CN resin (100 mg, 0.4 mmol) was added to the mixture. The mixture was allowed to shake for 12 hours, the resin was removed by filtration, and the mixture was concentrated under reduced pressure to provide a yellow oil.

To a solution of the yellow oil in anhydrous dichloromethane (2 mL) was added trifluoroacetic acid (0.075 mL) in dichloromethane (0.075 mL) and the mixture stirred for 8 hours at room temperature. The mixture was concentrated under reduced pressure and purified by RP-HPLC to provide the titled compound. MS (ESI) m/e 464 (M+H)$^+$; $^1$H NMR (500 MHz, CD$_3$OD) δ ppm 1.49 (m, 1H) 2.68 (m, 2H) 2.78 (m, 1H) 2.95 (m, 1H) 3.06 (m, 2H) 3.16 (m, 1H) 3.51 (m, 1H) 3.67 (m, 1H) 3.75 (m, 4H) 3.85 (m, 1H) 4.45 (m, 1H) 4.59 (m, 2H) 7.30 (m, 4H) 7.35 (m, 2H) 7.40 (m, 2H).

Example 67

(3S, 5S)-4-{[5-(Thiazolidine-3-carbonyl)-pyrrolidin-3-ylmethyl]-sulfamoyl}-benzoic acid To a solution of Example 17D (32 mg, 0.1 mmol) in anhydrous THF (5 mL) was added N,N-diisopropylethylamine (0.035 mL, 0.2 mmol) followed by 4-chlorosulfonylbenzoic acid (20.92 mg, 0.12 mmol). The mixture was stirred for 8 hours at room temperature and concentrated under reduced pressure. The residue was taken up in anhydrous dichloromethane (3 mL) and trifluoroacetic acid (0.075 mL) in dichloromethane (0.075 mL) was added and the mixture was allowed to stir for 5 hours at room temperature. The mixture was concentrated under reduced pressure and purified using RP-HPLC to provide the titled compound. MS (ESI) m/e 400 (M+H)$^+$, 398 (M−H)$^-$; $^1$H NMR (500 MHz, CD$_3$OD) δ ppm 1.78 (m, 1H) 2.65 (m, 1H) 3.00 (m, 2H) 3.08 (m, 1H) 3.14 (m, 1H) 3.20 (m, 1H) 3.49 (m, 1H) 3.60 (m, 1H) 3.73 (m, 1H) 3.88 (m, 1H) 4.50 (m, 1H) 4.66 (m, 2H) 7.95 (d, 2H) 8.19 (d, 2H).

Example 68

(3S, 5S)-[5-(Thiazolidine-3-carbonyl)-pyrrolidin-3-ylmethyl]-carbamic acid phenyl ester To a solution of Example 17D (32 mg, 0.1 mmol) in anhydrous THF (5 mL) was added N,N-diisopropylethylamine (0.035 mL, 0.2 mmol), followed by phenyl chloroformate (17.22 mg, 0.11 mmol). The mixture was stirred for 8 hours at room temperature and concentrated under reduced pressure. The residue was taken up in anhydrous dichloromethane (3 mL) and trifluoroacetic acid (0.075 mL) in dichloromethane (0.075 mL) were added. The mixture was stirred for 5 hours at room temperature, concentrated under reduced pressure and purified using RP-HPLC to provide the titled compound. MS (ESI) m/e 336 (M+H)$^+$; 1H NMR (400 MHz, CD$_3$OD) δ ppm 1.77 (m, 1H) 2.69 (m, 2H) 3.07 (m, 1H) 3.17 (m, 2H) 3.25 (m, 1H) 3.52 (m, 2H) 3.75 (m, 1H) 3.88 (m, 1H) 4.52 (m, 1H) 4.66 (m, 2H) 7.10 (d, 2H) 7.21 (t, 1H) 7.37 (t, 2H).

Example 69

(3S, 5S)-[5-(Thiazolidine-3-carbonyl)-pyrrolidin-3-ylmethyl]-carbamic acid 2-chloro-benzyl ester Example 69 was prepared in the same manner as Example 68 by substituting 2-chlorobenzyl chloroformate for phenyl chloroformate. MS (ESI) m/e 384 (M+H)$^+$, 382 (M−H)$^-$; $^1$H NMR (300 MHz, CD$_3$OD) δ ppm 1.70 (d, J=3.05 Hz, 1H) 2.66 (m, 2H) 3.03 (m, 1H) 3.14 (m, 2H) 3.25 (m, 2H) 3.48 (m, 1H) 3.69 (m, 1H) 3.87 (m, 1H) 4.50 (m, 1H) 4.63 (m, 2H) 5.19 (s, 2H) 7.32 (m, 2H) 7.42 (m, 2H).

Example 70

(3S, 5S)-Benzo[1,3]dioxole-5-carboxylic acid [5-(3, 3-difluoro-pyrrolidine-1-carbonyl)-pyrrolidin-3-ylmethyl]-amide Example 70A 3-Hydroxy-pyrrolidine-1-carboxylic acid tert-butyl ester To a mixture of 3-hydroxypyrrolidine (11.17 mmol, 134.3 mmol) and triethylamine (23.4 mL) in dichloromethane/acetonitrile (150 mL, 4:1) was added di-tert-butyl dicarbonate (1.1 eq., 32.24 g). The mixture was stirred for 16 hours, partitioned between ethyl acetate and 1 N HCl, and the aqueous layer was extracted with ethyl acetate (2×25 mL). The combined organic extracts were washed with saturated NaHCO$_3$ solution, dried (Na$_2$SO$_4$), filtered and concentrated under reduced pressure. The material was used in the next step without purification. MS (CI) m/z 205 [M+NH$_4$]$^+$.

Example 70B

3-Oxo-pyrrolidine-1-carboxylic acid tert-butyl ester

To a mixture of oxalyl chloride (22.68 mL) in 200 mL of dichloromethane at −78° C. was slowly added DMSO (26.0 mL) via a syringe. After 5 minutes, Example 70A (134.3 mmol) in 60 mL of CH$_2$Cl$_2$ was slowly added. After 30 minutes, triethylamine (3.64 mL) was added and the mixture stirred at −78° C. for 40 minutes, after which it was stirred at 0° C. for 30 minutes. The mixture was diluted with additional dichloromethane (ca. 30 mL) and 1 N HCl was added. The organic layer was washed with brine, dried (Na$_2$SO$_4$), filtered and concentrated to provide the crude ketone (19.28 g). MS (CI) m/z 203 [M+NH$_4$]$^+$.

Example 70C 3,3-Difluoro-pyrrolidine-1-carboxylic acid tert-butyl ester

A mixture of Example 70B (6.35 g, 34.29 mmol) in 100 mL of dichloromethane was cooled to −50° C. followed by the addition of (diethylamino)sulfur trifluoride (1.6 eq., 9.94 mL). The mixture was slowly allowed to come to room temperature and stirred for 16 hours. Saturated aqueous NaHCO₃ solution was added slowly, and the mixture extracted with methylene chloride (3×25 mL). The combined organic extracts were dried (Na₂SO₄), filtered, concentrated and purified by flash chromatography (10% ethyl acetate/hexane) to provide the titled product. MS (CI) m/z+ 208 [M+H]⁺.

Example 70D 3,3-Difluoro-pyrrolidine

Example 70C (1.315 g, 36.34 mmol) in a mixture of trifluoroacetic acid (4 mL) in methylene chloride (4 mL) was stirred at room temperature for 3 hours and concentrated under reduced pressure to provide the desired amine as the trifluoroacetate salt. MS (CD) m/z 108 [M+H]⁺.

Example 70E (2S, 4R)-4-Hydroxy-pyrrolidine-1,2-dicarboxylic acid 2-benzyl ester 1-tert-butyl ester (2S, 4R)-4-Hydroxy-pyrrolidine-1,2-dicarboxylic acid 1-tert-butyl ester (6.6 g, 28.53 mmol), benzylbromide (3.39 mL, 28.53 mmol) and K₂CO₃ (5.51 g, 39.94 mmol) in 50 mL of acetonitrile were stirred and heated to 65° C. for 24 hours. The mixture was filtered, and the filtrate was concentrated to provide the crude benzyl ester (12.31 g) which was used in the next step without purification. MS (CI) m/z 322 [M+H]⁺.

Example 70F (2S, 4R)-4-Methanesulfonyloxy-pyrrolidine-1,2-dicarboxylic acid 2-benzyl ester 1-tert-butyl ester The title compound was obtained according to the procedure described for Example 17B by substituting (2S, 4R)-4-hydroxy-2-(thiazolidine-3-carbonyl)-pyrrolidine-1-carboxylic acid tert-butyl ester with (2S, 4R)-4-hydroxy-pyrrolidine-1,2-dicarboxylic acid 2-benzyl ester 1-tert-butyl ester (Example 70E). MS (CI) m/z 400 [M+H]⁺.

Example 70G (2S, 4S)-4-Cyano-pyrrolidine-1,2-dicarboxylic acid 2-benzyl ester 1-tert-butyl ester The title compound was synthesized by substituting Example 17B with Example 70F in the procedure described for Example 17C. MS (CI) m/z 331 [M+H]⁺.

Example 70H (2S, 4S)-4-Cyano-pyrrolidine-1,2-dicarboxylic acid 1-tert-butyl ester Example 70G (2.02 g, 6.13 mmol) in a mixture of methanol and THF (1:1, 10 mL) was treated with an aqueous solution of 1.7 N LiOH (6.1 mL) and stirred for 16 hours. The mixture was taken up in chloroform and 1 N HCl and the aqueous layer extracted with additional chloroform (3×25 mL). The combined organic layers were dried (Na₂SO₄), filtered and concentrated under reduced pressure to provide the titled compound which was used in the next step without purification. MS (ESI) m/z 258 [M+NH₄]⁺.

Example 70I (2S, 4S)-4-Cyano-2-(3,3-difluoro-pyrrolidine-1-carbonyl)-pyrrolidine-1-carboxylic acid tert-butyl ester Example 70H (6.12 mmoL) and 2-(1H-benzotriazol-1-yl)-1,1,3,3-tetramethyluronium tetrafluoroborate (1.4 eq, 2.75 g) were mixed in 4 mL of DMF after which a mixture of Example 70D (6.34 mmol) and triethylamine (2.4 eq., 2.04 mL) in 4 mL of methylene chloride was added. Additional triethylamine (0.85 mL) was added until the pH of the mixture reached ~6-7 (wet pH paper) and the mixture was stirred overnight. The mixture was diluted with ethyl acetate and extracted consecutively with 1N HCl and saturated NaHCO₃. The combined organic layers were dried (MgSO₄), filtered, concentrated under reduced pressure. The residue was purified by flash chromatography (65%-100% ethyl acetate/hexane) to provide the titled compound. MS (ESI) m/z 330 [M+H]⁺.

Example 70J (2S, 4R)-4-Aminomethyl-2-(3,3-difluoro-pyrrolidine-1-carbonyl)-pyrrolidine-1-carboxylic acid tert-butyl ester Example 70I (143 mg, 0.43 mmol) and Raney Nickel (1.4 g) were mixed in 10 mL of 20% NH₃ in methanol and hydrogenated in a Parr hydrogenator under 60 psi of H₂ for 16 hours. The solids were filtered off, and the filtrate was concentrated under reduced pressure to provide the titled compound (164 mg). MS (CI) m/z 334 [M+H]⁺.

Example 70K (2S, 4R)-4-{[(Benzo[1,3]dioxole-5-carbonyl)-amino]-methyl}-2-(3,3-difluoro-pyrrolidine-1-carbonyl)-pyrrolidine-1-carboxylic acid tert-butyl ester Example 70J (0.217 mmol) and triethylamine (121 µL) were mixed in 2 mL of methylene chloride followed by the addition of benzo[1,3]dioxole-5-carbonyl chloride (100 mg). The mixture was stirred for 16 hours after which the mixture was purified by reverse-phase HPLC to provide the desired amide product. MS (ESI) m/z 482 [M+H]⁺.

Example 70

(3S, 5S)-Benzo[1,3]dioxole-5-carboxylic acid [5-(3,3-difluoro-pyrrolidine-1-carbonyl)-pyrrolidin-3-ylmethyl]-amide Example 70K was processed as described in Example 17 to provide the title compound. MS (ESI) m/z 382 [M+H]⁺; ¹H NMR (500 MHz, methanol-d₄) δ ppm 1.76 (m, J=1.56 Hz, 1H) 2.43 (m, 1H) 2.52 (m, 1H) 2.69 (m, 1H) 2.78 (m, 1H) 3.21 (dd, J=11.54, 9.04 Hz, 1H) 3.46 (d, J=6.24 Hz, 2H) 3.50 (m, 1H) 3.75 (m, 2H) 3.86 (m, 2H) 4.55 (dt, J=41.48, 8.58 Hz, 1H) 6.03 (s, 2H) 6.89 (d, J=8.11 Hz, 1H) 7.30 (d, J=1.56 Hz, 1H) 7.41 (dd, J=8.11, 1.87 Hz, 1H).

Example 71

(3S, 5S)-N-[5-(3,3-Difluoro-pyrrolidine-1-carbonyl)-pyrrolidin-3-ylmethyl]-3-methoxy-benzamide The titled compound was synthesized by substituting benzo[1,3]dioxole-5-carbonyl chloride in Example 70 with 3-methoxy-benzoyl chloride. MS (ESI) m/z 368 [M+H]$^+$; $^1$H NMR (500 MHz, methanol-d$_4$) δ ppm 1.78 (m, 1H) 2.48 (m, 2H) 2.70 (m, 1H) 2.80 (m, 1H) 3.23 (m, 1H) 3.49 (d, J=6.55 Hz, 2H) 3.53 (m, 1H) 3.73 (m, 2H) 3.84 (s, 3H) 3.95 (m, 2H) 4.56 (dt, J=41.48, 8.58 Hz, 1H) 7.12 (m, 1H) 7.39 (m, 3H).

Example 72

(3S, 5S)-N-[5-(3,3-Difluoro-pyrrolidine-1-carbonyl)-pyrrolidin-3-ylmethyl]-isophthalamic acid methyl ester Monomethyl isophthalate (68.8 mg), 2-(1H-benzotriazol-1-yl)-1,1,3,3-tetramethyluronium tetrafluoroborate (132 mg) and Example 70J (0.294 mmol) were mixed in 1.2 mL of DMF followed by the addition of triethylamine (100 μL). The mixture was stirred for 16 hours and purified by reverse-phase HPLC. MS (ESI) m/z+496 [M+H]+. The residue was processed as described in Example 17 to provide the title compound. MS (ESI) m/z 396 [M+H]$^+$; $^1$H NMR (500 MHz, methanol-d$_4$) δ ppm 1.78 (m, 1H) 2.43 (m, 1H) 2.52 (m, 1H) 2.71 (m, 1H) 2.81 (m, 1H) 3.23 (dd, J=11.54, 9.04 Hz, 1H) 3.51 (d, J=6.55 Hz, 2H) 3.55 (m, 1H) 3.73 (m, 2H) 3.85 (m, 2H) 3.93 (s, 3H) 4.56 (dt, J=41.56, 8.69 Hz, 1H) 7.60 (t, J=7.80 Hz, 1H) 8.06 (ddd, J=7.80, 1.87, 1.25 Hz, 1H) 8.18 (m, 1H) 8.48 (m, 1H).

Example 73

(3S, 5S)-N-[5-(3,3-Difluoro-pyrrolidine-1-carbonyl-pyrrolidin-3-ylmethyl]-isophthalamic acid A mixture of Example 72 (58.8 mg) in 0.6 mL of methanol was treated with 1 mL of 1.7 N LiOH solution for 4 hours. Trifluoroacetic acid (300 μL) was added, and the mixture was purified by reverse-phase HPLC to provide the desired acid. MS (ESI) m/z 382 [M+H]$^+$; $^1$H NMR (500 MHz, methanol-d$_4$) δ ppm 1.57 (ddd, J=19.53, 12.97, 9.61 Hz, 1H) 2.22 (m, 1H) 2.32 (m, 1H) 2.50 (m, 1H) 2.61 (m, 1H) 3.02 (dd, J=11.60, 9.15 Hz, 1H) 3.31 (d, J=6.71 Hz, 2H) 3.32 (m, 1H) 3.54 (m, 2H) 3.66 (m, 2H) 4.36 (dt, J=41.58, 8.66 Hz, 1H) 7.38 (t, J=7.78 Hz, 1H) 7.84 (d, J=8.24 Hz, 1H) 7.98 (d, J=7.93 Hz, 1H) 8.28 (m, 1H).

Example 74

(3S, 3'S, 5S,)-N-[5-(3-Fluoro-pyrrolidine-1-carbonyl-pyrrolidin-3-ylmethyl]-isophthalamic acid

Example 74A (3R)-3-Hydroxy-pyrrolidine-1-carboxylic acid benzyl ester

R-(−)-3-Pyrrolidinol HCl salt (3.2 g, 25.89 mmol) and triethylamine (7.93 mL) were mixed in 60 mL of methylene chloride followed by the addition of benzyl chloroformate (4.08 mL). The mixture was stirred for 6 hours after which 1 N HCl was added, and the mixture was extracted with methylene chloride (3×). The combined organic extracts were dried (Na$_2$SO$_4$), filtered, concentrated and then purified by flash chromatography (50% then 80% ethyl acetate/hexane) to provide the desired product (2.78 g). MS (CI) m/z 222 [M+H]$^+$.

Example 74B (3S)-3-Fluoro-pyrrolidine-1-carboxylic acid benzyl ester

Example 74A (2.77g, 12.52 mmol) in 25 mL of methylene chloride was cooled to −78 °C. followed by the addition of (diethylamino)sulfur trifluoride (2.43 mL). The mixture was stirred for 16 hours and an aqueous solution of NaHCO$_3$ was added. The mixture was extracted with methylene chloride (2×) and the combined organic extracts dried (Na$_2$SO$_4$), filtered, concentrated and then purified by flash chromatography (15% then 25% ethyl acetate/hexane) to provide the desired product (2.22 g). MS (CI) m/z 224 [M+H]$^+$.

Example 74C (3S)-3-Fluoro-pyrrolidine

Example 74B (2.20 g, 9.85 mmol) and 0.52 g of 10% Pd/C were mixed in 12 mL of ethanol and stirred under an atmosphere of H$_2$ for 4.5 hours. The solids were filtered off, and 18 mL of 1 N HCl in diethyl ether were added to the filtrate. Evaporation of the volatiles provided the amine as the HCl salt (1.335 g). MS (CI) m/z+90 [M+H]$^+$.

Example 74

(3S, 3'S, 5S,)-N-[5-(3-Fluoro-pyrrolidine-1-carbonyl)-pyrrolidin-3-ylmethyl]-isophthalamic acid The titled compound was made according to procedure described in Example 73 by substituting 3,3-difluoro-pyrrolidine with (3S)-3-fluoro-pyrrolidine. MS (ESI) m/z+364 [M+H]$^+$; $^1$H NMR (500 MHz, methanol-d$_4$) δ ppm 1.78 (m, 1H) 2.21 (m, 2H) 2.79 (m, 2H) 3.26 (m, 1H) 3.52 (m, 3H) 3.64 (m, 2H) 3.82 (m, 2H) 4.53 (ddd, J=34.63, 8.89, 8.58 Hz, 1H) 5.34 (m, 1H) 7.59 (t, J=7.80 Hz, 1H) 8.05 (d, J=7.80 Hz, 1H) 8.19 (d, J=7.80 Hz, 1H) 8.48 (s, 1H).

Example 75

(3S, 5S)-3-Methanesulfonyl-N-[5-(morpholine-4-carbonyl)-pyrrolidin-3-ylmethyl]-benzamide

Example 75A (2S, 4R)-(4-Hydroxy-2-(morpholine-4-carbonyl)-pyrrolidine-1-carboxylic acid tert-butyl ester trans-Boc-L-Hydroxyproline (10.0 g, 43.3 mmol), 1-[3-(dimethylamino)propyl]-3-ethylcarbodiimide hydrochloride (10 g, 52.4 mmol) and HOBt (7.1 g, 52.6 mmol) were dissolved in THF/dichloromethane (10 mL/40 mL) at 0° C., and then N-methylmorpholine (11.5 mL, 104 mmol) and morpholine (5.8 mL, 67 mmol) were added to the mixture. The mixture was allowed to warm to room temperature and stirred for 12 hours. The reaction mixture was concentrated under reduced pressure, and the residue was partitioned between aqueous KHSO$_4$ and ethyl acetate. The aqueous layer was extracted with ethyl acetate (3×200 mL). The combined organic layers were washed with water, aqueous NaHCO$_3$, and brine. The organic layer was dried with magnesium sulfate, filtered and concentrated under reduced pressure to a white glassy solid residue to provide Example 75A. MS (DCI) m/e 301 (M+H)$^+$; $^1$H NMR (300 MHz, CDCl$_3$): δ ppm 1.39-1.50 (2d, 9H), 1.97-2.26 (m, 3H), 2.84

(m, 2H), 3.46-3.52 (m, 2H), 3.62-3.72 (m, 4H), 3.78-3.86 (m, 2H), 4.51 (m, 0.5H), 4.57 (m, 0.5H), 4.69-4.83 (m, 1H).

Example 75B (2S, 4R)-2-(Morpholine-4-carbonyl)-4-(toluene-4-sulfonyloxy)-pyrrolidine-1-carboxylic acid tert-butyl ester Example 75A (9.9 g, 33 mmol) was dissolved in pyridine (35 mL) and cooled to 0° C. in an ice/water bath under nitrogen. p-Toluenesulfonyl chloride (7.6 g, 40 mmol) was added in portions to the reaction mixture at 0° C. The reaction mixture was allowed to warm up to room temperature and stirred for 12 hours. Then the reaction mixture was concentrated under reduced pressure. The residue was partitioned between water and ethyl acetate. The aqueous layer was extracted with ethyl acetate (3×200 mL). The combined organic layers were washed with aqueous $KHSO_4$, aqueous $NaHCO_3$, and brine. The organic organic layer was dried over magnesium sulfate, filtered and concentrated under reduced pressure to a glassy solid. The residue was purified using a Biotage 40M eluting with 50% ethyl acetate and hexane to provide the titled compound. MS (DCI) m/e 455 $(M+H)^+$; $^1H$ NMR (400 MHz, $CD_3OD$) δ ppm 1.42 (m, 9H) 2.17-2.33 (m, 2H), 2.46 (s, 3H), 3.51-3.62 (m, 2H), 3.67-3.82 (m, 8H), 4.67-4.84 (m, 1H), 5.01 (m, 0.5H), 5.14 (m, 0.5H), 5.32 (m, 1H), 7.37(d, 1H), 7.80 (m, 1H), 8.02(s, 1H).

Example 75C (2S, 4S)-4-Cyano-2-(morpholine-4-carbonyl)-pyrrolidine-1-carboxylic acid tert-butyl ester Example 75B (9.1 g, 20 mmol) was dissolved in dry DMF (50 mL) under nitrogen. Tetrabutylammonium cyanide (26 g. 97 mmol) was added to the solution. The reaction mixture was heated at 50° C. for 60 hours. The DMF was distilled off under high vacuum. Cold water (100 mL) was added to the residue, and the mixture was extracted with ethyl acetate (3×300 mL). The combined organic layers were washed brine, dried over magnesium sulfate, and concentrated under reduced pressure. The residue was purified by Biotage 40M flash silica gel chromatography with 50% ethyl acetate and hexane in two portions to give the titled compound (2.75 g). MS (DCI) m/e 310 $(M+H)^+$, 317 $(M+NH_4^+)$; $^1H$ NMR (400 MHz, $CD_3OD$) δ ppm 1.44 (m, 9H), 2.17-2.52 (m, 2H), 2.65 (m, 1H) 3.11 (m, 1H) 3.38 (m, 1H) 3.45 (m, 1H), 3.60-3.82 (m, 4H) 3.98 (m, 1H) 4.59 (m, 1H), 4.71 (m, 1H), 4.85 (m, 1H),

Example 75D (2S, 4S)-4-Aminomethyl-2-(morpholine-4-carbonyl-pyrrolidine-1-carboxylic acid tert-butyl ester Example 75C (0.67 g, 2.2 mmole), $PtO_2$ (66 mg), and methanol (5 mL) were combined in a 20 mL pressure bottle. Aqueous HCl (6 M, 0.44 mL, 1.01 equiv.) was added with stirring, and the mixture was stirred under 60 psi of hydrogen for 30 minutes at room temperature. The reaction mixture was filtered through a nylon membrane and concentrated in vacuo. MS (DCI) m/e 310 $(M+H)^+$, 317 $(M+NH_4^+)$.

Example 75

(3S, 5S)-3-Methanesulfonyl-N-[5-(morpholine4-carbonyl)-pyrrolidin-3-ylmethyl]-benzamide Example 75 was prepared in the same manner as Example 23 by substituting Example 75D for Example 17D. Analytical data is for the HCl salt. MS (DCI) m/e 396 $(M+H)^+$; $^1H$ NMR (400 MHz, $CD_3OD$) δ ppm 8.40 (t, 3H), 8.15 (m, 2H), 7.76 (t, 1H), 4.70 (t, 1H), 3.71-3.50 (m, 16H), 3.24 (dt, 1H), 3.17 (s, 3H).

The following additional compounds, representative of compound of formula (I), may be prepared by one skilled in the art using known synthetic methodology or by using synthetic methodology described in the Schemes and Examples contained herein.

(5S)-1-(4-Ethyl-piperazin-1-yl)-2-[5-(thiazolidine-3-carbonyl)-pyrrolidin-3-yl]-ethanone;

(5S)-2-[5-(Thiazolidine-3-carbonyl)-pyrrolidin-3-yl]-N-p-tolyl-acetamide;

(5S)-1-(4-Phenyl-piperazin-1-yl)-2-[5-(thiazolidine-3-carbonyl)-pyrrolidin-3-yl]-ethanone;

(5S)-1-[4-(2-Fluoro-phenyl)-piperazin-1-yl]-2-[5-(thiazolidine-3-carbonyl)-pyrrolidin-3-yl]-ethanone;

(5S)-1-(1,3,4,9-Tetrahydro-β-carbolin-2-yl)-2-[5-(thiazolidine-3-carbonyl)-pyrrolidin-3-yl]-ethanone;

(5S)-N-(3-Chloro-phenyl)-2-[5-(thiazolidine-3-carbonyl)-pyrrolidin-3-yl]-acetamide;

(5S)-2-[5-(Thiazolidine-3-carbonyl)-pyrrolidin-3-yl]-N-thiophen-2-ylmethyl-acetamide;

(5S)-N-Benzyl-N-(2-hydroxy-ethyl)-2-[5-(thiazolidine-3-carbonyl)-pyrrolidin-3-yl]-acetamide;

(5S)-N-(2-Chloro-benzyl)-2-[5-(thiazolidine-3-carbonyl)-pyrrolidin-3-yl]-acetamide;

(5S)-N-[2-(4-Chloro-phenyl)-ethyl]-2-[5-(thiazolidine-3-carbonyl)-pyrrolidin-3-yl]-acetamide;

(5S)-1-[4-(4-Fluoro-phenyl)-piperazin-1-yl]-2-[5-(thiazolidine-3-carbonyl)-pyrrolidin-3-yl]-ethanone;

(5S)-N-(4-Methoxy-phenyl)-2-[5-(thiazolidine-3-carbonyl)-pyrrolidin-3-yl]-acetamide;

(5S)-N-(4-Fluoro-phenyl)-2-[5-(thiazolidine-3-carbonyl)-pyrrolidin-3-yl]-acetamide;

(5S)-1-(4-Methyl-piperazin-1-yl)-2-[5-(thiazolidine-3-carbonyl)-pyrrolidin-3-yl]-ethanone;

(5S)-N-Phenyl-2-[5-(thiazolidine-3-carbonyl)-pyrrolidin-3-yl]-acetamide;

(5S)-N-(1,2,3,4-Tetrahydro-naphthalen-1-yl)-2-[5-(thiazolidine-3-carbonyl)-pyrrolidin-3-yl]-acetamide;

(5S)-2-[5-(Thiazolidine-3-carbonyl)-pyrrolidin-3-yl]-N-o-tolyl-acetamide;

(5S)-N-Phenethyl-2-[5-(thiazolidine-3-carbonyl)-pyrrolidin-3-yl]-acetamide;

(5S)-N-(5-Methyl-furan-2-ylmethyl)-2-[5-(thiazolidine-3-carbonyl)-pyrrolidin-3-yl]-acetamide;

(5S)-2-[5-(Thiazolidine-3-carbonyl)-pyrrolidin-3-yl]-N-(2-thiophen-2-yl-ethyl)-acetamide;

(5S)-N-(4-Chloro-benzyl)-2-[5-(thiazolidine-3-carbonyl)-pyrrolidin-3-yl]-acetamide;

(5S)-1-(4-Hydroxy-piperidin-1-yl)-2-[5-(thiazolidine-3-carbonyl)-pyrrolidin-3-yl]-ethanone;

(5S)-1-{2-[5-(Thiazolidine-3-carbonyl)-pyrrolidin-3-yl]-acetyl}-piperidine-3-carboxylic acid amide;

(5S)-1-(4-Acetyl-piperazin-1-yl)-2-[5-(thiazolidine-3-carbonyl)-pyrrolidin-3-yl]-ethanone;

(5S)-1-[4-(2-Chloro-phenyl)-piperazin-1-yl]-2-[5-(thiazolidine-3-carbonyl)-pyrrolidin-3-yl]-ethanone;

(5S)-1-(2,6-Dimethyl-morpholin-4-yl)-2-[5-(thiazolidine-3-carbonyl)-pyrrolidin-3-yl]-ethanone;
(5S)-N-(4-Phenoxy-phenyl)-2-[5-(thiazolidine-3-carbonyl)-pyrrolidin-3-yl]-acetamide;
(5S)-N-(4-Amino-phenyl)-2-[5-(thiazolidine-3-carbonyl)-pyrrolidin-3-yl]-acetamide;
(5S)-N-Pyridin-3-ylmethyl-2-[5-(thiazolidine-3-carbonyl)-pyrrolidin-3-yl]-acetamide;
(5S)-N-Methyl-N-(2-pyridin-2-yl-ethyl)-2-[5-(thiazolidine-3-carbonyl)-pyrrolidin-3-yl]-acetamide;
(5S)-1-[4-(2-Hydroxy-ethyl)-piperazin-1-yl]-2-[5-(thiazolidine-3-carbonyl)-pyrrolidin-3-yl]-ethanone;
(3S, 5S)-3-(4-Chloro-phenyl)-N-[5-(thiazolidine-3-carbonyl)-pyrrolidin-3-ylmethyl]-propionamide;
(3S, 5S)-2-Hydroxy-N-({[5-(thiazolidine-3-carbonyl)-pyrrolidin-3-ylmethyl]-carbamoyl}-methyl)-benzamide;
(3S, 5S)-2-(3,4-Dimethyl-phenoxy)-N-[5-(thiazolidine-3-carbonyl)-pyrrolidin-3-ylmethyl]-acetamide;
(3S, 5S)-3-Phenoxy-N-[5-(thiazolidine-3-carbonyl)-pyrrolidin-3-ylmethyl]-propionamide
(2S, 3S, 5S)-2-Phenyl-N-[5-(thiazolidine-3-carbonyl)-pyrrolidin-3-ylmethyl]-butyramide;
(3S, 5S)-N-[5-(Thiazolidine-3-carbonyl)-pyrrolidin-3-ylmethyl]-4-thiophen-2-yl-butyramide;
(3S, 5S)-2-Benzyloxy-N-[5-(thiazolidine-3-carbonyl)-pyrrolidin-3-ylmethyl]-acetamide;
(3S, 5S)-N-[5-(Thiazolidine-3-carbonyl)-pyrrolidin-3-ylmethyl]-2-m-tolyloxy-acetamide;
(3S, 5S)-N-[5-(Thiazolidine-3-carbonyl)-pyrrolidin-3-ylmethyl]-2-o-tolyloxy-acetamide;
(3S, 5S)-2-(4-Chloro-2-methyl-phenoxy)-N-[5-(thiazolidine-3-carbonyl)-pyrrolidin-3-ylmethyl]-acetamide;
(3S, 5S)-3-(2,5-Dimethoxy-phenyl)-N-[5-(thiazolidine-3-carbonyl)-pyrrolidin-3-ylmethyl]-propionamide;
(3S, 5S)-4-Phenoxy-N-[5-(thiazolidine-3-carbonyl)-pyrrolidin-3-ylmethyl]-butyramide;
(2S', 3S, 5S)-2-Dipropylamino-N-[5-(thiazolidine-3-carbonyl)-pyrrolidin-3-ylmethyl]-propionamide;
(3S, 5S)-3-Methyl-2-phenyl-pentanoic acid [5-(thiazolidine-3-carbonyl)-pyrrolidin-3-ylmethyl]-amide;
(3S, 5S)-2-(3-Phenoxy-phenyl)-N-[5-(thiazolidine-3-carbonyl)-pyrrolidin-3-ylmethyl]-acetamide;
(3S, 5S)-4-Phenyl-N-[5-(thiazolidine-3-carbonyl)-pyrrolidin-3-ylmethyl]-butyramide;
(3S, 5S)-N-[5-(Thiazolidine-3-carbonyl)-pyrrolidin-3-ylmethyl]-2-thiophen-2-yl-acetamide;
(2R', 3S, 5S)-2-Hydroxy-4-phenyl-N-[5-(thiazolidine-3-carbonyl)-pyrrolidin-3-ylmethyl]-butyramide;
(3S, 5S)-2-(3,5-Difluoro-phenyl)-N-[5-(thiazolidine-3-carbonyl)-pyrrolidin-3-ylmethyl]-acetamide;
(3S, 5S)-3-(2-Chloro-phenyl)-N-[5-(thiazolidine-3-carbonyl)-pyrrolidin-3-ylmethyl]-propionamide;
(3S, 5S)-2,2-Diphenyl-N-[5-(thiazolidine-3-carbonyl)-pyrrolidin-3-ylmethyl]-acetamide;
(3S, 5S)-3-(3-Methoxy-phenyl)-N-[5-(thiazolidine-3-carbonyl)-pyrrolidin-3-ylmethyl]-propionamide;
(3S, 5S)-3-(4-Methoxy-phenyl)-N-[5-(thiazolidine-3-carbonyl)-pyrrolidin-3-ylmethyl]-propionamide;
(2'R, 3S, 5S)-2-Methoxy-2-phenyl-N-[5-(thiazolidine-3-carbonyl)-pyrrolidin-3-ylmethyl]-acetamide;
(3S, 5S)-N-[5-(Thiazolidine-3-carbonyl)-pyrrolidin-3-ylmethyl]-2-p-tolyloxy-acetamide;
(3S, 5S)-3-Ethoxy-N-[5-(thiazolidine-3-carbonyl)-pyrrolidin-3-ylmethyl]-propionamide;
(3S, 5S)-3-Phenyl-N-[5-(thiazolidine-3-carbonyl)-pyrrolidin-3-ylmethyl]-propionamide;
(3S, 5S)-1-(2-Methoxy-phenyl)-3-[5-(thiazolidine-3-carbonyl)-pyrrolidin-3-ylmethyl]-urea;
(3S, 5S)-1-Phenyl-3-[5-(thiazolidine-3-carbonyl)-pyrrolidin-3-ylmethyl]-urea;
(3S, 5S)-1-[5-(Thiazolidine-3-carbonyl)-pyrrolidin-3-ylmethyl]-3-p-tolyl-urea;
(3S, 5S)-Morpholine-4-carboxylic acid [5-(thiazolidine-3-carbonyl)-pyrrolidin-3-ylmethyl]-amide;
(3S, 5S)-1-(4-Fluoro-phenyl)-3-[5-(thiazolidine-3-carbonyl)-pyrrolidin-3-ylmethyl]-urea;
(3S, 5S)-1-(2,3-Dimethyl-phenyl)-3-[5-(thiazolidine-3-carbonyl)-pyrrolidin-3-ylmethyl]-urea;
(3S, 5S)-N-[5-(Pyrrolidine-1-carbonyl)-pyrrolidin-3-ylmethyl]-benzamide;
(3S, 5S)-4-Methyl-N-[5-(thiazolidine-3-carbonyl)-pyrrolidin-3-ylmethyl]-benzamide;
(3S, 5S)-2,2-Difluoro-benzo[1,3]dioxole-4-carboxylic acid [5-(thiazolidine-3-carbonyl)-pyrrolidin-3-ylmethyl]-amide;
(3S, 5S)-2-Fluoro-N-[5-(thiazolidine-3-carbonyl)-pyrrolidin-3-ylmethyl]-benzamide;
(3S, 5S)-N-[5-(Thiazolidine-3-carbonyl)-pyrrolidin-3-ylmethyl]-terephthalamic acid methyl ester;
(3S, 5S)-3-Methyl-N-[5-(thiazolidine-3-carbonyl)-pyrrolidin-3-ylmethyl]-benzamide;
(3S, 5S)-4-Amino-N-[5-(thiazolidine-3-carbonyl)-pyrrolidin-3-ylmethyl]-benzamide;
(3S, 5S)-2-Hydroxy-N-[5-(thiazolidine-3-carbonyl)-pyrrolidin-3-ylmethyl]-benzamide;
(3S, 5S)-3-Amino-N-[5-(pyrrolidine-1-carbonyl)-pyrrolidin-3-ylmethyl]-benzamide;
(3S, 5S)-2,3-Dimethyl-N-[5-(pyrrolidine-1-carbonyl)-pyrrolidin-3-ylmethyl]-benzamide;
(3S, 5S)-4-Methoxy-N-[5-(thiazolidine-3-carbonyl)-pyrrolidin-3-ylmethyl]-benzamide;
(3S, 5S)-3,5-Dichloro-N-[5-(thiazolidine-3-carbonyl)-pyrrolidin-3-ylmethyl]-benzamide;
(3S, 5S)-2-Methoxy-N-[5-(thiazolidine-3-carbonyl)-pyrrolidin-3-ylmethyl]-benzamide;
(3S, 5S)-3,5-Dimethyl-N-[5-(thiazolidine-3-carbonyl)-pyrrolidin-3-ylmethyl]-benzamide;
(3S, 5S)-4-Cyano-N-[5-(thiazolidine-3-carbonyl)-pyrrolidin-3-ylmethyl]-benzamide;
(3S, 5S)-2-Methyl-N-[5-(pyrrolidine-1-carbonyl)-pyrrolidin-3-ylmethyl]-benzamide;
(3S, 5S)-N-[5-(Pyrrolidine-1-carbonyl)-pyrrolidin-3-ylmethyl]-3-trifluoromethoxy-benzamide;
(3S, 5S)-2,3-Dihydro-benzo[1,4]dioxine-6-carboxylic acid [5-(pyrrolidine-1-carbonyl)-pyrrolidin-3-ylmethyl]-amide;
(3S, 5S)-N-[5-(Thiazolidine-3-carbonyl)-pyrrolidin-3-ylmethyl]-3-trifluoromethyl-benzamide;
(3S, 5S)-2,3-Dichloro-N-[5-(thiazolidine-3-carbonyl)-pyrrolidin-3-ylmethyl]-benzamide;
(3S, 5S)-4-Fluoro-N-[5-(thiazolidine-3-carbonyl)-pyrrolidin-3-ylmethyl]-benzamide;
(3S, 5S)-4-Amino-N-[5-(pyrrolidine-1-carbonyl)-pyrrolidin-3-ylmethyl]-benzamide;
(3S, 5S)-4-Acetylamino-N-[5-(thiazolidine-3-carbonyl)-pyrrolidin-3-ylmethyl]-benzamide;
(3S, 5S)-2-Bromo-N-[5-(thiazolidine-3-carbonyl)-pyrrolidin-3-ylmethyl]-benzamide;
(3S, 5S)-3,4-Dimethyl-N-[5-(thiazolidine-3-carbonyl)-pyrrolidin-3-ylmethyl]-benzamide;
(3S, 5S)-3,4-Dimethoxy-N-[5-(thiazolidine-3-carbonyl)-pyrrolidin-3-ylmethyl]-benzamide;

(3S, 5S)-3,4,5-Trimethoxy-N-[5-(thiazolidine-3-carbonyl)-pyrrolidin-3-ylmethyl]-benzamide;
(3S, 5S)-2,5-Dimethyl-N-[5-(thiazolidine-3-carbonyl)-pyrrolidin-3-ylmethyl]-benzamide;
(3S, 5S)-4-Dimethylamino-N-[5-(thiazolidine-3-carbonyl)-pyrrolidin-3-ylmethyl]-benzamide;
(3S, 5S)-N-[5-(Thiazolidine-3-carbonyl)-pyrrolidin-3-ylmethyl]-4-trifluoromethyl-benzamide;
(3S, 5S)-3-Cyano-N-[5-(pyrrolidine-1-carbonyl)-pyrrolidin-3-ylmethyl]-benzamide;
(3S, 5S)-N-[5-(Thiazolidine-3-carbonyl)-pyrrolidin-3-ylmethyl]-terephthalamic acid;
(3S, 5S)-N-[5-(Thiazolidine-3-carbonyl)-pyrrolidin-3-ylmethyl]-benzamide;
(3S, 5S)-3-Chloromethyl-N-[5-(thiazolidine-3-carbonyl)-pyrrolidin-3-ylmethyl]-benzamide;
(3S, 5S)-2-Chloro-N-[5-(thiazolidine-3-carbonyl)-pyrrolidin-3-ylmethyl]-benzamide;
(3S, 5S)-2-Methyl-N-[5-(thiazolidine-3-carbonyl)-pyrrolidin-3-ylmethyl]-benzamide;
(3S, 5S)-3-Acetyl-N-[5-(thiazolidine-3-carbonyl)-pyrrolidin-3-ylmethyl]-benzamide;
(3S, 5S)-1-Methyl-1H-benzotriazole-5-carboxylic acid [5-(thiazolidine-3-carbonyl)-pyrrolidin-3-ylmethyl]-amide;
(3S, 5S)-3-Bromo-N-[5-(pyrrolidine-1-carbonyl)-pyrrolidin-3-ylmethyl]-benzamide;
(3S, 5S)-3-Cyano-N-[5-(thiazolidine-3-carbonyl)-pyrrolidin-3-ylmethyl]-benzamide;
(3S, 5S)-2-Amino-N-[5-(pyrrolidine-1-carbonyl)-pyrrolidin-3-ylmethyl]-benzamide;
(3S, 5S)-3-Fluoro-N-[5-(thiazolidine-3-carbonyl)-pyrrolidin-3-ylmethyl]-benzamide;
(3S, 5S)-4-Bromo-N-[5-(thiazolidine-3-carbonyl)-pyrrolidin-3-ylmethyl]-benzamide;
(3S, 5S)-2,5-Dimethoxy-N-[5-(thiazolidine-3-carbonyl)-pyrrolidin-3-ylmethyl]-benzamide;
(3S, 5S)-2,5-Dichloro-N-[5-(thiazolidine-3-carbonyl)-pyrrolidin-3-ylmethyl]-benzamide;
(3S, 5S)-N-[5-(Thiazolidine-3-carbonyl)-pyrrolidin-3-ylmethyl]-2-trifluoromethyl-benzamide;
(3S, 5S)-2,4-Dimethoxy-N-[5-(thiazolidine-3-carbonyl)-pyrrolidin-3-ylmethyl]-benzamide;
(3S, 5S)-2,4-Dimethyl-N-[5-(thiazolidine-3-carbonyl)-pyrrolidin-3-ylmethyl]-benzamide;
(3S, 5S)-Quinoxaline-6-carboxylic acid [5-(pyrrolidine-1-carbonyl)-pyrrolidin-3-ylmethyl]-amide;
(3S, 5S)-4-Cyano-N-[5-(pyrrolidine-1-carbonyl)-pyrrolidin-3-ylmethyl]-benzamide;
(3S, 5S)-2,3-Dichloro-N-[5-(pyrrolidine-1-carbonyl)-pyrrolidin-3-ylmethyl]-benzamide;
(3S,5S)-2,2-Difluoro-benzo[1,3]dioxole-5-carboxylic acid [5-(pyrrolidine-1-carbonyl)-pyrrolidin-3-ylmethyl]-amide;
(3S,5S)-3-Hydroxy-N-[5-(pyrrolidine-1-carbonyl)-pyrrolidin-3-ylmethyl]-benzamide;
(3S, 5S)-3-Methoxy-N-[5-(pyrrolidine-1-carbonyl)-pyrrolidin-3-ylmethyl]-benzamide;
(3S, 5S)-Acetic acid 2-{[5-(thiazolidine-3-carbonyl)-pyrrolidin-3-ylmethyl]-carbamoyl}-phenyl ester;
(3S, 5S)-4-Chloro-N-[5-(thiazolidine-3-carbonyl)-pyrrolidin-3-ylmethyl]-benzamide;
(3S, 5S)-N-[5-(Pyrrolidine-1-carbonyl)-pyrrolidin-3-ylmethyl]-3-trifluoromethyl-benzamide;
(3S, 5S)-4-Methoxy-N-[5-(pyrrolidine-1-carbonyl)-pyrrolidin-3-ylmethyl]-benzamide;
(3S, 5S)-2,4-Dichloro-N-[5-(thiazolidine-3-carbonyl)-pyrrolidin-3-ylmethyl]-benzamide;
(3S, 5S)-3,4-Dichloro-N-[5-(thiazolidine-3-carbonyl)-pyrrolidin-3-ylmethyl]-benzamide;
(3S, 5S)-2-Methoxy-N-[5-(thiazolidine-3-carbonyl)-pyrrolidin-3-ylmethyl]-benzamide;
(3S, 5S)-3,5-Dimethoxy-N-[5-(thiazolidine-3-carbonyl)-pyrrolidin-3-ylmethyl]-benzamide;
(3S, 5S)-2,3-Dimethoxy-N-[5-(thiazolidine-3-carbonyl)-pyrrolidin-3-ylmethyl]-benzamide;
(3S, 5S)-3-Piperazin-1-ylmethyl-N-[5-(thiazolidine-3-carbonyl)-pyrrolidin-3-ylmethyl]-benzamide;
(3S, 5S)-4-Fluoro-N-[5-(pyrrolidine-1-carbonyl)-pyrrolidin-3-ylmethyl]-benzamide;
(3S, 5S)-3-Chloro-N-[5-(pyrrolidine-1-carbonyl)-pyrrolidin-3-ylmethyl]-benzamide;
(3S, 5S)-3-Methyl-N-[5-(pyrrolidine-1-carbonyl)-pyrrolidin-3-ylmethyl]-benzamide;
(3S, 5S)-Thiophene-2-carboxylic acid [5-(pyrrolidine-1-carbonyl)-pyrrolidin-3-ylmethyl]-amide;
(3S, 5S)-Pyrimidine-4-carboxylic acid [5-(thiazolidine-3-carbonyl)-pyrrolidin-3-ylmethyl]-amide;
(3S, 5S)-Pyridazine-3-carboxylic acid [5-(thiazolidine-3-carbonyl)-pyrrolidin-3-ylmethyl]-amide;
(3S, 5S)-3-Hydroxy-pyridine-2-carboxylic acid [5-(thiazolidine-3-carbonyl)-pyrrolidin-3-ylmethyl]-amide;
(3S, 5S)-Pyridine-2-carboxylic acid [5-(pyrrolidine-1-carbonyl)-pyrrolidin-3-ylmethyl]-amide;
(3S, 5S)-Thiophene-2-carboxylic acid [5-(thiazolidine-3-carbonyl)-pyrrolidin-3-ylmethyl]-amide;
(3S, 5S)-1-Methyl-1H-pyrrole-2-carboxylic acid [5-(pyrrolidine-1-carbonyl)-pyrrolidin-3-ylmethyl]-amide;
(3S, 5S)-2,5-Dimethyl-furan-3-carboxylic acid [5-(thiazolidine-3-carbonyl)-pyrrolidin-3-ylmethyl]-amide;
(3S, 5S)-Furan-3-carboxylic acid [5-(thiazolidine-3-carbonyl)-pyrrolidin-3-ylmethyl]-amide;
(3S, 5S)-5-Methyl-3-phenyl-isoxazole-4-carboxylic acid [5-(thiazolidine-3-carbonyl)-pyrrolidin-3-ylmethyl]-amide;
(3S, 5S)-2-Methyl-cyclopropanecarboxylic acid [5-(thiazolidine-3-carbonyl)-pyrrolidin-3-ylmethyl]-amide;
(3S, 5S)-3,5-Dimethyl-isoxazole-4-carboxylic acid [5-(thiazolidine-3-carbonyl)-pyrrolidin-3-ylmethyl]-amide;
(3S, 5S)-Quinoxaline-2-carboxylic acid [5-(thiazolidine-3-carbonyl)-pyrrolidin-3-ylmethyl]-amide;
(3S, 5S)-Furan-2-carboxylic acid [5-(pyrrolidine-1-carbonyl)-pyrrolidin-3-ylmethyl]-amide;
(3S, 5S)-1-Acetyl-piperidine-4-carboxylic acid [5-(thiazolidine-3-carbonyl)-pyrrolidin-3-ylmethyl]-amide;
(3S, 5S)-6-Chloro-2H-chromene-3-carboxylic acid [5-(thiazolidine-3-carbonyl)-pyrrolidin-3-ylmethyl]-amide;
(3S, 5S)-6-Hydroxy-N-[5-(thiazolidine-3-carbonyl)-pyrrolidin-3-ylmethyl]-nicotinamide;
(3S, 5S)-5-Methyl-thiophene-2-carboxylic acid [5-(thiazolidine-3-carbonyl)-pyrrolidin-3-ylmethyl]-amide;
(3S, 5S)-6-Hydroxy-N-[5-(pyrrolidine-1-carbonyl)-pyrrolidin-3-ylmethyl]-nicotinamide;
(3S, 5S)-Benzo[b]thiophene-2-carboxylic acid [5-(thiazolidine-3-carbonyl)-pyrrolidin-3-ylmethyl]-amide;
(3S, 5S)-5-Methyl-isoxazole-3-carboxylic acid [5-(thiazolidine-3-carbonyl)-pyrrolidin-3-ylmethyl]-amide;
(3S, 5S)-4-Hydroxy-cyclohexanecarboxylic acid [5-(pyrrolidine-1-carbonyl)-pyrrolidin-3-ylmethyl]-amide;
(3S, 5S)-N-[5-(Thiazolidine-3-carbonyl)-pyrrolidin-3-ylmethyl]-nicotinamide;
(3S, 5S)-1-Methyl-cyclopropanecarboxylic acid [5-(thiazolidine-3-carbonyl)-pyrrolidin-3-ylmethyl]-amide;
(3S, 5S)-N-[5-(Thiazolidine-3-carbonyl)-pyrrolidin-3-ylmethyl]-isonicotinamide;

(3S, 5S)-Thiazole-5-carboxylic acid [5-(thiazolidine-3-carbonyl)-pyrrolidin-3-ylmethyl]-amide;
(3S, 5S)-Thiophene-3-carboxylic acid [5-(pyrrolidine-1-carbonyl)-pyrrolidin-3-ylmethyl]-amide;
(3S, 5S)-1H-Indole-3-carboxylic acid [5-(pyrrolidine-1-carbonyl)-pyrrolidin-3-ylmethyl]-amide;
(3S, 5S)-5-Methyl-pyrazine-2-carboxylic acid [5-(thiazolidine-3-carbonyl)-pyrrolidin-3-ylmethyl]-amide;
(3S, 5S)-2-Hydroxy-N-[5-(thiazolidine-3-carbonyl)-pyrrolidin-3-ylmethyl]-nicotinamide;
(3S, 5S)-N-[5-(Pyrrolidine-1-carbonyl)-pyrrolidin-3-ylmethyl]-isonicotinamide;
(3S, 5S)-2H-Pyrazole-3-carboxylic acid [5-(thiazolidine-3-carbonyl)-pyrrolidin-3-ylmethyl]-amide;
(3S, 5S)-5-Methyl-1-phenyl-1H-pyrazole-4-carboxylic acid [5-(thiazolidine-3-carbonyl)-pyrrolidin-3-ylmethyl]-amide;
(3S, 5S)-2-Hydroxy-6-methyl-N-[5-(thiazolidine-3-carbonyl)-pyrrolidin-3-ylmethyl]-nicotinamide;
(2S, 4S)-{4-[(Dibenzylamino)-methyl]-pyrrolidin-2-yl}-thiazolidin-3-yl-methanone;
(2S, 4R)-Thiazolidin-3-yl-(4-{[(thiophen-3-ylmethyl)-amino]-methyl}-pyrrolidin-2-yl)-methanone;
(3S, 5S)-Thiophene-2-sulfonic acid [5-(thiazolidine-3-carbonyl)-pyrrolidin-3-ylmethyl]-amide;
(3S, 5S)-3-Methoxy-N-[5-(thiazolidine-3-carbonyl)-pyrrolidin-3-ylmethyl]-benzenesulfonamide;
(3S, 5S)-Quinoline-8-sulfonic acid [5-(thiazolidine-3-carbonyl)-pyrrolidin-3-ylmethyl]-amide;
(3S, 5S)-N-[5-(Thiazolidine-3-carbonyl)-pyrrolidin-3-ylmethyl]-3-trifluoromethyl-benzenesulfonamide;
(3S, 5S)-Naphthalene-1-sulfonic acid [5-(thiazolidine-3-carbonyl)-pyrrolidin-3-ylmethyl]-amide;
(3S, 5S)-3-Bromo-N-[5-(thiazolidine-3-carbonyl)-pyrrolidin-3-ylmethyl]-benzenesulfonamide;
(3S, 5S)-2,5-Dimethyl-N-[5-(thiazolidine-3-carbonyl)-pyrrolidin-3-ylmethyl]-benzenesulfonamide;
(3S, 5S)-Naphthalene-2-sulfonic acid [5-(thiazolidine-3-carbonyl)-pyrrolidin-3-ylmethyl]-amide;
(3S, 5S)-N-[5-(Thiazolidine-3-carbonyl)-pyrrolidin-3-ylmethyl]-benzenesulfonamide;
(3S, 5S)-3-Chloro-N-[5-(thiazolidine-3-carbonyl)-pyrrolidin-3-ylmethyl]-benzenesulfonamide;
(3S, 5S)-[5-(Thiazolidine-3-carbonyl)-pyrrolidin-3-ylmethyl]-carbamic acid naphthalen-1-yl ester;
(3S, 5S)-[5-(Thiazolidine-3-carbonyl)-pyrrolidin-3-ylmethyl]-carbamic acid heptyl ester;
(3S, 5S)-[5-(Thiazolidine-3-carbonyl)-pyrrolidin-3-ylmethyl]-carbamic acid benzyl ester;
(Z/E)-[5-(Thiazolidine-3-carbonyl)-pyrrolidin-3-ylidene]-acetic acid methyl ester;
(Z/E)-N-Benzyl-2-[5-(thiazolidine-3-carbonyl)-pyrrolidin-3-ylidene]-acetamide;
(Z/E)-N-Phenyl-2-[5-(thiazolidine-3-carbonyl)-pyrrolidin-3-ylidene]-acetamide;
(5S)-2-[5-(Thiazolidine-3-carbonyl)-pyrrolidin-3-yl]-1-(4-o-tolyl-piperazin-1-yl)-ethanone;
(5S)-2-[5-(Thiazolidine-3-carbonyl)-pyrrolidin-3-yl]-N-m-tolyl-acetamide;
(5S)-2-[5-(Thiazolidine-3-carbonyl)-pyrrolidin-3-yl]-N-thiophen-3-ylmethyl-acetamide;
(5S)-N-Benzyl-2-[5-(thiazolidine-3-carbonyl)-pyrrolidin-3-yl]-acetamide;
(5S)-N-(1-Phenyl-ethyl)-2-[5-(thiazolidine-3-carbonyl)-pyrrolidin-3-yl]-acetamide;
(5S)-N-(3-Imidazol-1-yl-propyl)-2-[5-(thiazolidine-3-carbonyl)-pyrrolidin-3-yl]-acetamide;
(5S)-N-(3-Phenyl-propyl)-2-[5-(thiazolidine-3-carbonyl)-pyrrolidin-3-yl]-acetamide; and
(3S, 5S)-N-[5-(Morpholine-4-carbonyl)-pyrrolidin-3-ylmethyl]-isophthalamic acid.

What is claimed is:
1. A compound of formula (IV),

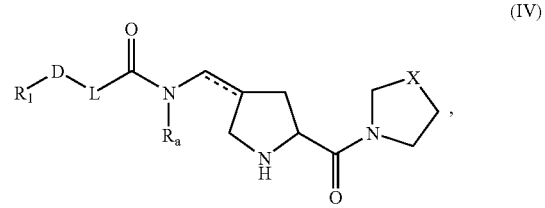

or therapeutically suitable salt, ester or prodrug, thereof, wherein

is a member selected from the group consisting of a single and double bond;
D is a bond or is a member selected from the group consisting of —C(O)—, —C(O)—N($R_b$)—, —N($R_b$)—, —N($R_b$)—C(O)—, —N($R_b$)—S(O)$_2$—, —O—, and —S(O)$_2$—N($R_b$)—;
L is a member selected from the group consisting of a bond, —(CH$_2$)$_m$—CR$_d$R$_e$—(CH$_2$)$_n$—, aryl, cycloalkyl, and heterocycle;
m and n are each independently 0, 1, 2, 3 or 4;
$R_1$ is a member selected from the group consisting of aryl, alkyl, arylalkyl, cycloalkyl and heterocycle;
$R_a$ and $R_b$ are each independently members selected from the group consisting of hydrogen, alkyl, arylalkyl and heterocyclealkyl and hydroxyalkyl;
$R_d$ and $R_e$ are each independently members selected from the group consisting of hydrogen, alkyl, alkoxy, alkoxyalkyl, aryl, arylalkyl, halo, haloalkyl, heterocycle, heterocyclealkyl, hydroxy and hydroxyalkyl, and $R_d$ and $R_e$ taken together with the atom to which they are attached form cycloalkyl; and
X is a member selected from the group consisting of —CH$_2$—, —CHF—, —CF$_2$—, —O—, —S— and —CH$_2$O—.

2. The compound according to claim 1, that is a member selected from the group consisting of
(3S, 5S)-Pentanedioic acid phenylamide-5-(thiazolidine-3-(carbonyl)-pyrrolidin-3-yl)methyl)-amide;
(3S, 5S)-2-(4-methanesulfonyl-phenyl)-N-(5-(thiazolidine-3-carbonyl)-pyrrolidin-3-ylmethyl)-acetamide;
(3S, 5S)-N-({[5-(Thiazolidine-3-carbonyl)-pyrrolidin-3-ylmethyl]-carbamoyl}-methyl)-benzamide;
(3S, 5S)-2-(4-Hydroxy-trans-cyclohexylamino)-N-[5-(thiazolidine-3-carbonyl)-pyrrolidin-3-ylmethyl]-acetamide;
(3S, 5S)-2-(3-Methoxy-phenoxy)-N-[5-(thiazolidine-3-carbonyl)-pyrrolidin-3-ylmethyl]-acetamide;
(3S, 5S)-N-5-(thiazolidine-3-carbonyl)-pyrrolidine-3-ylmethyl)-2-(toluene-4-sulfonylamino)acetamide;
(3S, 5S)-4-(4-Methoxy-phenyl)-4-oxo-N-[5-(thiazolidine-3-carbonyl)-pyrrolidin-3-ylmethyl]-butyramide;

(3S, 5S)-1-(4-Cyano-phenyl)-3-[5-(thiazolidine-3-carbonyl)-pyrrolidin-3-ylmethyl]-urea;
(3S, 5S)-1-Cyclopentyl-3-[5-(thiazolidine-3-carbonyl)-pyrrolidin-3-ylmethyl]-urea;
(3S, 5S)-N-[5-(Thiazolidine-3-carbonyl)-pyrrolidin-3-ylmethyl]-isophthalamic acid methyl ester;
(3S, 5S)-N-Methyl-N-[5-(thiazolidine-3-carbonyl)-pyrrolidin-3-ylmethyl]-benzamide;
(3S, 5S)-3-Bromo-N-[5-(thiazolidine-3-carbonyl)-pyrrolidin-3-ylmethyl]-benzamide;
(3S, 5S)-2,3-Dimethyl-N-[5-(thiazolidine-3-carbonyl)-pyrrolidin-3-ylmethyl]-benzamide;
(3S, 5S)-N-[5-(Thiazolidine-3-carbonyl)-pyrrolidin-3-ylmethyl]-isophthalamic acid;
(3S, 5S)-3-Methanesulfonyl-N-[5-(thiazolidine-3-carbonyl)-pyrrolidin-3-ylmethyl]-benzamide;
(3S, 5S)-4-Hydroxy-N-[5-(thiazolidine-3-carbonyl)-pyrrolidin-3-ylmethyl]-benzamide;
(3S, 5S)-2,3-Dihydro-benzo[1,4]dioxine-6-carboxylic acid [5-(thiazolidine-3-carbonyl)-pyrrolidin-3-ylmethyl]-amide;
(3S, 5S)-2,2-Difluoro-benzo[1,3]dioxole-5-carboxylic acid [5-(thiazolidine-3-carbonyl)-pyrrolidin-3-ylmethyl]-amide;
(3S, 5S)-N-[5-(Thiazolidine-3-carbonyl)-pyrrolidin-3-ylmethyl]-3-trifluoromethoxy-benzamide;
(3S, 5S)-N-[5-(Thiazolidine-3-carbonyl)-pyrrolidin-3-ylmethyl]-3-[1,2,4]triazol-1-ylmethyl-benzamide;
(3S, 5S)-3-Chloro-N-[5-(thiazolidine-3-carbonyl)-pyrrolidin-3-ylmethyl]-benzamide;
(3S, 5S)-3-(1H-Tetrazol-5-yl)-N-[5-(thiazolidine-3-carbonyl)-pyrrolidin-3-ylmethyl]-benzamide;
(3S, 5S)-2,3-Dihydro-benzofuran-5-carboxylic acid [5-(thiazolidine-3-carbonyl)-pyrrolidin-3-ylmethyl]-amide;
(3S, 5S)-3-Methanesulfonylaminocarbonyl-N-[5-(thiazolidine-3-carbonyl)-pyrrolidin-3-ylmethyl]-benzamide;
(3S, 5S)-4-Phenoxymethyl-N-[5-(thiazolidine-3-carbonyl)-pyrrolidin-3-ylmethyl]-benzamide;
(3S, 5S)-3-Imidazol-1-ylmethyl-N-[5-(thiazolidine-3-carbonyl)-pyrrolidin-3-ylmethyl]-benzamide;
(3S, 5S)-N-[5-(Thiazolidine-3-carbonyl)-pyrrolidin-3-ylmethyl]-benzamide;
(3S, 5S)-3-Acetyl-N-[5-(thiazolidine-3-carbonyl)-pyrrolidin-3-ylmethyl]-benzamide;
(3S, 5S)-Benzo[1,3]dioxole-5-carboxylic acid [5-(thiazolidine-3-carbonyl)-pyrrolidin-3-ylmethyl]-amide;
(3S, 5S)-4-Methanesulfonyl-N-[5-(thiazolidine-3-carbonyl)-pyrrolidin-3-ylmethyl]-benzamide;
(3S, 5S)-3-Dimethylamino-N-[5-(pyrrolidine-1-carbonyl)-pyrrolidin-3-ylmethyl]-benzamide;
(3S, 5S)-4-Phenoxy-N-[5-(thiazolidine-3-carbonyl)-pyrrolidin-3-ylmethyl]-benzamide;
(3S, 5S)-3-Amino-N-[5-(thiazolidine-3-carbonyl)-pyrrolidin-3-ylmethyl]-benzamide;
(3S, 5S)-4-Hydroxy-N-[5-(pyrrolidine-1-carbonyl)-pyrrolidin-3-ylmethyl]-benzamide;
(3S, 5S)-3-Hydroxy-N-[5-(thiazolidine-3-carbonyl)-pyrrolidin-3-ylmethyl]-benzamide;
(3S, 5S)-N-[5-(Pyrrolidine-1-carbonyl)-pyrrolidin-3-ylmethyl]-isophthalamic acid;
(3S, 5S)-3-Dimethylamino-N-[5-(thiazolidine-3-carbonyl)-pyrrolidin-3-ylmethyl]-benzamide;
(3S, 5S)-3-Methoxy-N-[5-(thiazolidine-3-carbonyl)-pyrrolidin-3-ylmethyl]-benzamide;
(3S, 5S)-N-[5-(Pyrrolidine-1-carbonyl)-pyrrolidin-3-ylmethyl]-isophthalamic acid methyl ester;
(3S, 5S)-Quinoxaline-6-carboxylic acid [5-(thiazolidine-3-carbonyl)-pyrrolidin-3-ylmethyl]-amide;
(3S, 5S)-2-Amino-N-[5-(thiazolidine-3-carbonyl)-pyrrolidin-3-ylmethyl]-benzamide;
(3S, 5S)-Benzo[1,3]dioxole-5-carboxylic acid [5-(pyrrolidine-1-carbonyl)-pyrrolidin-3-ylmethyl]-amide;
(3S, 5S)-2,3-Dihydro-benzofuran-5-carboxylic acid [5-(pyrrolidine-1-carbonyl)-pyrrolidin-3-ylmethyl]-amide;
(3S, 5S)-Pyridine-2-carboxylic acid [5-(thiazolidine-3-carbonyl)-pyrrolidin-3-ylmethyl]-amide;
(3S, 5S)-1-Methyl-1H-pyrrole-2-carboxylic acid [5-(thiazolidine-3-carbonyl)-pyrrolidin-3-ylmethyl]-amide;
(3S, 5S)-1-Phenyl-cyclopropanecarboxylic acid [5-(thiazolidine-3-carbonyl)-pyrrolidin-3-ylmethyl]-amide;
(3S, 5S)-Thiazole-4-carboxylic acid [5-(thiazolidine-3-carbonyl)-pyrrolidin-3-ylmethyl]-amide;
(3S, 5S)-Thiophene-3-carboxylic acid [5-(thiazolidine-3-carbonyl)-pyrrolidin-3-ylmethyl]-amide;
(3S, 5S)-6-Chloro-N-[5-(thiazolidine-3-carbonyl)-pyrrolidin-3-ylmethyl]-nicotinamide;
(3S, 5S)-1H-Indole-3-carboxylic acid [5-(thiazolidine-3-carbonyl)-pyrrolidin-3-ylmethyl]-amide;
(3S, 5S)-3-Methyl-thiophene-2-carboxylic acid [5-(pyrrolidine-1-carbonyl)-pyrrolidin-3-ylmethyl]-amide;
(3S, 5S)-Furan-2-carboxylic acid [5-(thiazolidine-3-carbonyl)-pyrrolidin-3-ylmethyl]-amide;
(3S, 5S)-Pyrazine-2-carboxylic acid [5-(thiazolidine-3-carbonyl)-pyrrolidin-3-ylmethyl]-amide;
(3S, 5S)-3-Methyl-thiophene-2-carboxylic acid [5-(thiazolidine-3-carbonyl)-pyrrolidin-3-ylmethyl]-amide;
(3S, 5S)-Thiazole-4-carboxylic acid [5-(pyrrolidine-1-carbonyl)-pyrrolidin-3-ylmethyl]-amide;
(3S, 5S)-Cyclohexanecarboxylic acid [5-(pyrrolidine-1-carbonyl)-pyrrolidin-3-ylmethyl]-amide;
(3S, 5S)-[5-(Thiazolidine-3-carbonyl)-pyrrolidin-3-ylmethyl]-carbamic acid phenyl ester;
(3S, 5S)-[5-(Thiazolidine-3-carbonyl)-pyrrolidin-3-ylmethyl]-carbamic acid 2-chloro-benzyl ester;
(3S, 5S)-Benzo[1,3]dioxole-5-carboxylic acid [5-(3,3-difluoro-pyrrolidine-1-carbonyl)-pyrrolidin-3-ylmethyl]-amide;
(3S, 5S)-N-[5-(3,3-Difluoro-pyrrolidine-1-carbonyl)-pyrrolidin-3-ylmethyl]-3-methoxy-benzamide;
(3S, 5S)-N-[5-(3,3-Difluoro-pyrrolidine-1-carbonyl)-pyrrolidin-3-ylmethyl]-isophthalamic acid methyl ester;
(3S, 5S)-N-[5-(3,3-Difluoro-pyrrolidine-1-carbonyl)-pyrrolidin-3-ylmethyl]-isophthalamic acid; and
(3S, 3'R, 5S,)-N-[5-(3-Fluoro-pyrrolidine-1-carbonyl)-pyrrolidin-3-ylmethyl]-isophthalamic acid; and
(3S, 5S)-3-Methanesulfonyl-N-[5-(morpholine-4-carbonyl)-pyrrolidin-3-ylmethyl]-benzamide.

* * * * *